Figure 2:
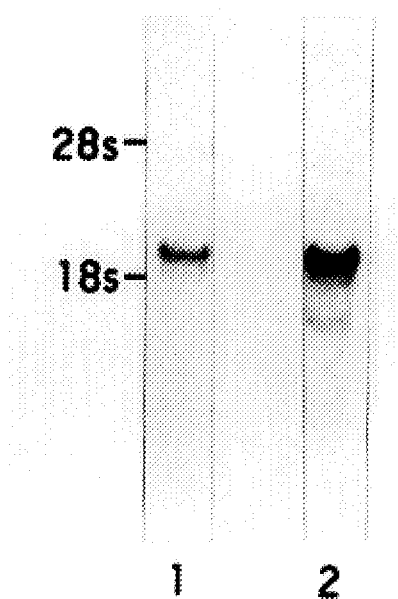

United States Patent [19]

Purchio et al.

[11] Patent Number: 5,844,085
[45] Date of Patent: Dec. 1, 1998

[54] CLONING AND EXPRESSION OF SIMIAN TRANSFORMING GROWTH FACTOR β1

[75] Inventors: Anthony F. Purchio, Seattle, Wash.; Larry Gentry, Maumee, Ohio; Daniel Twardzik, Bainbridge Island; Amy M. Brunner, Seattle, both of Wash.

[73] Assignee: Bristol-Myers Squibb Pharmaceutical Research Institute-Seattle, Seattle, Wash.

[21] Appl. No.: 958,522

[22] Filed: Oct. 8, 1992

Related U.S. Application Data

[63] Continuation of Ser. No. 353,728, May 17, 1989, abandoned, which is a continuation-in-part of Ser. No. 350,171, Apr. 17, 1989, abandoned, which is a continuation-in-part of Ser. No. 285,917, Dec. 16, 1988, abandoned, which is a continuation-in-part of Ser. No. 189,894, May 3, 1988, abandoned, which is a continuation-in-part of Ser. No. 147,842, Jan. 25, 1988, abandoned, which is a continuation-in-part of Ser. No. 55,662, May 29, 1987, abandoned.

[51] Int. Cl.[6] .................. C07K 14/495; A61K 38/18; A61K 38/19

[52] U.S. Cl. .............. 530/351; 424/85.1; 424/198.1; 530/380; 530/386; 530/399

[58] Field of Search ................. 424/85.1, 198.1; 435/69.5, 69.6, 172.3, 240.2, 252.3, 252.33, 320.1; 530/351, 380, 386, 399; 536/23.5, 23.51

[56] References Cited

U.S. PATENT DOCUMENTS

| 4,714,613 | 12/1987 | Shouval et al. ................ 424/86 |
| 4,886,747 | 12/1989 | Derynck et al. ................ 435/69.4 |

OTHER PUBLICATIONS

Tucker et al., "Growth Inhibitor from BSC–1 Cells Closely Related to Platelet Type βTransforming Growth Factor," *Science* 226:705–707, 9 Nov. 1984.

Derynck, et al., "Human Transforming Growth Factor–β Complementary DNA Sequence and Expression in Normal and Transformed Cells," *Nature* 316:701–705, 22 Aug. 1985.

Roberts et al. "Type β Transforming Growth Factor:A Bifunctional Regulator of Cellular Growth," *Proc. Natl. Acad. Sci. USA* 82:119–123, Jan., 1985.

Derynck et al., "The Murine Transforming Growth Factor–β Precursor," *J. Biol. Chem.* 261(10):4377–4379, 1986.

Sharples et al., "Cloning and Sequence Analysis of Simian Transforming Growth Factor–β cDNA," *DNA* 6(3):239–244, Jun. 1987.

*Primary Examiner*—Robert D. Budens
*Attorney, Agent, or Firm*—Pennie & Edmonds

[57] ABSTRACT

Recombinant transforming growth factor-β1 (TGF-β1) is expressed to high levels in Chinese hamster ovary (CHO) cells using dihydrofolate reductase (dhfr) gene amplification. The expression plasmid was derived from the pSV2 vectors and contained, in tandem, the simian TGF-β1 and mouse dhfr cDNAs. Transcription of both cDNAs was controlled by the SV40 early promoter. Stepwise selection of transfected CHO cells in increasing concentrations of methotrexate yielded cell lines expressing amplified TGF-β1 nucleic acid sequences. The expression plasmid DNA was amplified greater than 35-fold in one of the methotrexate selected transfectants. The major proteins secreted by these cells consisted of latent TGF-β1 and TGF-β1 precursor polypeptides as judged by immunoblots using site-specific anti-peptide antibodies derived from various regions of the TGF-β1 precursor. Levels of recombinant TGF-β1 protein secreted by these cells approached 30 ug/24 hour/$10^7$ cells. Expression vectors encoding TGF-β1 precursor variants which direct the synthesis and secretion of TGF-β1 in transfected mammalian cells are also described.

32 Claims, 64 Drawing Sheets

FIG.1A

FIG. 1B

```
                              110                        120
         Ala Asp Tyr Tyr Ala Lys Glu Val Thr Arg Val Leu Met Val Glu Thr His Asn Glu Ile Tyr Asp Lys Phe Lys
SIMIAN   GCC GAC TAC TAC GCC AAG GAG GTC ACC CGC GTC CTA ATG GTG GAA ACC CAC AAC GAA ATC TAT GAC AAG TTC AAG   375
HUMAN    ... ... ... ... ... ... ... ... ... ... ... ... ... ... ... ... ... ... ... ... ... ... ... ... ...

135                               145
         Gln Ser Thr His Ser Ile Tyr Met Phe Asn Thr Ser Glu Leu Arg Glu Ala Val Pro Glu Pro Val Leu Leu
SIMIAN   CAG AGC ACA CAC AGC ATA TAT ATG TTC AAC ACA TCA GAG CTC CGA GAA GCA GTA CCT GAA CCT GTG TTG CTC   450
HUMAN    ..T ... ... ... ... ... ... ... ... ... ... ... ... ... ... ... ... ..G ... ... ... ..C ... ...

160                              170
         Ser Arg Ala Glu Leu Arg Leu Leu --- --- Arg Leu Lys Val Lys Leu Gln His Val Glu Leu Tyr Gln Lys Tyr
SIMIAN   TCC CGG GCA GAG CTC CGT CTG CTG --- --- AGG CTC AAG GTC AAA CTC GAG CAG CAT GTG GAG CTG TAC CAG AAA TAC   522
HUMAN    ... ... ... ... ... ... ... Arg AGG ... ... ... ... ... ... ... ... ... Asp ..C ... ... ... ... ...

185                              195
         Ser Asn Asn Ser Trp Arg Tyr Leu Ser Asn Arg Leu Leu Ala Pro Ser Asn Ser Pro Glu Trp Leu Ser Phe Asp
SIMIAN   AGC AAC AAT TCC TGG CGA TAC CTC AGC AAC CGG CTG CTG GCG CCC AGC AAC TCG CCG GAG TGG TTG TCT TTT GAT   597
HUMAN    ... ... ... ... ... ... ... ... ... ... ... ..A ... ... ..G ..A ... ... ... ... ... ..A ... ... ...

210                              220
         Val Thr Gly Val Val Arg Gln Trp Leu Ser Arg Gly Gly Glu Ile Glu Gly Phe Arg Leu Ser Ala His Cys Ser
SIMIAN   GTC ACC GGA GTT GTG CGG CAG TGG TTG AGC CGC GGA GGG GAA ATT GAG GGC TTT CGC CTT AGC GCC CAC TGC TCC   672
HUMAN    ... ... ... ... ... ... ... ... ... ... ... ..T ... ... ... ... ... ... ... ... ... ... ... ... ...
```

```
                                  Arg
          Cys Asp Ser Lys Asp Asn Thr Leu Gln Val Asp Ile Asn Gly Phe Thr Thr Gly Arg Arg Asp Leu Ala Thr
SIMIAN    TGT GAC AGC AAA GAT AAC ACA CTG CAA GTG GAC ATC AAC GGG TTC ACT ACC GGC CGA CGA GAC CTG GCC ACA    747
HUMAN     ... ... ... ... ... .GG ... ... ... ... ... ... ... ... ... ... ... ... ... ... ... ... ... ..G 235                                            245

Ile His Gly Met Asn Arg Pro Phe Leu Leu Met Ala Thr Pro Leu Glu Arg Ala Gln His Leu Gln Ser Ser
SIMIAN    ATT CAT GGC ATG AAC CGG CCT TTC CTC CTC ATG GCC ACC CCG CTG GAG AGG GCC CAA CAT CTG CAA AGC TCC    823
HUMAN     ... ... ... ... ... ... ... ... ... ... ... ... ... ... ... ... ... ... ... ..G ... ... ... ...

260                                            270

Arg His Arg Arg Ala Leu Asp Thr Asn Tyr Cys Phe Ser Ser Thr Glu Lys Asn Cys Cys Val Arg Gln Leu Tyr
SIMIAN    CGG CAC CGC CGA GCC CTG GAC ACC AAC TAC TGC TTC AGC TCC ACG GAG AAG AAC TGC TGC GTG CGG CAG CTG TAT    897
HUMAN     ... ... ... ... ... ... ... ... ... ..T ... ... ... ... ... ... ... ... ... ... ... ... ... ... ..C 285                                          295

Ile Asp Phe Arg Lys Asp Leu Gly Trp Lys Trp Ile His Glu Pro Lys Gly Tyr His Ala Asn Phe Cys Leu Gly
SIMIAN    ATT GAC TTC CGC AAG GAC CTC GGC TGG AAG TGG ATC CAC GAG CCC AAG GGC TAC CAT GCC AAC TTC TGC CTG GGG    972
HUMAN     ... ... ... ... ... ... ... ... ... ... ... ... ... ... ... ... ... ... ... ... ... ... ... ..C ...

310                                            320

Pro Cys Pro Tyr Ile Trp Ser Leu Asp Thr Gln Tyr Ser Lys Val Leu Ala Leu Tyr Asn Gln His Asn Pro Gly
SIMIAN    CCC TGT CCC TAC ATT TGG AGC CTG GAC ACG CAG TAC AGC AAG GTC CTG GCC CTG TAC AAC CAG CAT AAC CCG GGC    1047
HUMAN     ..C ... ... ... ... ... ... ... ... ... ... ... ... ... ... ... ... ... ... ... ... ... ... ... ...

```
                                         360                                         370
          Ala Ser Ala Ala Pro Cys Cys Val Pro Gln Ala Leu Glu Pro Ile Val Tyr Tyr Val Gly Arg Lys Pro
SIMIAN    GCC TCG GCG GCG CCC TGC TGC GTG CCG CAG GCC CTG GAG CCA CCC ATC GTG TAC TAC GTG GGC CGC AAG CCC  1122
HUMAN     ... ... ... ... ... ... ... ... ... ... ... ... ... ..G ... ... ... ... ... ... ... ... ...

385
          Lys Val Glu Gln Leu Ser Asn Met Ile Val Arg Ser Cys Lys Cys Ser
SIMIAN    AAG GTG GAG CAG CTG TCC AAC ATG ATC GTG CGC TCC TGA AAA TGC AGC  TGA  GGCCCCGCCCCCCGCCCCCACCCCCGGCAG 1204
HUMAN     ... ..G ... ... ... ... ... ... ... ... ... ... ... ... ..G ...       ...........................T....

SIMIAN    GCCCGGCCCCGCCCCCACCCCACCCCCGCTGTCTTGCCCTTGGGGGCTGTATTTAAGGACACCCGTGCCCCAAGCCCACCTGGGGCCCATTAAAGA  1300
HUMAN     .....A...G....C.........A..............
```

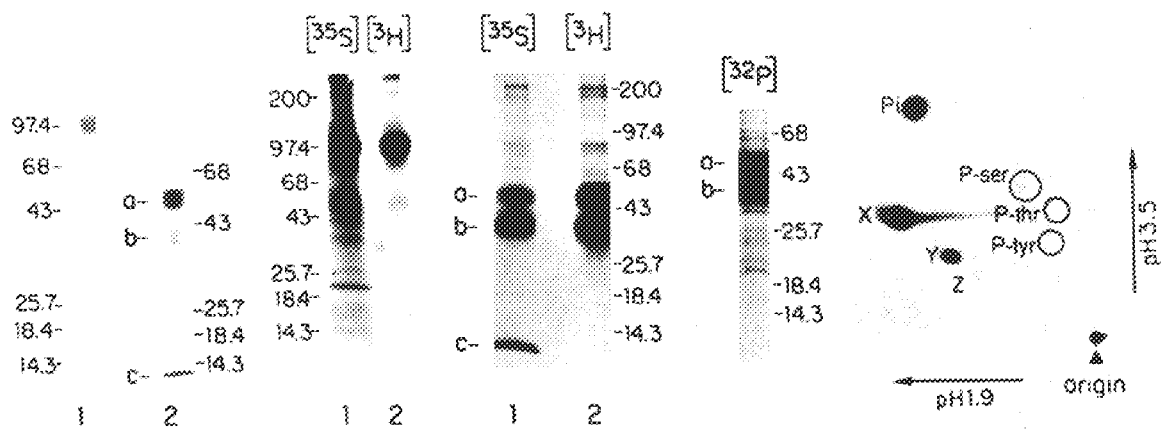

E(76-91)  A V L A L Y X̊ S T R D R V A G E

E(134-139)  F F X̊ T S E

T(174-180)  Y S X̊ N S W R

| MUTANT | OLIGONUCLEOTIDE |
|---|---|
| TGF-β1 S33 | ACTATCCACCAGCAAGACTAT |
| TGF-β1 S223 | TAGCGCCCACAGCTCCTGTGA |
| TGF-β1 S225 | CACTGCTCCTCTGACAGCAAA |
| TGF-β1 S223/225 | TAGCGCCCACAGCTCCTCTGACAGCAAA |

CLONING AND EXPRESSION OF SIMIAN TRANSFORMING GROWTH FACTOR β1

This application is a continuation of U.S. application Serial No. 07/353,728, filed May 17, 1989, now abandoned, which is a continuation-in-part of application Ser. No. 07/350,171, filed Apr. 17, 1989, now abandoned, which is a continuation-in-part of application Ser. No. 07/285,917, filed Dec. 16, 1988, now abandoned, which is a continuation-in-part of application Ser. No. 07/189,894, filed May 3, 1988, now abandoned, which is a continuation-in-part of application Ser. No. 07/147,842, filed Jan. 25, 1988, now abandoned, which is a continuation-in-part of application Ser. No. 07/055,662, filed May 29, 1987, now abandoned, each of which application is incorporated by reference herein in its entirety.

TABLE OF CONTENTS

Page
1. Introduction
2. Background of the Invention
3. Summary of the Invention
4. Description of the Figures
5. Description of the Invention
   - 5.1. Isolation or Generation of the Simian TGF-β1 Coding Region
   - 5.2. Construction of Expression Vectors Containing the TGF-β1 Coding Sequence
   - 5.3. Identification of Transfectants or Transformants Expressing the TGF-β1 Gene Product
   - 5.4. Initial Characterization of the TGF-β1 Gene Product
   - 5.5. The TGF-β1 Precursor: Cellular Processing, Structural Nature and Possible Function
   - 5.6. Interactions of TGF-β1 Precursor With the Insulin-Like Growth Factor-II/Mannose 6-Phosphate Receptor
   - 5.7. Biological Activity of TGF-β1
   - 5.8. Improved Method for Producing Mature TGF-β1.
6. Example: cDNA Cloning of TGF-β1 Precursor
   - 6.1. Materials and Methods
     - 6.1.1. Growth of Cells and RNA Extraction
     - 6.1.2. cDNA Library Construction and Screening
     - 6.1.3. Northern Blot Analysis
   - 6.2. Results
7. Example: Expression of TGF-β1
   - 7.1. Materials and Methods
     - 7.1.1. Cell Culture
     - 7.1.2. DNA Manipulations and Plasmid Constructions
     - 7.1.3. DNA Transfections
     - 7.1.4. Selection of Methotrexate Resistant Cells
     - 7.1.5. Quantitation of Beta TGF-1 Message Levels
     - 7.1.6. Growth Inhibition Assay
     - 7.1.7. Stimulation of Anchorage Independent Growth
     - 7.1.8. Peptide Synthesis and Production of Antibodies
     - 7.1.9. Immunoblotting
     - 7.1.10. Northern Blot Analysis
     - 7.1.11. Southern Blot Analysis
   - 7.2. Expression of rTGF-β1 in CHO Cells
   - 7.3. Detection of Secreted Bioactive Recombinant TGF-β1
   - 7.4. Acid Activation Optimizes Bioactivity of Secreted Recombinant TGF-β1
   - 7.5. Identification of Mature and Precursor Forms of rTGF-β1 in the Culture Medium of Transfectant TGF-β1-3 CHO Cells
     - 7.5.1. Identification of Mature rTGF-β1
     - 7.5.2. Identification of Precursor rTGF-β1
   - 7.6. Recombinant TGF-β1 Constitutes the Majority of the Secreted Proteins from TGF-β1-3/2000 Cells
8. Example: Characterization of the TGF-p1 Gene Product
   - 8.1. Glycosylation and Phosphorylation of the rTGF-β1 Precursor
   - 8.2. Purification of Biologically Active rTGF-β1
   - 8.3. Purification and Nature of rTGF-β1 Precursor
   - 8.4. Amino Terminal Sequence of rTGF-β1 Polypeptides
   - 8.5. Biological Activity In Vitro
   - 8.6. Biological Activity In Vivo
9. Example: Identification of Mannose-6-Phosphate In Two Asparagine-Linked Sugar Chains of rTGF-β1 Precursor
   - 9.1. Materials and Methods
     - 9.1.1. Materials
     - 9.1.2. Cell Culture
     - 9.1.3. Radiolabeling
     - 9.1.4. Polyacrylamide Gel Electrophoresis
     - 9.1.5. Acid Hydrolysis
     - 9.1.6. 5-Pyridylethylation
     - 9.1.7. Chemical and Enzymatic Cleavage
     - 9.1.8. Peptide Purification
     - 9.1.9. Amino Acid Sequence Analysis
     - 9.1.10 Binding Studies
   - 9.2. Results
10. Example: Expression of TGF-β1 Variants in COS Cells
    - 10.1. Materials and Methods
      - 10.1.1 Characterization of CNBr Peptide M(134–253)
      - 10.1.2 Construction of Expression Vectors Coding for TGF-β1$^2$ Variants and DNA Transfections
    - 10.2. Results
      - 10.2.1 Analysis of Proteins Encoded by TGF-β1 Coding Sequences
      - 10.2.2 TGF-p1 Precursor Residues CYS-223 and CYS-225 Form Interchain Di-sulfide Bonds
      - 10.2.3 Variant TGF-p1 Precursor Generate Biologically Active TGF-β1
      - 10.2.4 TGF-1 $S^{223/225}$ Variant Yields Biologically Active TGF-β1 Without Prior Acidification
11. Example: Interaction of TGF-β1 Precursor With Insulin-Like Growth Factor/Mannose 6-Phosphate Receptor
    - 11.1. Materials and Methods
      - 11.1.1. Materials
      - 11.1.2. Receptor Binding and International Studies
      - 11.1.3. Western Blot Analysis
    - 11.2. Results
      - 11.2.1. Recombinant TGF-β1 Precursor Binds to IGF-II/Man6P Receptors on Adipocytes and is Internalized
      - 11.2.2. Presence of Mannose 6-Phosphate on Latent TGF-β
12. Example Analysis of Functional Role of Carbohydrate on TGF-β1 Precursor
    - 12.1. Materials and Methods
      - 12.1.1. Materials
      - 12.1.2. Cell Culture
      - 12.1.3. Metabolic Labeling and Analysis of Secreted TGF-β
      - 12.1.4. Quantitation of TGF-β1 By SDS-Page
      - 12.1.5. Digestion With Glycosylational Trimming Enzymes
      - 12.1.6. Digestion of SacII Deletion Mutant of TGF-β1 and Insertion Into CDM8 Vector
      - 12.1.7. Transient Expression In COS Cells 12.2. Results
    12.2.1. Tunicamycin Inhibits Secretion of Recombinant TGF-β1 from Transfected CHO Cells
    12.2.2. Time Course for CHO Transfectant Secretion of TGF-β1
    12.2.3. Inhibitors of Glycosylation or Glycosylational Processing Affect Level of Secreted rTGF-β1
    12.2.4. Structure of TGF-β1 Oligosaccharide Side Chains
    12.2.5. Mannose 6-Phosphorylation of TGF-β1 Precursor Polypeptides Released From Inhibitor-Treated CHO Cells
    12.2.6. Deletion Mutagenesis Studies
    12.2.7. Intracellular Proteolytic Processing Within Acidic Vesicles
13. Example: Gamma Interferon-Induced Activation Of Latent TFG-β By Human Macrophages
    13.1. Materials And Methods
        13.1.1. Purification Of Latent TFG-β
        13.1.2. Activation Of Latent TFG-β1 Assay
    13.2. Results
14. Deposit of Microorganisms

1. INTRODUCTION

The present invention relates to the cloning, expression, and uses of simian transforming growth factor-β1 (rTGF-β1). The product of the invention has a bioactivity equivalent to that of authentic mature human TGF-β1.

2. BACKGROUND OF THE INVENTION

The transforming growth factor (TGF) family of growth modulating peptides consists of two structurally and functionally dissimilar molecules, TGF-alpha and TGF-beta. TGF-alpha, synthesized and released by retroviral transformed rodent cell lines (DeLarco et al., 1978, Proc. Natl. Acad. Sci. USA 75:4001–4005; Twardzik et al., 1982, Science 216:894–897) and some human tumor cell lines (Todaro et al., 1980, Proc. Natl. Acad. Sci. USA 77:5258–5262), competes with epidermal growth factor (EGF) for binding to the EGF receptor (Todaro et al., 1976, Nature 264, 26–29) and stimulates tyrosine specific phosphorylation of the EGF receptor (Reynolds et al., 1981, Nature 292:259–262). A potent mitogen for cells of mesenchymal origin, the mature form of TGF-alpha comprises 50 amino acid residues, shares sequence homology with both rodent and human EGF, (Marquardt et al., 1983, Proc. Natl. Acad. Sci. USA 80:4684–4688) and is cleaved from a 159 amino acid precursor (Derynck et al., 1984, Cell 38:287–297; Lee et al., 1985, Nature 313:489–491).

Very recently a protein isolated from bovine demineralized bone has been identified as being related to TGF-β (Seyedin et al., 1987, J. Biol. Chem. 262:1946–1949). The protein has also been isolated from porcine platelets (Cheifetz et al., 1987, Cell 48:409–415), a human prostatic adenocarcinoma cell line PC-3 (Ikeda et al., 1987, Biochemistry 26:2406–2410), and a human glioblastoma cell line (Wrann et al., 1987, EMBO 6:1633–1636). Partial amino acid sequence of this protein indicated that it was homologous to TGF-β and has been termed TGF-β2. The human (Derynck et al., 1985, Nature 316:701–705), mouse (Derynck et al., 1986, J. Biol. Chem. 261:4377–4379) and simian (Sharples et al., 1987, DNA 6:239–244) TGF-β1 described previously has been and is hereinafter termed TGF-β1.

TGF-β1, a disulfide linked homodimer (9 cysteine residues per chain) contains two identical subunits (112 amino acid residues per subunit) and utilizes a receptor distinct from either TGF-alpha or EGF (Frolik et al., 1984, J. Biol. Chem. 260:10995–11000; Tucker et al., 1984, Proc. Natl. Acad. Sci. USA 81:6757–6761). This potent modulator of cell behavior is synthesized by a variety of normal and transformed cells in culture (Roberts et al., 1981, Proc. Natl. Acad. Sci. USA 78:5339–5343) and has been purified from various sources including placenta (Frolik et al., 1983, Proc. Natl. Acad. Sci. USA 80:3676–3680), kidney (Roberts et al., 1983, Biochemistry 22:5692–5698), urine (Twardzik et al., 1985, J. Cell. Biochem. 28:289–297) and blood platelets (Childs et al., 1982, Proc. Natl. Acad. Sci. USA 79:5312–5316). TGF-β1 requires either TGF-alpha or EGF to promote the anchorage independent growth of normal rat kidney (NRK) fibroblasts; however the requirement for TGF-alpha or EGF is less stringent to promote anchorage independent growth of AKR-2, a murine indicator cell (Tucker et al., 1983, Cancer Res. 43:1581–1586). In contrast to stimulating cell growth, TGF-β1 from human platelets and a functionally related polypeptide with nearly identical biochemical properties isolated from African Green monkey cells (BSC-1) has also been shown to exhibit growth inhibitory effects on some cells in culture (Tucker et al., 1984, Science 226:705–707). Both the bifunctionality of TGF-β1 (inhibition/stimulation) and its apparent ubiquitous distribution suggests it may play a key role in regulating the growth and behavior of mammalian cells.

The amino acid sequence deduced from cDNAs encoding the TGF-β1 precursor of human (Derynck et al., 1985, Nature 316:701–705) and mouse (Derynck et al., 1986, J. Biol. Chem. 261:4377–4379) origin indicate a high degree of homology not only in the area of the mature TGF-β1 sequence but also in the amino terminal precursor region.

Although the gene for human TGF-β1 has been identified and sequenced, the cloning and expression of large quantities of active TGF-β1 has not heretofore been reported. A number of factors may be responsible for the difficulty in expressing an active TGF-β1, one of which may involve the complexity of the tertiary structure of the molecule. Mature TGF-β1 has a number of interchain and intrachain disulfide bonds, the formation of which requires proper processing during expression of the gene product. Moreover, the mature form of TGF-β1 derived from a glycosylated larger precursor molecule. Correct glycosylation patterns of the precursor may be required for correct processing, secretion and cleavage of the mature form of TGF-β1. Thus, the cloning and expression of a gene having the correct coding sequence in an inappropriate expression vector/host cell system may result in the expression of a product having the proper primary structure (i.e., amino acid sequence) but incorrect secondary and tertiary structures (i.e., folding and conformation) resulting in an inactive molecule. Thus, the production of large quantities of TGF-β1 has been hampered.

3. SUMMARY OF THE INVENTION

The present invention relates to the production of large quantities of simian TGF-β1 by eucaryotic host cells transfected with recombinant DNA vectors containing the simian TGF-β1 coding sequence controlled by expression regulatory elements. A cDNA clone coding for simian TGF-β1 precursor was obtained from a cDNA library made from an African Green Monkey cell line, BSC-40. The deduced amino acid sequence of the mature simian TGF-β1 shows 100% homology with that of the mature human TGF-β1. Strong sequence homology was found between the precursor regions of the human and simian proteins with only five amino acid changes out of 278 residues. The simian (and murine) precursor sequence was found to code for one less amino acid residue than the human.

Expression vectors were constructed which contain the entire coding sequence for the simian TGF-β1 placed under the control of SV40 expression elements. They were used to transfect Chinese Hamster Ovary cells (CHO cells). The resulting CHO transfectants produce and secrete both mature rTGF-β1 which has a biological activity comparable to authentic TGF-β1 as well as the precursor form of rTGF-β1 which also has a buiological activity.

4. DESCRIPTION OF THE FIGURES

FIG. 1. Nucleotide sequence of simian TGF-β1 cDNA and deduced amino acid sequence. The 1600 bp insert of pTGF-β1-2 was subcloned into the M13mp18 and M13mp19 cloning vectors (Yanisch-Perron et al., 1985 Gene 33:103–119) and both strands were sequenced using the dideoxy chain-termination method (Sanger et al., 1977 Proc. Natl. Acad. Sci. USA 74:5463–5467). The deduced amino acid sequence of simian TGF-β1 is presented directly above the cDNA sequence. The human TGF-β1 nucleotide sequence is aligned with and presented directly below the simian cDNA sequence; dots indicate homologous nucleotide residues within the sequences. Amino acid differences between the human and simian proteins are indicated in the top line. The mature TGF-β1 sequence is boxed and the signal peptide is overlined.

FIG. 2. Northern blot analysis of RNA from a human (MCF-7) and simian (BSC-40) cell line using a simian TGF-β1 cDNA probe. Polyadenylated RNA was isolated from MCF-7 cells and BSC-40 cells as described (Purchio et al., 1979, J. Virol. 29:763–769), fractionated on a 1% agarose-formaldehyde gel (12), transferred to a nylon membrane (Hybond, Amersham) and hybridized to [$^{32}$p]- labeled pTGF-β1-2 probe. Lane 1, human MCF-7 RNA (5 ug); lane 2, simian BSC-40 RNA (5 ug). 28S and 18S indicate the position of migration of 28S and 18S ribosomal RNAs.

Figure 3:
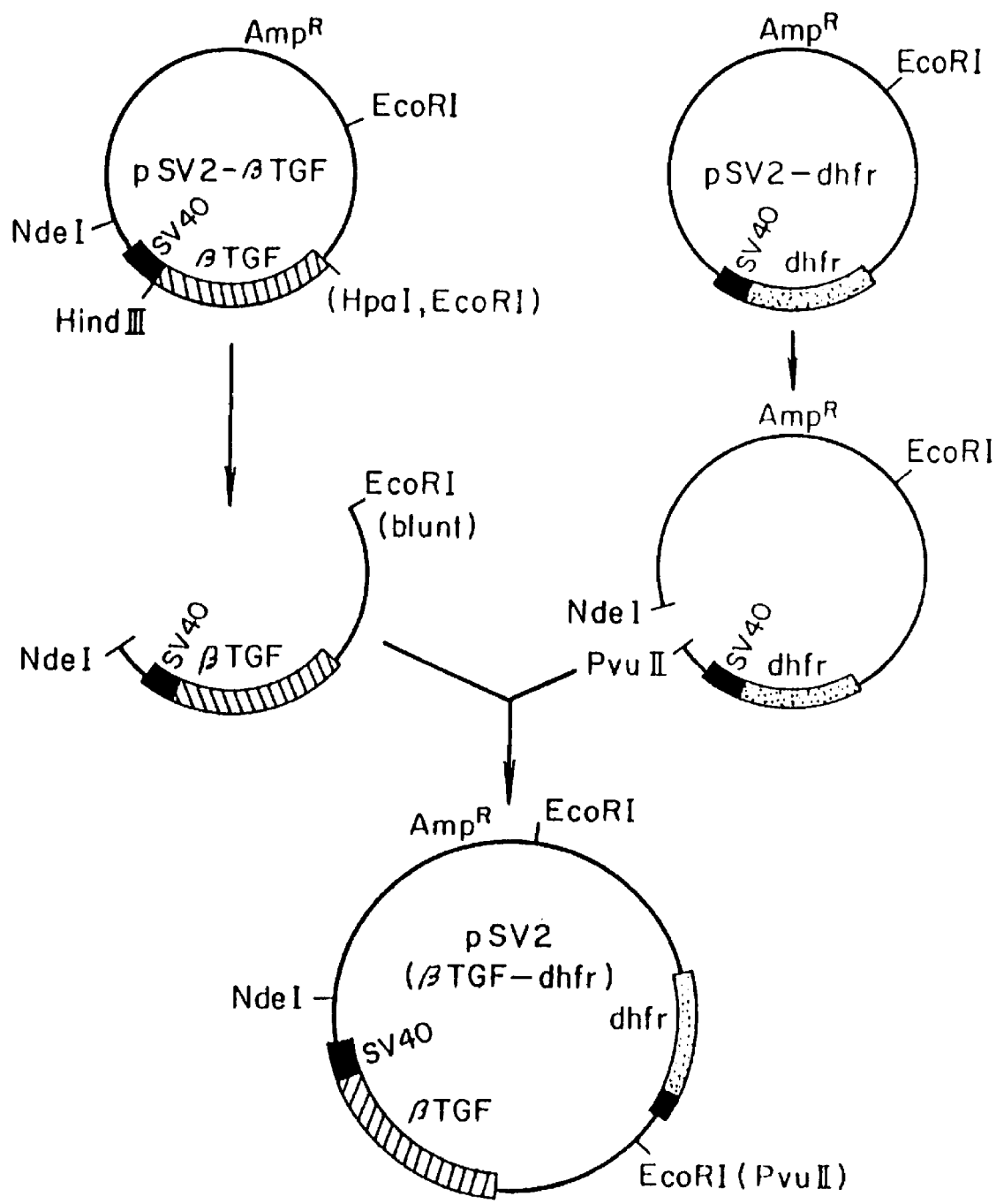

FIG. 3. Construction of the amplifiable expression plasmid pSV2 (TGF-β1-dhfr). The details of the construction are outlined in Section 7 infra. The final recombinant plasmid contained the TGF-β1 cDNA encoding the entire precursor form of TGF-β1 and the mouse dhfr cDNA in tandem.

Initiation of transcription of TGF-β1 and dhfr mRNAs are driven by the SV40 early promoter. Polyadenylation signals and other sequences responsible for correct RNA processing are supplied by 3' SV40 sequences. Restriction sites in parenthesis are lost during construction of the amplifiable expression plasmid.

Figure 4A:
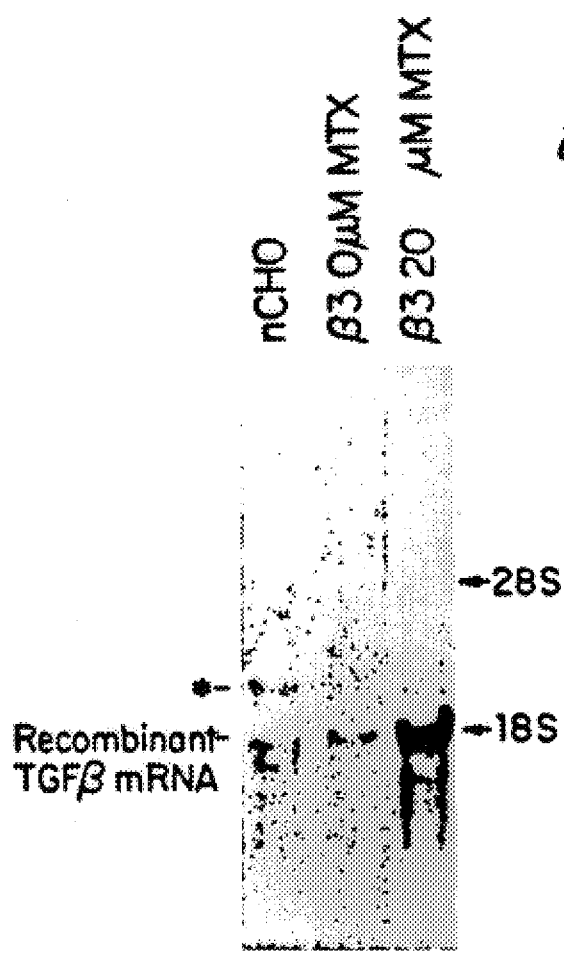
Figure 4B:
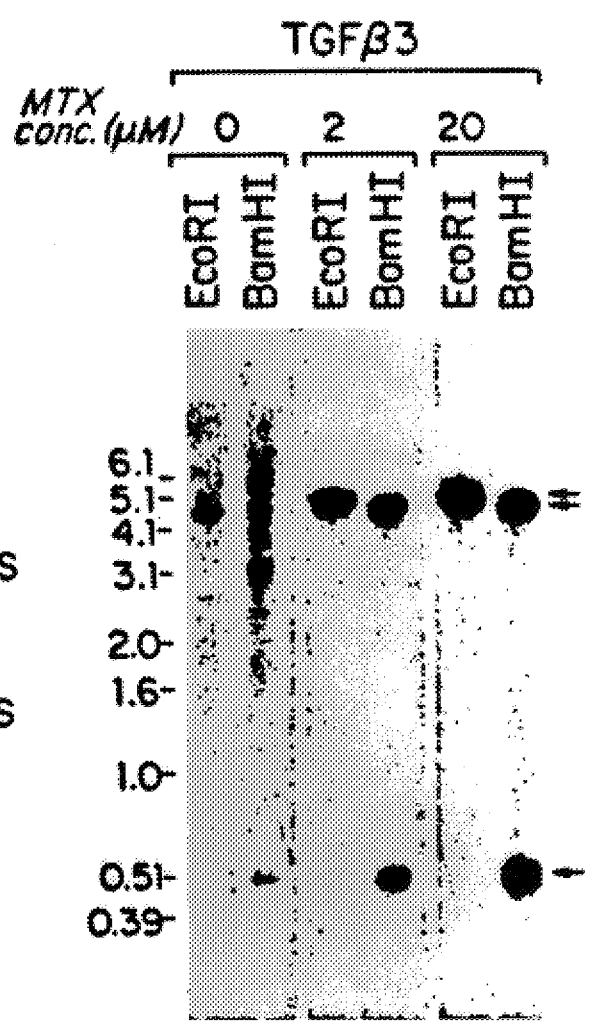

FIGS. 4A and 4B. Detection of TGF-β1 nucleic acid sequences in the CHO cells at various stages of MTX selection. FIG. 4A: Northern blot analysis for detection of TGF-β1 mRNA sequences. Poly (A)+ containing mRNA (5 ug) was fractionated on a 1% agarose-formaldehyde gel, blotted onto Hybond N membranes (Amersham) and probed with the radiolabeled TGF-β1 DNA as described in Materials and Methods. The lane containing the nontransfected CHO mRNA was exposed for 48 hours to reveal endogenous levels of the 2.5 Kb TGF-β1 message. Lanes containing mRNA from TGF-β1-3 cells were exposed 5 minutes. Ribosomal markers are shown to the right. FIG. 4B: Southern blot analysis of genomic DNA from the TGF-β1-3 CHO cell transfectants at various stages of MTX selection. High-molecular weight DNA from the TGF-β1-3 transfectants was digested with BamHI or EcoRI and 20 ug was fractionated onto a 1% agarose gel. The DNA was transferred to Hybond N (Amersham) membranes and probed with the nick-translated TGF-β1 DNA. Exposure time was 30 hours for TGF-β1-3-0 cells and 10 hours for TGF-β1-3-200 and 2000 cells. DNA size markers are indicated at the left of the figure. Arrows denote the sizes of DNA predicted to hybridize to the TGF-β1 probe.

Figure 5A:
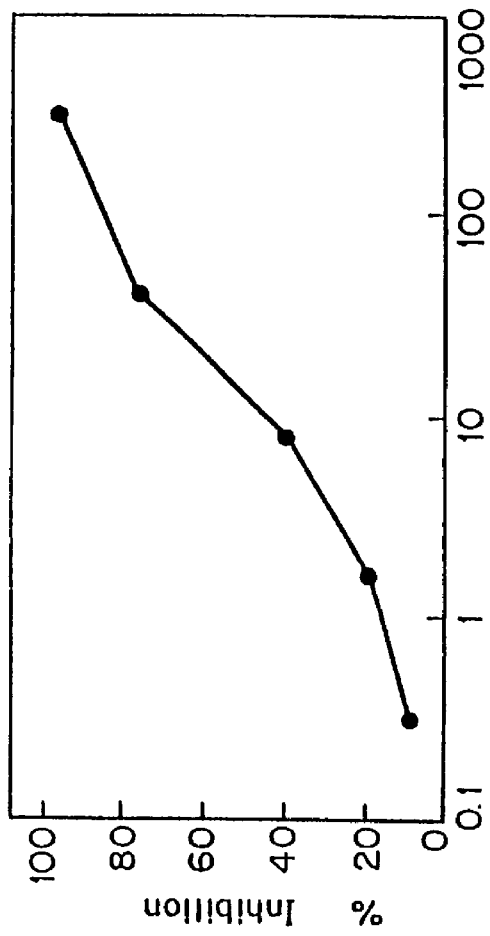
Figure 5B:
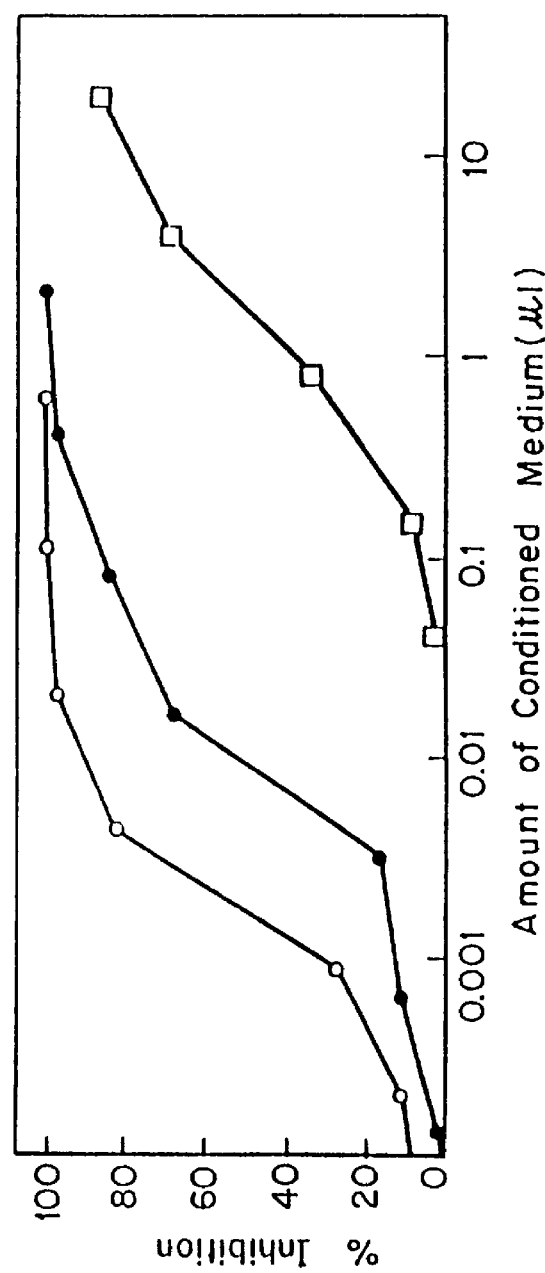

FIGS. 5A and 5B. Growth inhibition assay of CCL-64 mink lung epithelial cells with recombinant or natural β1-TGF. FIG. 5A: Growth inhibition assay employing natural TGF-β1 purified from bovine spleen; 50% inhibition is typically attained using 8–12 picograms of TGF-β1. FIG. 5B: Serum free supernatants were collected from confluent monolayers of the TGF-β1-3 transfectant at various stages of amplification. The media was dialyzed extensively against 0.2M acetic acid and assayed for growth inhibition as described in Section 7.1.6 infra. The results displayed are normalized for 1×10$^7$ cells per 5 ml collection.———, unamplified TGF-β1-3 cells; ●———● TGF-β1-3 cells adapted to 20 μM 2 μM methotrexate; ○———○ TGF-β1-3 cells adapted to 20 μM methotrexate.

Figure 6:
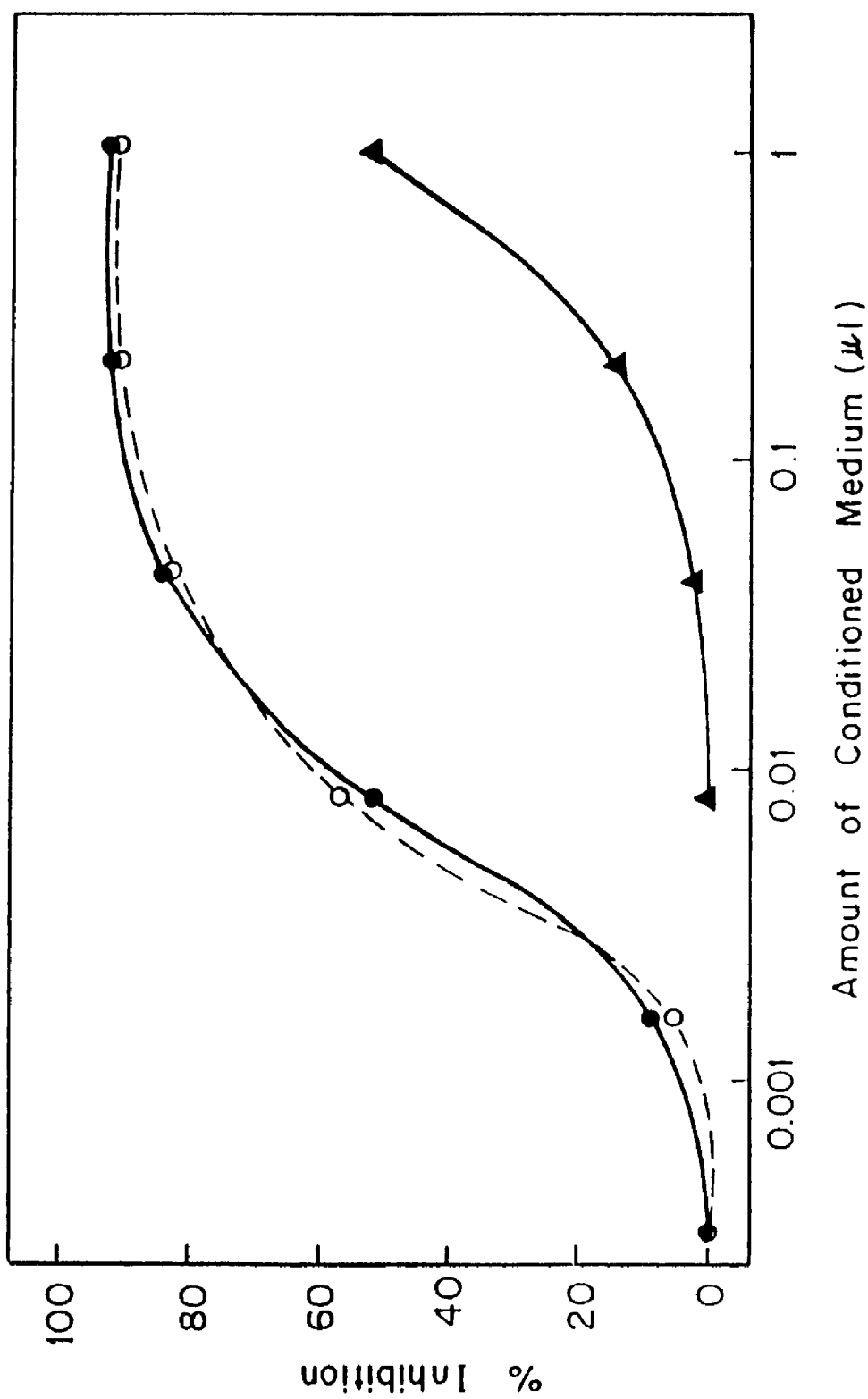

FIG. 6. Acid activation of recombinant TGF-β1. A 24 hour collection of serum free supernatants from TGF-β1-3/2000 cells was made. Equal portions were then dialyzed against 0.2M acetic acid or 50 mM NH$_4$HCO$_3$ (pH 7.0). As a control, supernatant first dialyzed versus 50 mM NH$_4$HCO$_3$ was then dialyzed against 0.2M acetic acid. A dose response bioactivity curve of the differentially processed material is shown. ▲———▲, supernatant dialyzed against NH$_4$HCO$_3$. ●———●, supernatant dialyzed against 0.2M acetic acid. ○———○, NH$_4$HCO$_3$ treated material further dialyzed versus 0.2 acetic acid.

Figure 7:
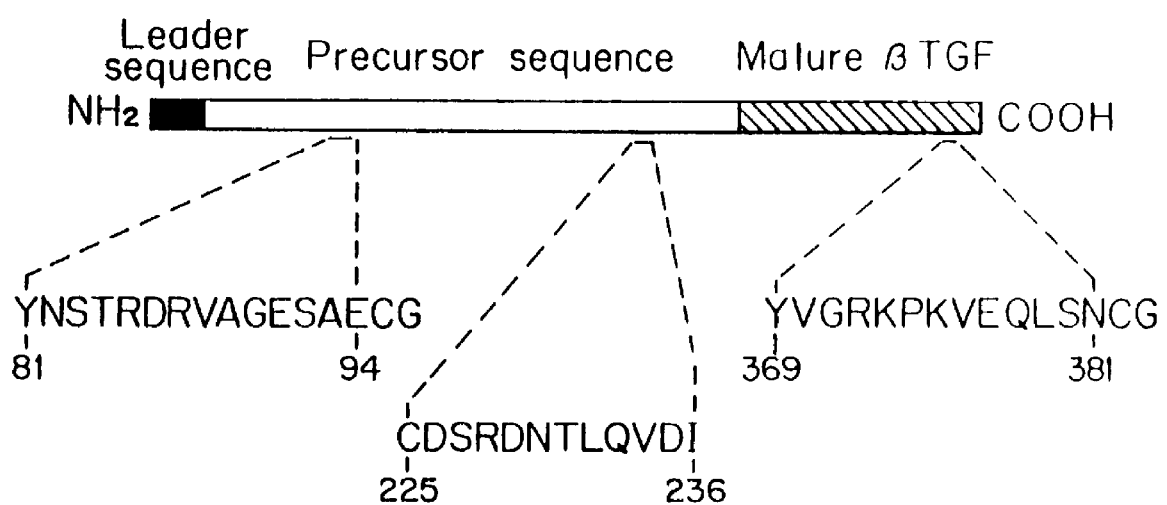

FIG. 7. Line diagram illustrating the structural features of the rTGF-β1 protein and indicating the peptide regions used for the generation of site specific anti-peptide antisera. The one-letter code for amino acids is used: A (alanine), C (cysteine), D (aspartic acid), E (glutamic acid), F (Phenylalanine), G (Glycine), H (histidine), I (Isoleucine), K (lysine), L (leucine), M (methionine), N (asparagine), P (proline), Q (glutamine), R (arginine), S (serine), T (threonine), V (valine), W (tryptophan), Y (tyrosine). Functionally important domains of TGF-β1 are identified: leader sequence, precursor sequences, and mature TGF-β1.

Figure 8A:
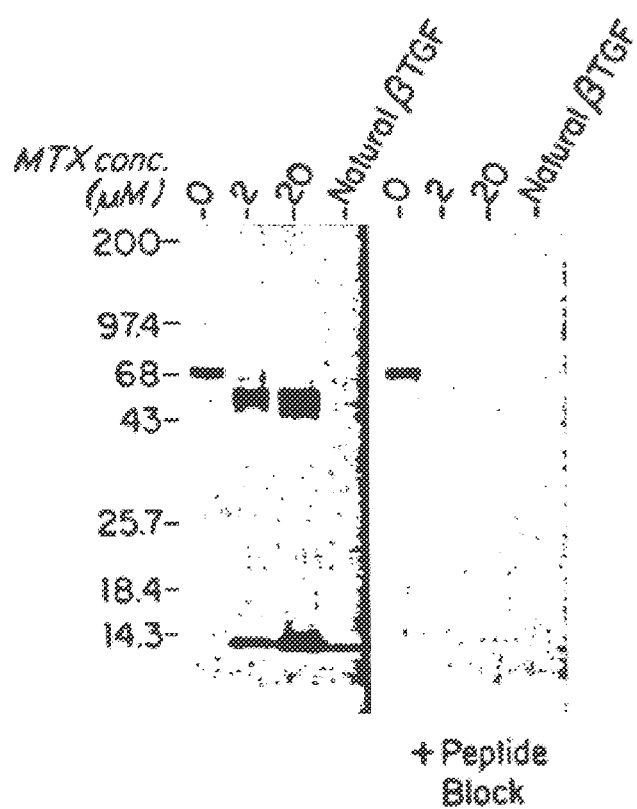
Figure 8B:
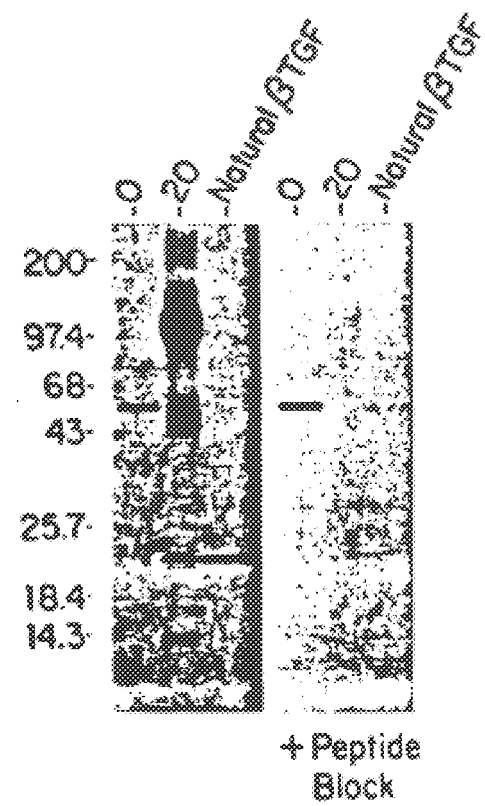

FIGS. 8A and 8B. Identification of recombinant TGF-β1 in the conditioned media of TGF-β1-3 cells by immunoblotting. Serum free supernatants were collected from confluent cultures of cells and dialyzed extensively against 0.2M acetic acid. After lyophilization, the material was solubilized in SDS-sample buffer, the equivalent of 2×10$^5$ cells fractionated on SDS-polyacrylamide gels, and immunoreactive TGF-β1 proteins were detected by immunoblotting. Anti-TGF-β1-$_{369-381}$ was utilized for the immunoblots. For the peptide blocking experiment, 50 ug/ml of peptide$_{369-381}$ was added to the antibody prior to the immunoblot. FIG. 8A: Immunoblot of material collected in supernatants from TGF-β1-3 adapted to 0, 2, or 20 μM methotrexate and fractionated on SDS polyacrylamide gels under reducing conditions. Natural bovine spleen TGF-β1 (100 ng) was included for comparison. FIG. 8B: Supernatants were fractionated under non-reducing reducing conditions. Bovine spleen TGF-β1 (250 ng) was included.

Figures 9A, 9B:
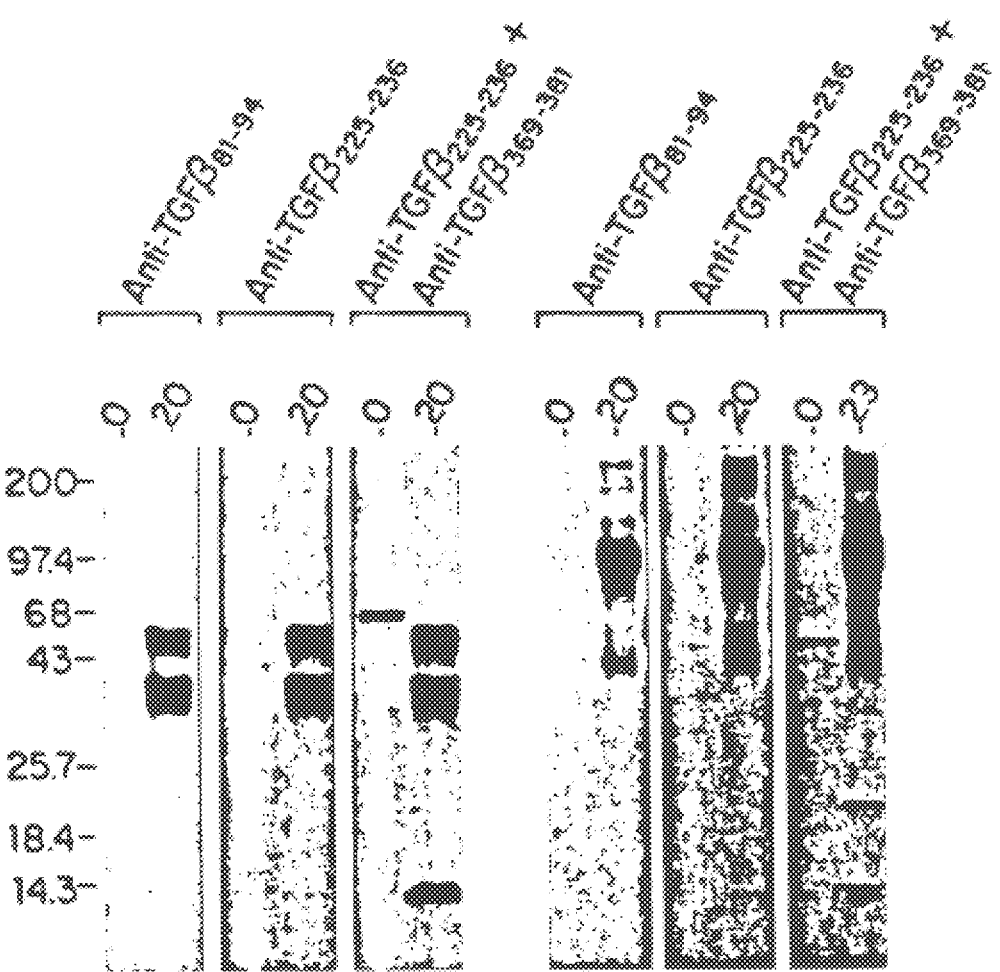

FIGS. 9A and 9B. Immunoblot of secreted recombinant TGF-β1 produced by TGF-β1-3 cells probed with anti-TGF-β1$_{81-94}$ and anti-TGF-β1$_{225-236}$. Supernatants were collected, processed as described in FIGS. 8A and 8B and fractionated on gradient SDS-polyacrylamide gels. FIG. 9A: Immunoblot of supernatants fractionated on reducing SDS-polyacrylamide gels. An immunoblot performed with a mixture of precursor-specific and TGF-β1-specific antibodies is shown in the last panel to show the three distinct forms of recombinant material. FIG. 9B: Immunoblot of supernatants fractionated on SDS-polyacrylamide gels under non-reducing conditions. A mixture of precursor-specific and TGF-β1 specific antibodies is shown in the last panel.

Figure 10:

FIG. 10. Detection of mature and precursor forms of rTGF-β1 in total secreted proteins of TGF-β1-3/0 and TGF-β1-3/2000 cells. Cells grown to confluency on 60 mm round tissue culture dishes were labeled in 3 ml of DMEM lacking methionine, cysteine and fetal bovine serum and containing 100 uci/ml of $^{35}$S-methionine and $^{35}$S-cysteine. After 18 hours, the serum-free labeled supernatant was collected, clarified, and fractionated on reducing 7.5–17.5% SDS-polyacrylamide gels. Following electrophoresis, the gel was processed with En$^3$Hance and autoradiographed. The results show an 8 hour exposure using 3 ul of the labeled supernatant.

Figure 11A:
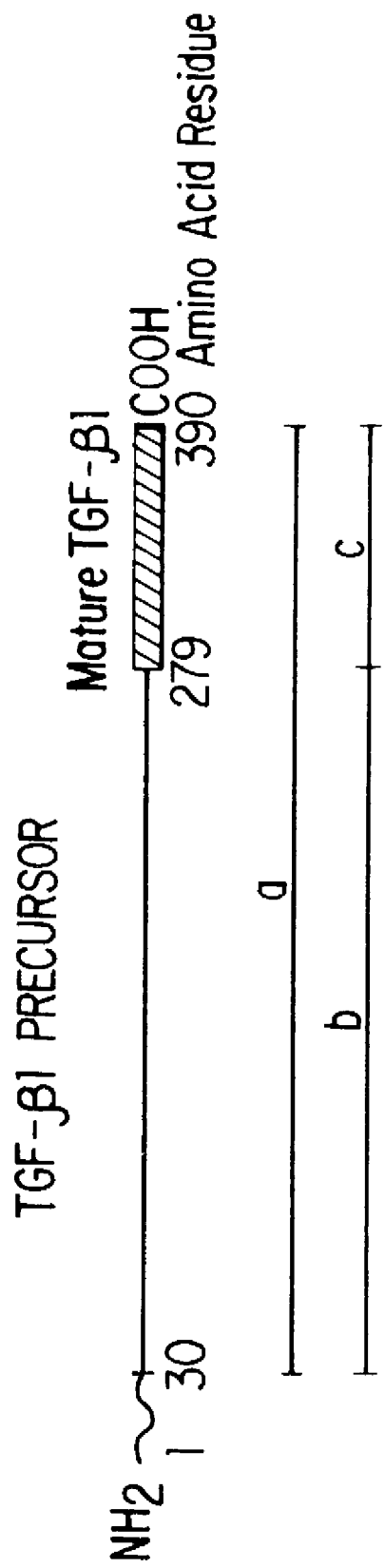

FIGS. 11A–11F. Detection of TGF-β1 related proteins secreted by TGFβ3-2000 cells. FIG. 11A: Line diagram of TGF-β1 precursor. See text for discussion. FIG. 11B: TGFβ3-2000 cells were grown to confluency in 100 mm dishes as described previously (Gentry et al., 1987, Mol. Cell. Biol. 7:3418–3427). Serum-free supernatants (5 mL) were collected, dialyzed against 0.2M acetic acid and 0.5 ml, samples were lyophylized and immunoblotted as described (Gentry et al., 1987, Mol. Cell. Biol. 7:3418–3427) using a pool of antipeptide antibodies against amino acid residues 369–381 (Anti-TGFβ$_{369-381}$) and 81–94 (anti-TGBβ$_{81-94}$): lane 1, non-reduced sample; lane 2, reduced sample. The numbers on the left (lane 1) and right (lane 2) indicate the position of molecular weight standards in kilodaltons. FIG. 11C: TGFβ3-2000 cells were grown to confluency in 60 mm tissue culture dishes and pulsed in serum-free medium (3 mL) lacking methionine and cysteine and containing 100–200 µCi/mL of [$^{35}$S]-cysteine and [$^{35}$S]-methionine for 15 min. Cells were then chased for 4 hours in serum-free medium containing methionine and cysteine and a 10 µl sample was analyzed on a 7.5%–15% polyacrylamide-SDS gradient gel as described (Laemmli, 1970, Nature 227:680–685) under non-reducing conditions (lane 1). A second dish of cells was labeled for 24 hours in serum-free medium containing 200 µCi/mL [$^3$H]-glucosamine and the cell free supernatant was dialyzed for 48 hours against 0.2M acetic acid. Two hundred microliters of this material was lyophylized and analyzed on a 7.5%–15% polyacrylamide-SDS gradient gel under non-reducing conditions. The gel was fluorographed and exposed for autoradiography using Cronx-4 X-ray film (DuPont). FIG. 11D: Same as FIG. 11C except samples were run under reducing conditions. FIG. 11E: TGFβ3-2000 cells were labeled with 1 m Ci/mL of [$^{32}$P]-orthophosphate in serum and phosphate free medium. Cell free supernatants were treated as described above, fractionated on a 15% polyacrylamide-SDS gel under reducing conditions and the gel was autoradiographed. FIG. 11F: [$^{32}$P]-labeled precursor was purified by two cycles of polyacrylamide-SDS gel electrophoresis and hydrolyzed for 1 hour at 95° C. in 6M HCl (Cooper et al., 1983, Meth. Enzymol. 99:387–402). The digestion products were separated by electrophoresis at ph 1.9 and at ph 3.5, and detected by autoradiography. Internal standards (P-ser, P-thr, p-tyr) were detected with ninhydrin.

Figures 12A, 12B:
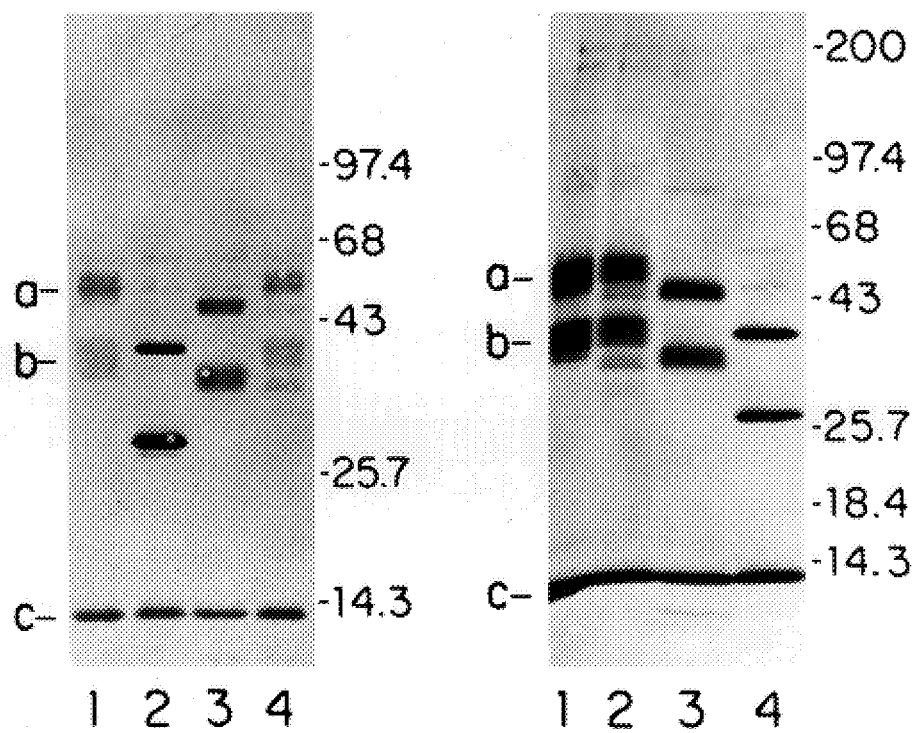

FIGS. 12A and 12B. Digestion of serum-free supernatants from TGβ3-2000 cells with various glycolytic enzymes. FIG. 12A: TGFβ3-2000 cells were grown to confluence and incubated for 24 hours in serum-free medium. The medium was dialyzed against 0.2M acetic acid, lyophylized, and samples were treated with neuraminidase (0.25 units/mL, lane 3), N-glycanase (20 units/mL, lane 2) or endoglycosidase H (0.2 units/mL, lane 4). The digests were fractionated by SDS-polyacrylamide gel electrophoresis under reducing conditions and analyzed by immunoblotting as described in the legend to FIG. 11. Lane 1 contains an untreated sample. FIG. 12B: Serum-free supernatants from TGFβ3-2000 cells were labeled with [$^{35}$S]-methionine and [$^{35}$S]-cysteine as described in the legend to FIG. 1 and digested as above with endoglycosidase H (lane 2), neuraminidase (lane 3) and N-glycanase (lane 4). Lane 1 contains an untreated sample. Digests were fractionated by SDS-polyacrylamide gel electrophoresis under reducing conditions and the gels were autoradiographed. N-glycanase was purchased from Genzyme (Boston, Mass.) and endoglycosidase H and neuraminidase were from Calbiochem (La Jolla, Calif.): buffer conditions were as recommended by the manufacturer.

Figures 13A, 13B:
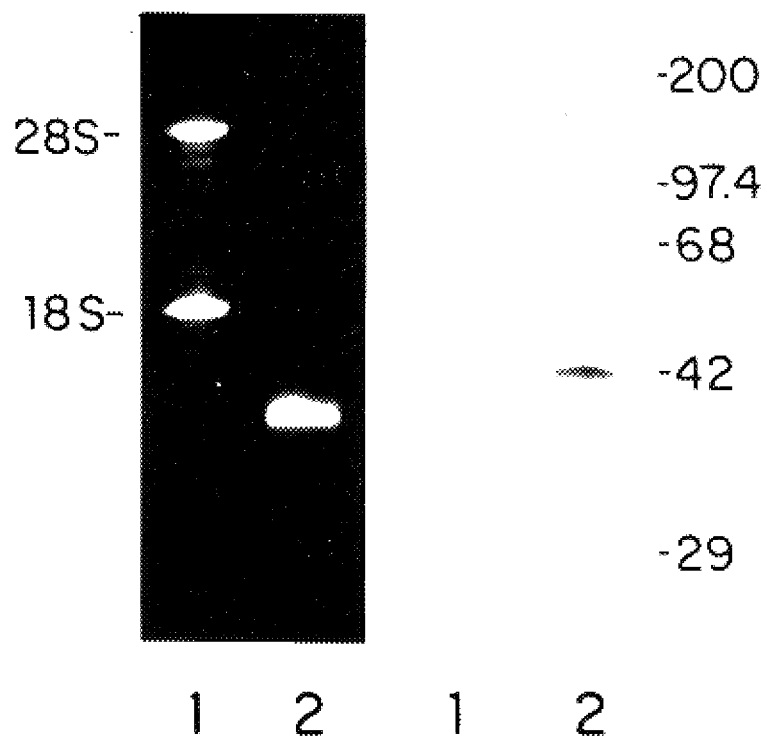

FIGS. 13A and 13B. Cell-free translation of TGF-β1 specific transcripts. FIG. 13A: A 1350 base pair Pst I-Eco R fragment containing the entire coding region of TGF-β1 (3) was subcloned into pSP64 (Pharmacia) and 5 µg of linearized plasmid was transcribed with SP6 polymerase (Kreig and Melton, 1984, Nucleic Acids Res. 18:7057–7070) purchased from Bethesda Research Labs (Baltimore, Md.) using ionic conditions described previously (Pelham and Jackson, 1976, Eur. J. Biochem. 67:247–251). The reaction was digested with DNase, extracted twice with phenol: chloroform: isoamylalcohol (24:24:1) and ethanol precipitated. The RNA was dissolved in 50 µl of H$_2$O and 10 µl (lane 2) was fractionated in a 1% agarose-urea gel as described (Purchio et al., 1980, J. Virol. 35:629–639). Lane 1 contains reticulocyte ribosomal RNA markers. The gel was stained with ethidium bromide, illuminated with UV light and photographed. FIG. 13B: The RNA described above was treated for 10 minutes at 22° C. for 10 mM methyl mercury, adjusted to 20 mM 2-mercaptoethanol and 1 µg was translated in a message-dependent reticulocyte cell-free translation system (Purchio et al., 1983, J. Virol. 48:320–324) in a total volume of 50 µl using [$^{35}$S]-methionine and ionic conditions described previously (Sharples et al., 1987, DNA 6:239–244). The reactions were fractionated on a 10% polyacrylamide-SDS gel (Laemmli, 1970, Nature 227:680–685); the gel was fluorographed and exposed to Cronex-4 X-ray film. Lane 1, no added RNA; lane 2, 1 µg TGF-β1 RNA.

Figure 14:
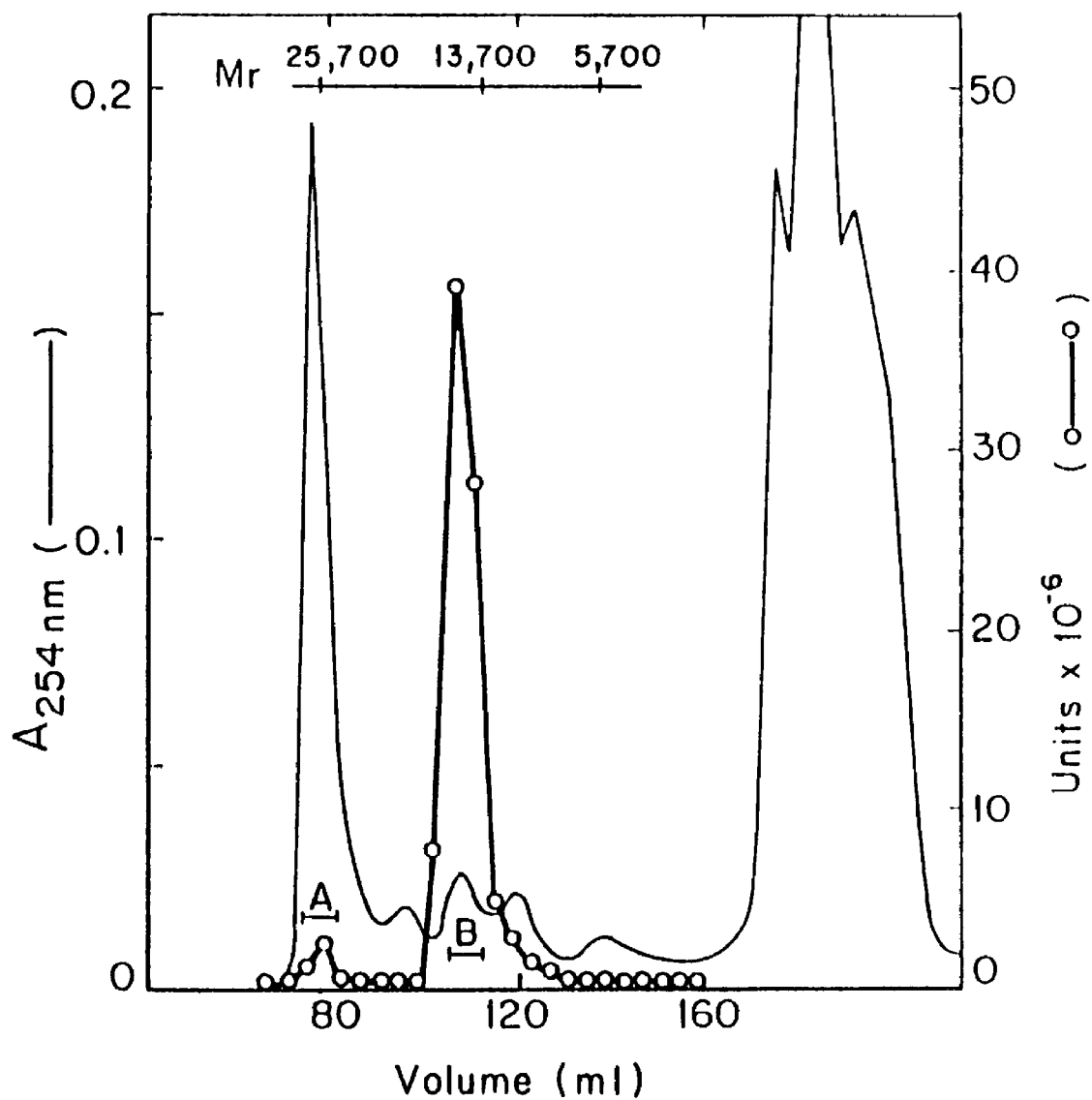

FIG. 14. Gel permeation chromatography on a Bio-Sil TSK-250 column (21.5×600 mm) of 20 mg protein after ammonium sulfate precipitation of 500 mL serum-free supernatant from TGF-β-3-2000 cells. The column was equilibrated with 0.1% TFA in water containing 40% (v/v) acetonitrile at 2 mL/min, at 22° C.; 4 mL fractions were collected. Aliquots of the indicated fractions were assayed for growth-inhibitory activity on mink lung epithelial cells (-○-). The solid line gives the protein absorbance at 254 nm. The following proteins were used as markers: α-chymotrypsinogen (Mr 25,700), bovine pancreatic ribonuclease A (Mr 13,700), and insulin (Mr 5,700).

Figure 15:
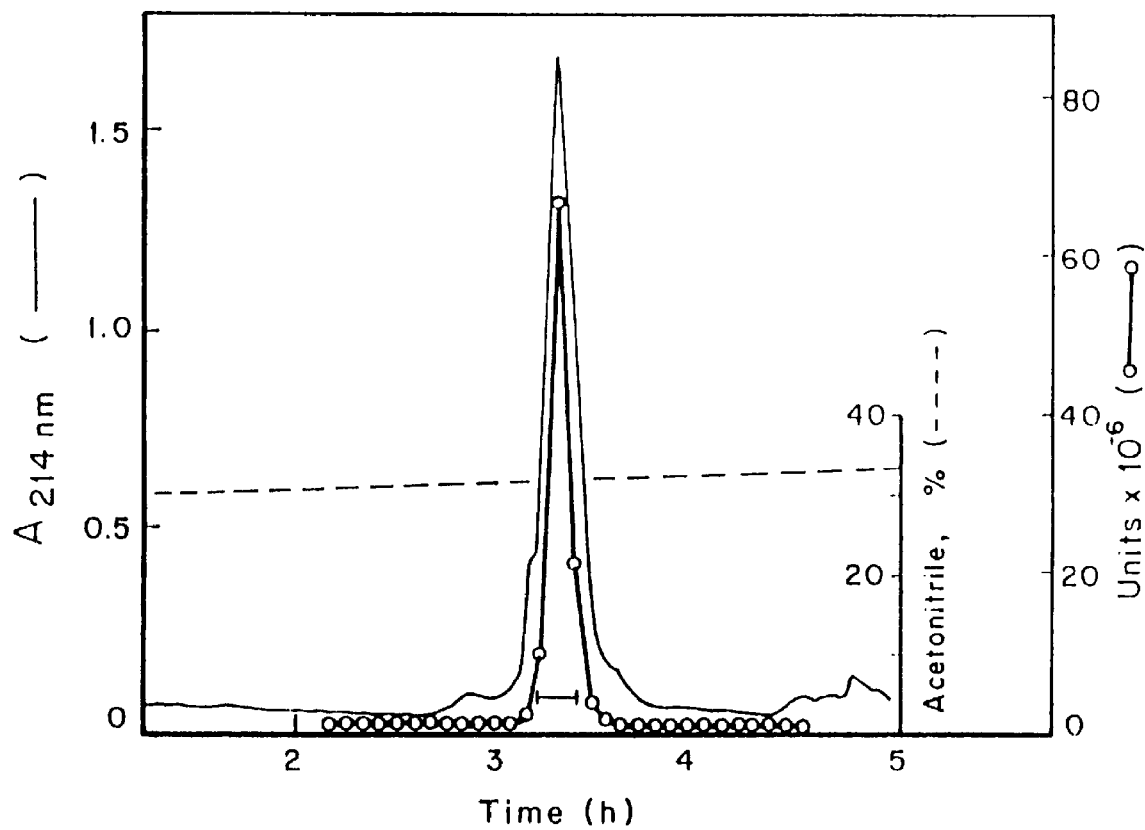

FIG. 15. Purification of rTGF-β1 by reversed-phase HPLC. Elution pattern of 0.65 mg protein from gel permeation chromatography purified TGF-β1 (FIG. 2, pool B) on a µBondpak C$_{18}$ column (10-µm particle size, 3.9×300 mm). Elution was achieved with a linear 10-min gradient of 0.05% TFA in water to 30% acetonitrile in 0.045% TFA, and a 10-min gradient of 36–60% acetonitrile in 0.045% TFA. The column was operated at a flow rate of 0.2 mL/min, at 22° C.

Aliquots of the indicated fractions were assayed for growth-inhibitory activity on mink lung epithelial cells (-○-). The horizontal bar indicates pooled rTGF-β1. UV-absorbing material was continuously monitored at 214 nm (———); the dashed line (----) denotes the concentration of acetonitrile.

Figures 16A, 16B:
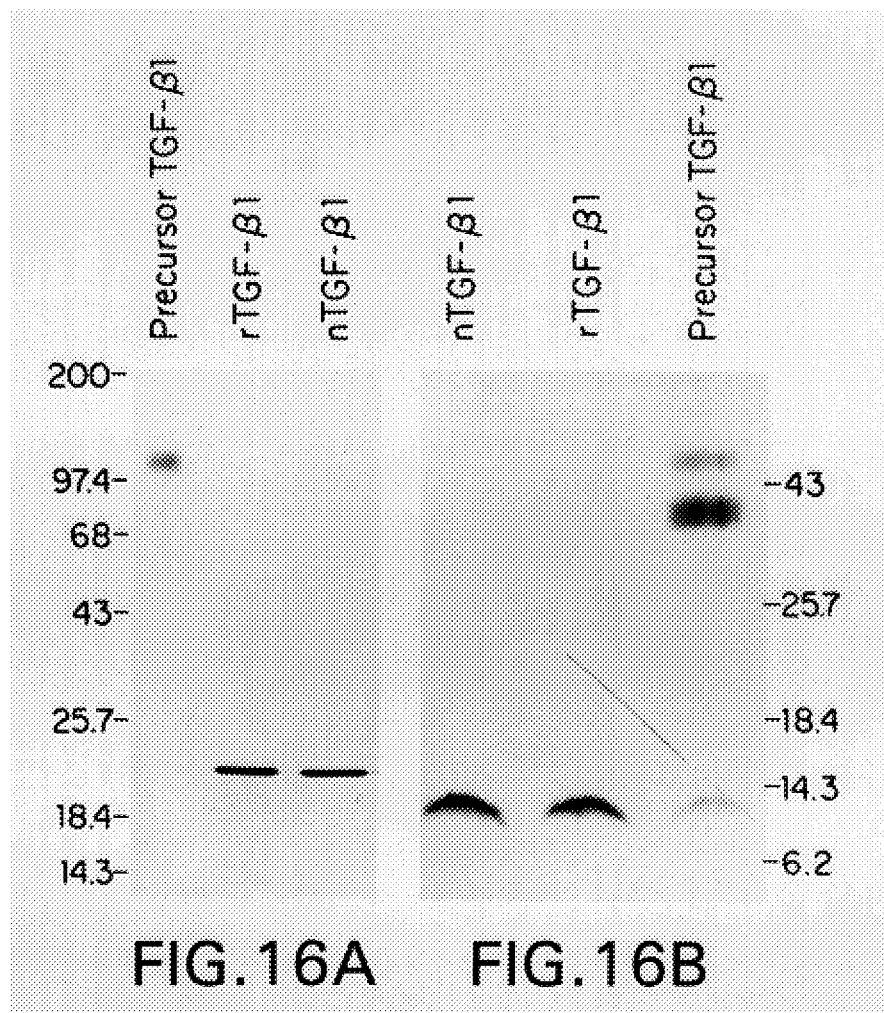

FIG. 16A and 16B. SDS-polyacrylamide gel analysis of purified rTGF-β1 proteins. Precursor and mature forms of TGF-β1 were fractionated by SDS-PAGE under non-reducing FIG. 16A or reducing FIG. 16 B) conditions and stained with Coomassie blue R-250. nTGF-β1 was isolated from bovine spleen and used for comparison. Marker proteins in KDal are indicated at the left and right of the figure.

Figure 17:
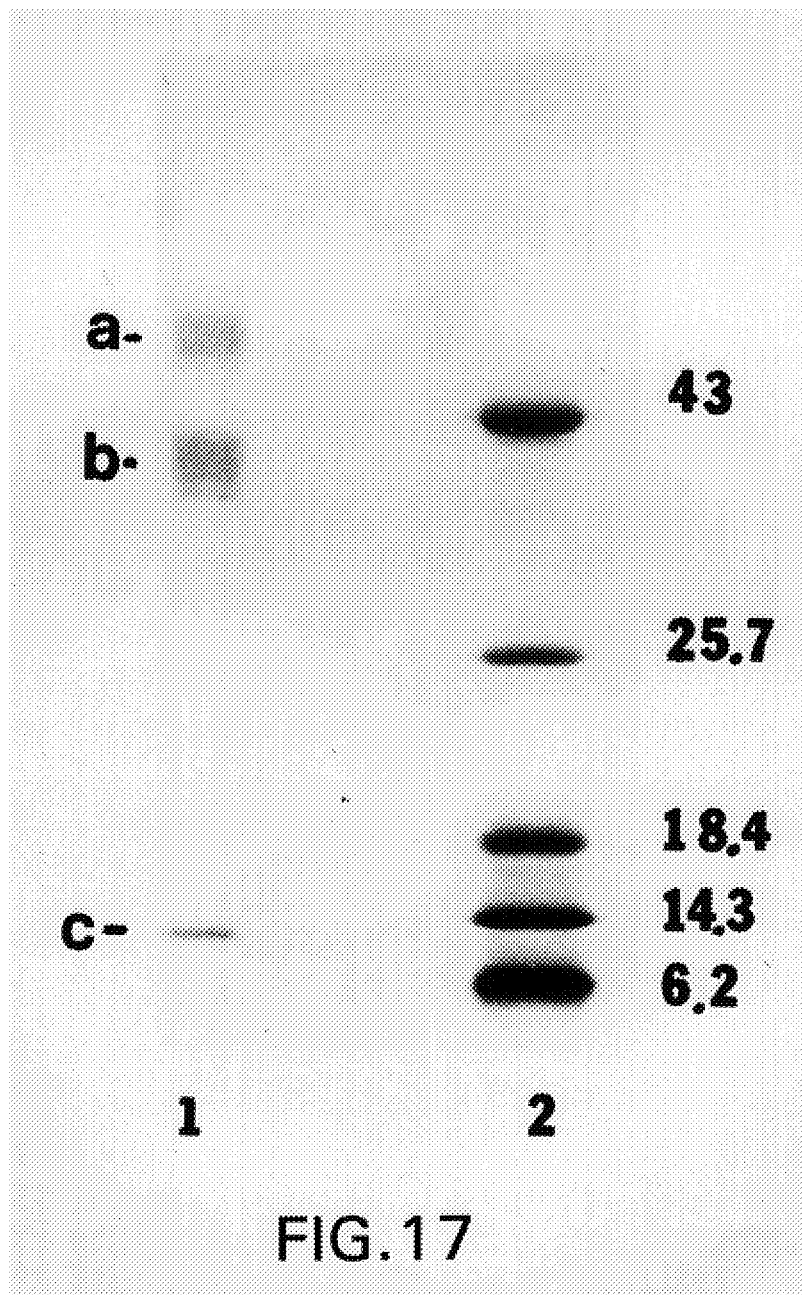

FIG. 17. Coomassie blue staining pattern of proteins from the conditioned medium of amplified CHO cells expressing TGF-β1. Conditioned medium was dialyzed, fractionated on 15% SDS-polyacrylamide gels under reducing conditions, and stained with Coomassie blue R-250. For reference, the letters a, b, and c are noted at the left of the figure to indicate rTGF-β1 molecules. Lane 1, 0.25 ml of conditioned medium; Lane 2, shows marker proteins with the indicated molecular weight in KDal.

Figure 18:
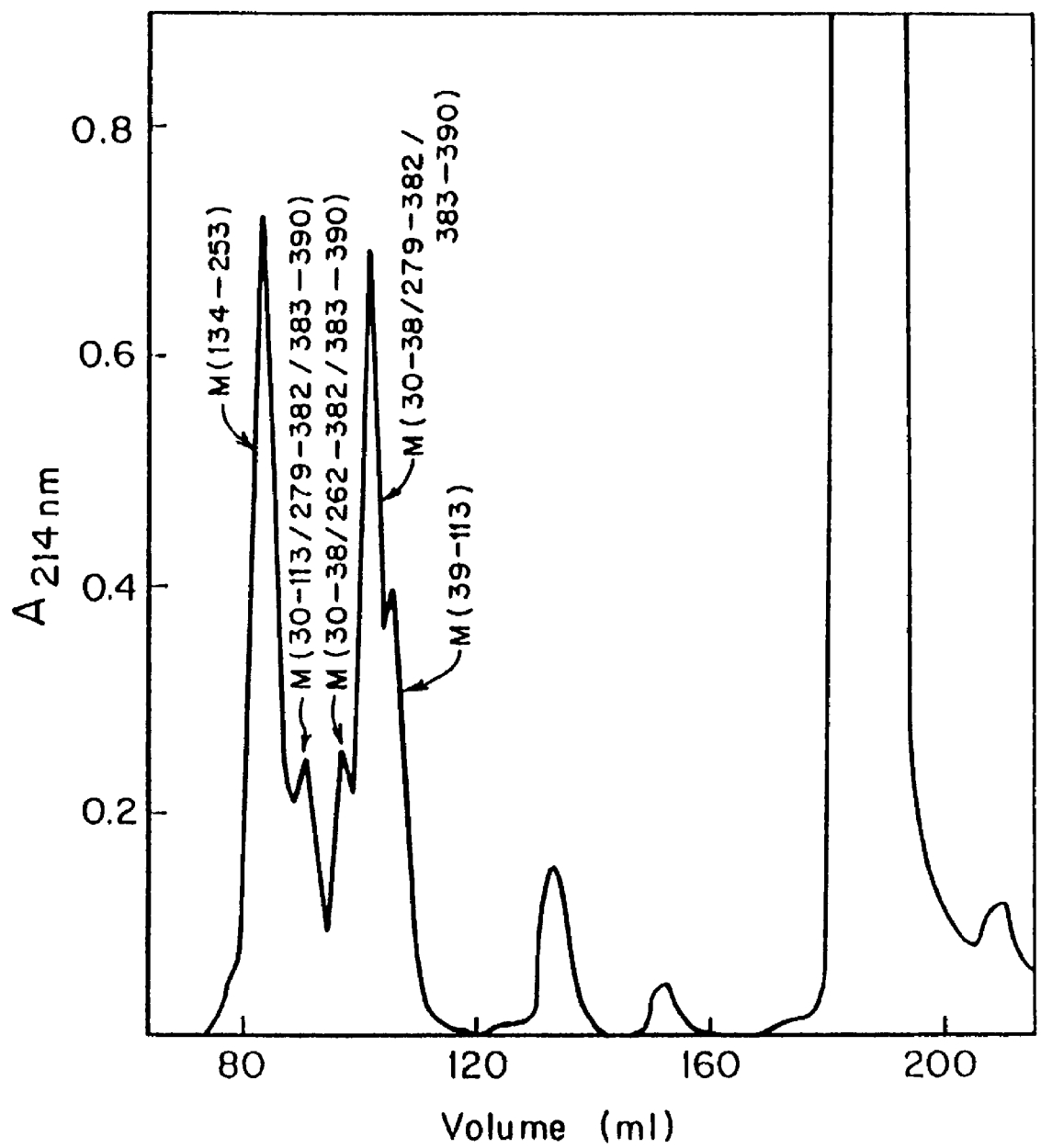

FIG. 18. Gel permeation chromatography on a Bio-Sil TSK-250 column (7.5×600 mm) of CNBr peptides of rTGF-β1-precursor. Elution pattern of 800 pmol of rTGF-β1-precursor cleaved with CNBr. The column was equilibrated with 0.1% TFA in water containing 40% acetonitrile at 0.25 mL/min, at 22° C. UV-absorbing material was monitored at 214 nm. Peaks designated M refer to CNBr peptides subjected to Edman degradation; numbers refer to the position of that particular fragment or fragments connected by disulfide bonds in the complete sequence (Sharples et al., 1987, DNA 6:239–244).

Figure 19:
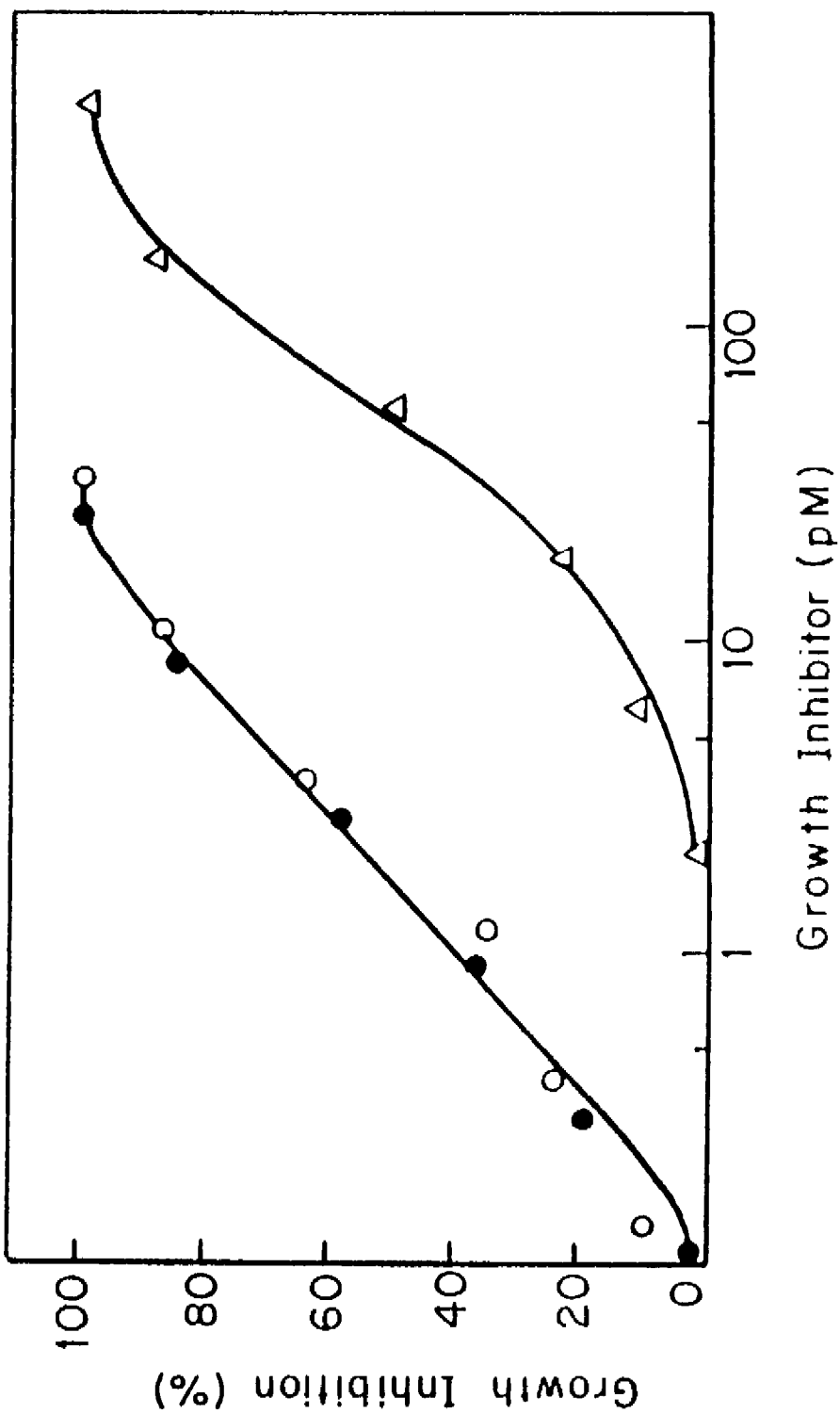

FIG. 19. Growth inhibition curves of purified TGF-β1 proteins using mink lung indicator cells. Growth inhibition was assessed as described in the text. Concentration of TGF-β1 polypeptides was determined by amino acid analysis. -Δ-, recombinant precursor protein; -●-, nTGF-β1 from bovine spleen; -○-, rTGF-β1.

Figure 20A:
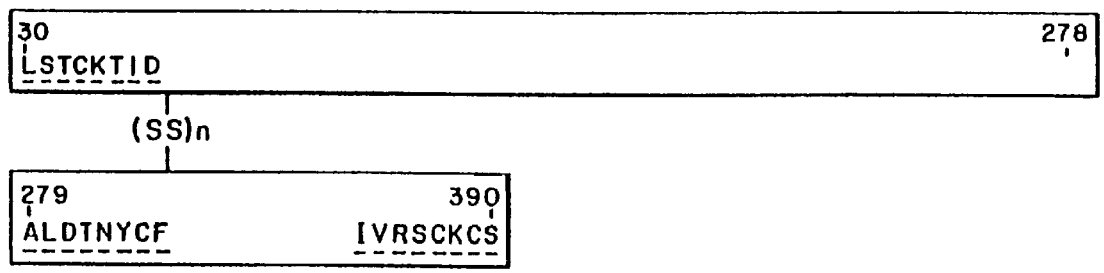
Figure 20B:
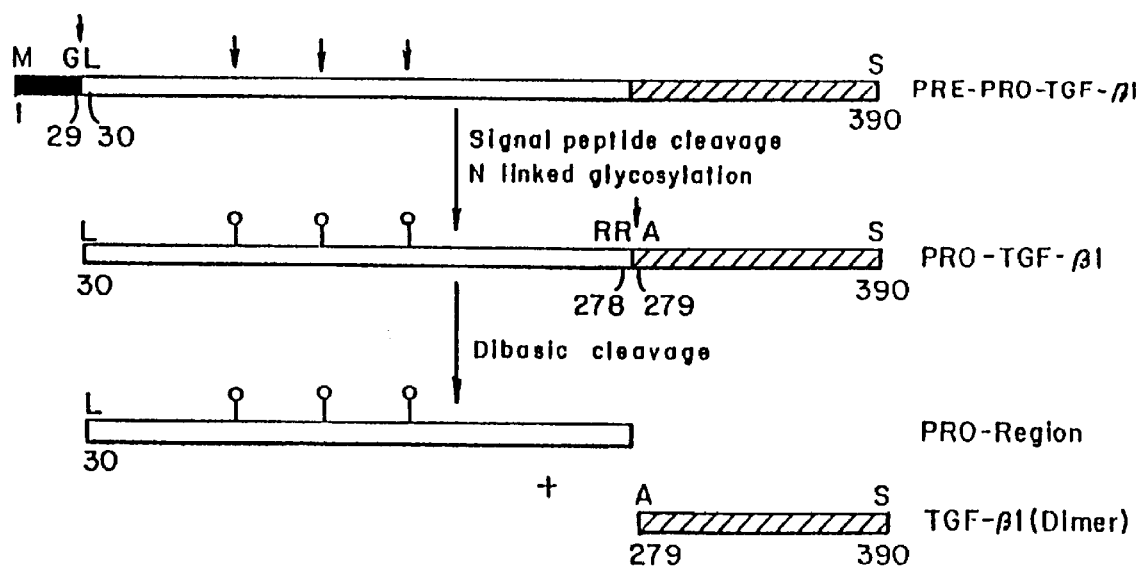

FIG. 20A and 20 B. FIG. 20 A: Proposed structure of TGF-β1 precursor highlighting its disulfide cross-linked nature. FIG. 20B: Summary of processing events of pre-pro-TGF-β1 in transfected CHO cells. Proteolytic processing sites have beer highlighted. Asterisks denote glycosylation sites. Darkened, signal peptide; open, pro region; hatched, mature TGF-β1.

Figure 21:
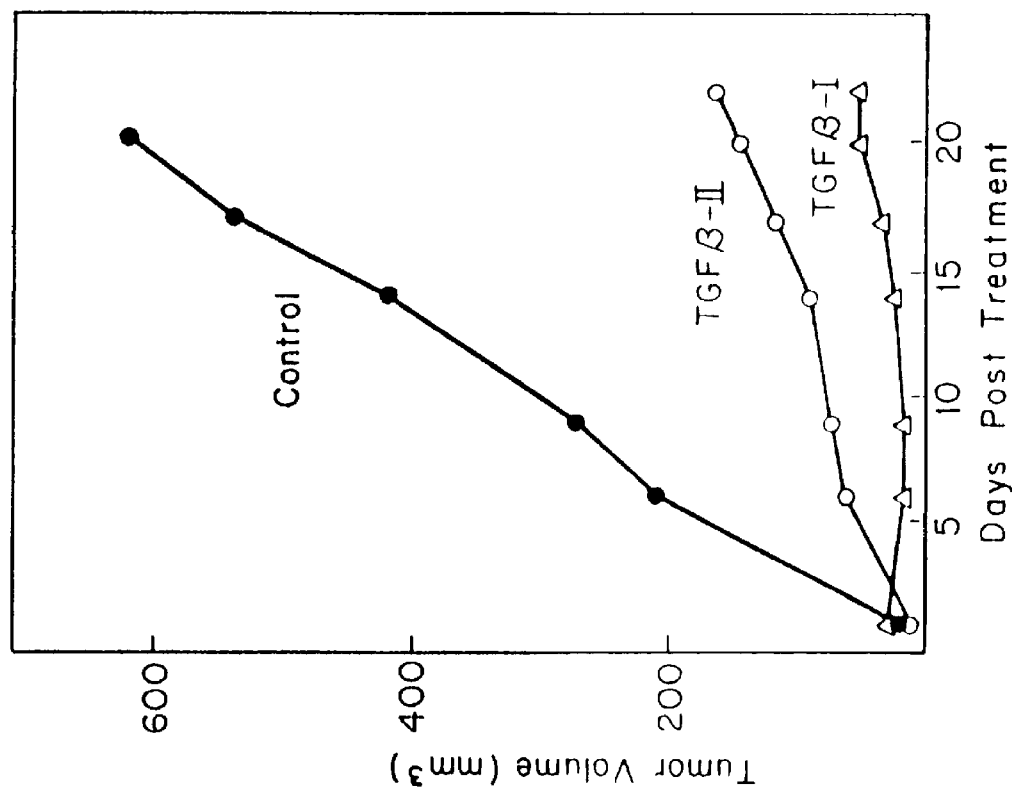

FIG. 21. Effect of TGF-β1 and TGF-β2 on the growth of A549 human lung tumors in nude mice. Male nude mice (Balb/c-nu+/nu+) at 12 weeks of age, were injected in the dorsal neck region subcutaneously with 1.3×10$^6$ human lung carcinoma cells (A549) in a volume of 0.2 mL of phosphate buffered saline. Palpable tumors (, 10 mm$^3$×3×1 mm) developed in 20 days in approximately 80% of the animals. Tumor bearing animals were randomly assigned to different cages. Day 1 of treatment corresponds to the first day animals were treated after measurable tumors developed. Each group of 5 animals were injected as indicated subcutaneously adjacent to the tumor (peritumorally) in a carrier volume of 0.10 mL. Control group(s) were injected with either high pressure liquid chromatography purified bovine serum albumin (2 μg) or a synthetic peptide (200 ng) corresponding to a loop region of epidermal growth factor (residues 11–21). Tumor size was measured with calipers in three dimensions before subsequent injections on the days indicated on the abscissa. Values for each point represent average tumor volume. TGF-β1 and TGF-β2 were purified to homogeneity from bovine bone as previously described (Massaque et al., 1986, Proc. Nat. Acad. Sci., 83:8206–8210; Sporn et al., 1983, Science 219:1329) and stabilized with a ten-fold excess of bovine serum albumin. Total amounts of each factor administered for the duration of this particular experiment were 1.4 μg per animal.

Figure 22:
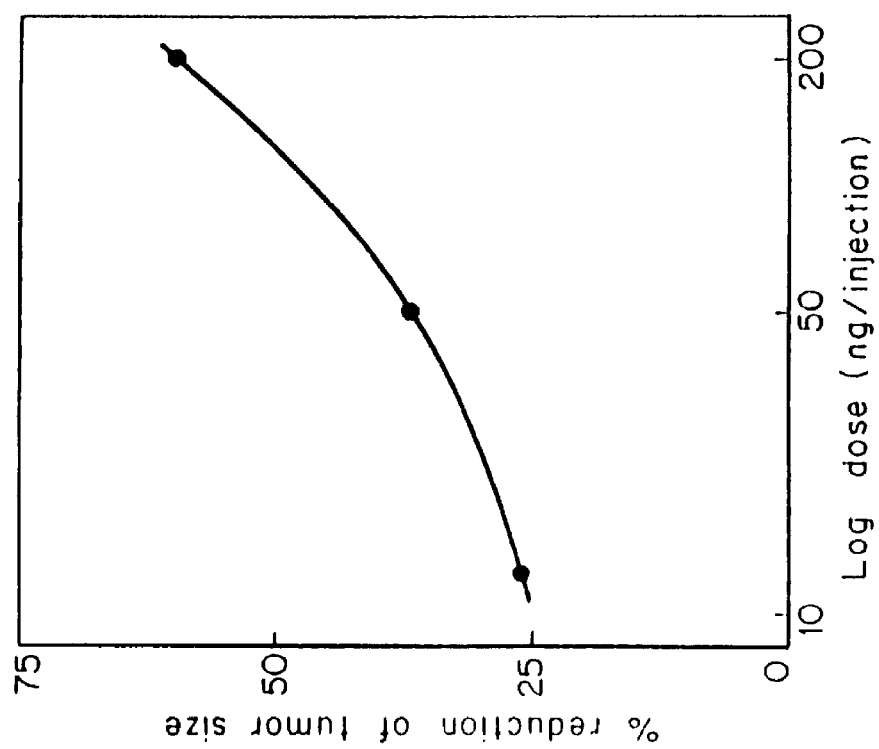

FIG. 22. Dose response of TGF-β1 inhibition of A549 human carcinoma tumors in nude mice. Protocol is identical to that described in description of FIG. 21 except that initial tumor size at day 1 of treatment (day 25 post tumor cell inoculation) was larger (20 mm$^3$). Control animal groups were injected with BSA; treated animal groups received 5 injections every third day of either 12.5, 50 or 200 ng of TGF-β1 peritumorally administered over a 15-day period. Values represent the average tumor volume from each group of animals at day 15.

Figure 23:

FIG. 23. Photograph of non-treated and TGF-β1 treated A549 lung carcinoma bearing nude mice. Top of photo is control animal bearing large subcutaneous tumor at day 20 (actual photo of mice from experiment described in FIG. 21); bottom of photo is animal representative of TGF-β1-treated group (same experiment). Inset (upper right) shows excised tumors from control (left) and treated (right) animals. (Size differences in photo between tumors in animals and after excision reflects difference in camera range.)

Figure 24A:
Figure 24B:
Figure 24C:
Figure 24D:
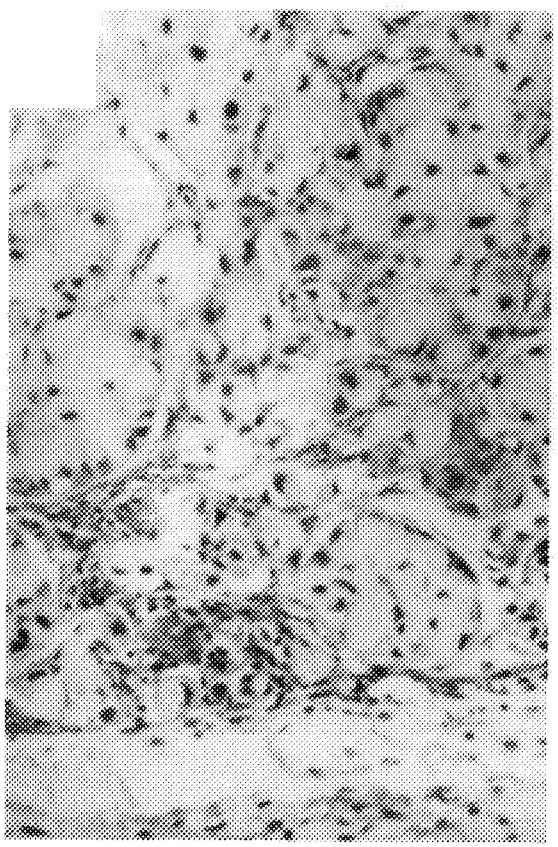
Figure 25A:
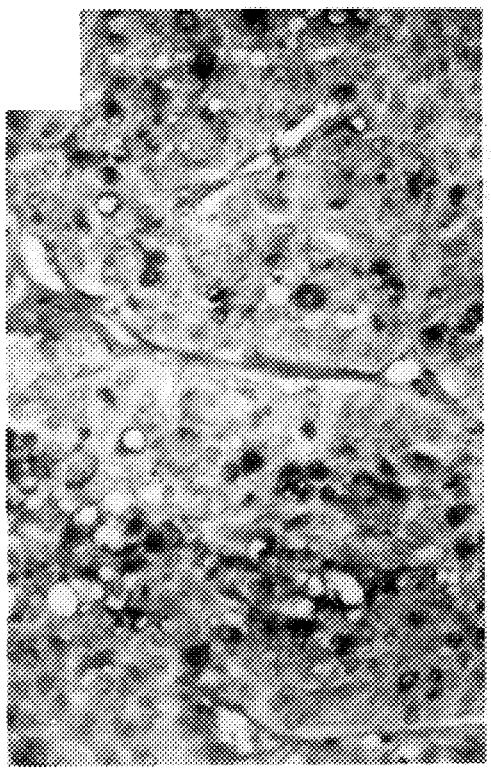
Figure 25B:
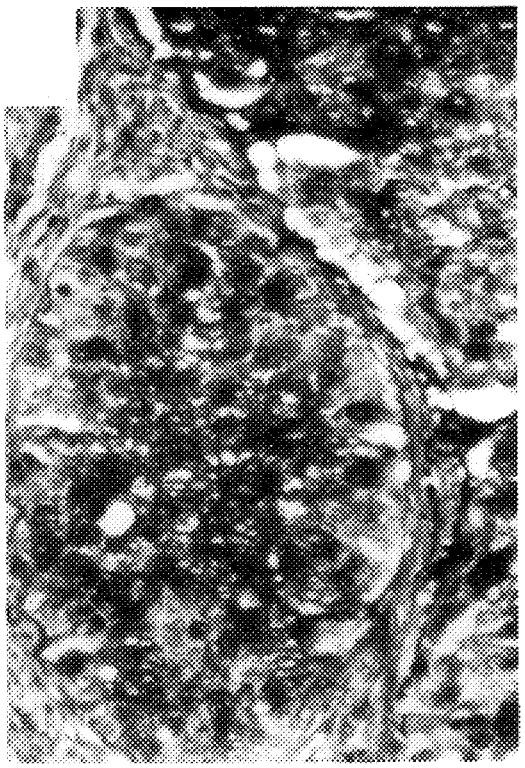
Figure 25C:
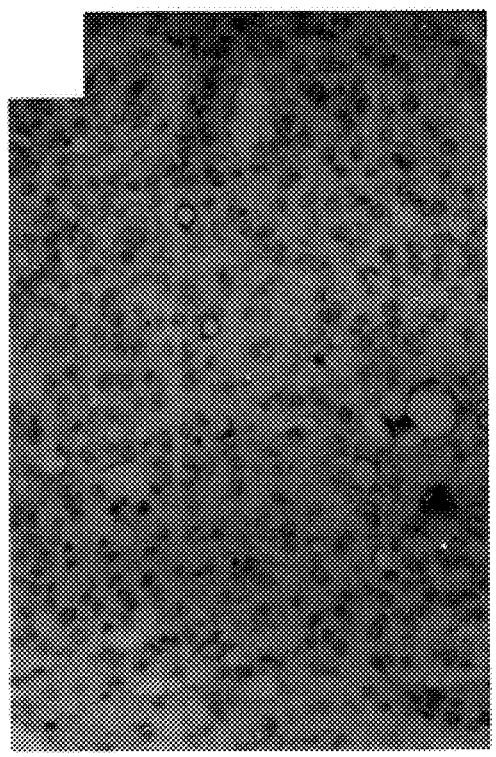
Figure 25D:

FIGS. 24A–24D. Histological examination of tumors excised from mock and TGF-β1-treated animals. Freshly excised tumors (day 20 of treatment, FIG. 21) were fixed in buffered formalin imbedded in paraffin, sectioned and stained with Gamori's trichrome. Section of tumor derived from mock-treated animals, FIG. 24A (20X), FIG. 24C (100X). Section of tumor derived from TGF-β1 treated animals. FIG. 24B (20X), FIG. 24D (100X). FIG. 24D inset; vessel wall from section of tumor derived from TGF-β1 treated-animals (100X).

FIGS. 25A–25D. Staining pattern of fixed human lung tumor sections from mock-treated and TGF-β1-treated animals. Sections of tumors derived from mock-treated animals stained with PAS (FIG. 25A), 100X; with Alcian Blue (FIG. 25C) 100X; section of tumor derived from TGF-β1-treated animals stained with PAS, (FIG. 25B) 100X; Alcian Blue (FIG. 25D) 100X.

Figure 26A:
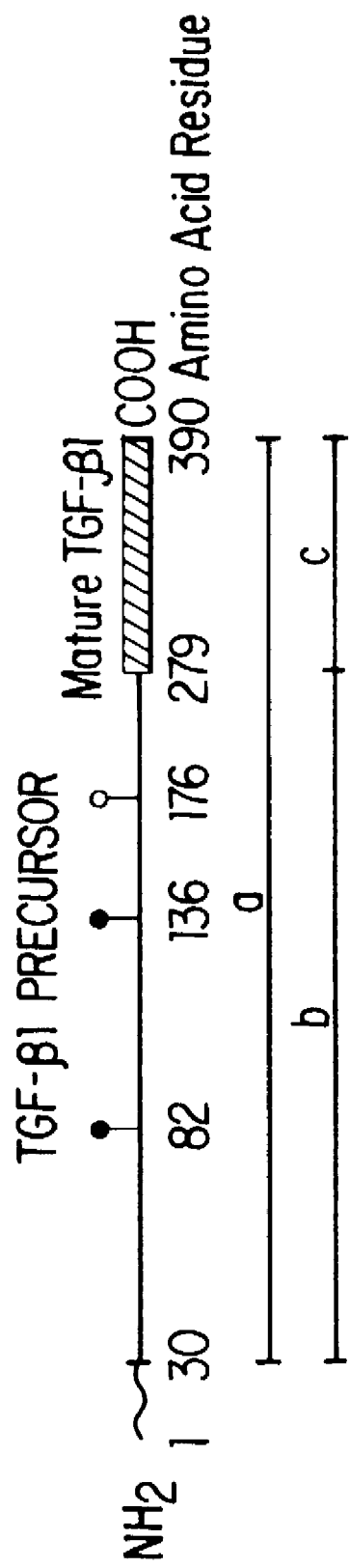
Figures 26B, 26C, 26D, 26E:
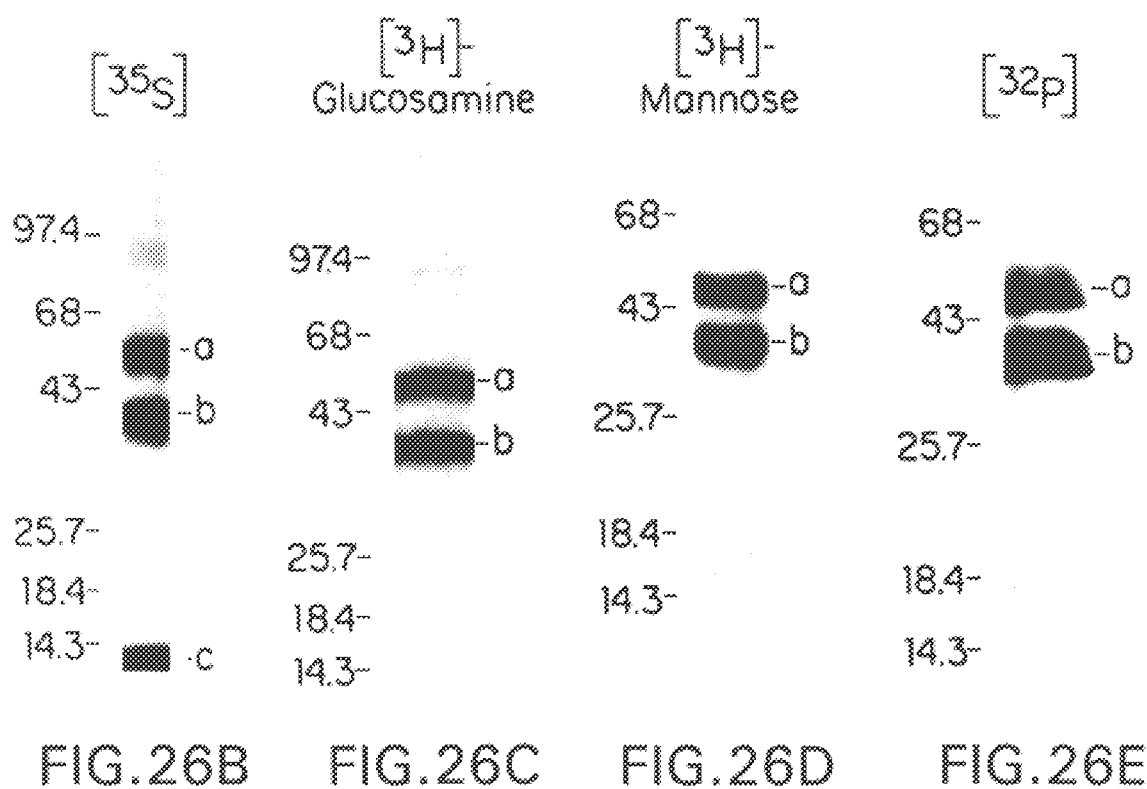

FIG. 26A–26E. SDS-Polyacrylamide gel electrophoresis of TGF-β1 precursor proteins released by clone 17 cells. FIG. 26 A: Line diagram of TGF-β1 protein; ꜟ, indicates glycosylation sites which are phosphorylated; ꜞ, indicates non-phosphorylated glycosylation sites. Cell free supernatants from clone 17 cells were labeled with [$^{35}$S]-methionine and [$^{35}$S]-cysteine (FIG. 26B), [$^3$H]-glucosamine (FIG. 26C), [H]-mannose (FIG.26D) and [$^{32}$P]-phosphate (FIG. 26E) in serum-free media; samples were processed and analyzed on a 7.5–15% gradient SDS-polyacrylamide gel (FIGS. 26B and 26C), or on a 15% SDS-polyacrylamide gel (FIGS. 26D and 26E).

Figures 27A, 27B:
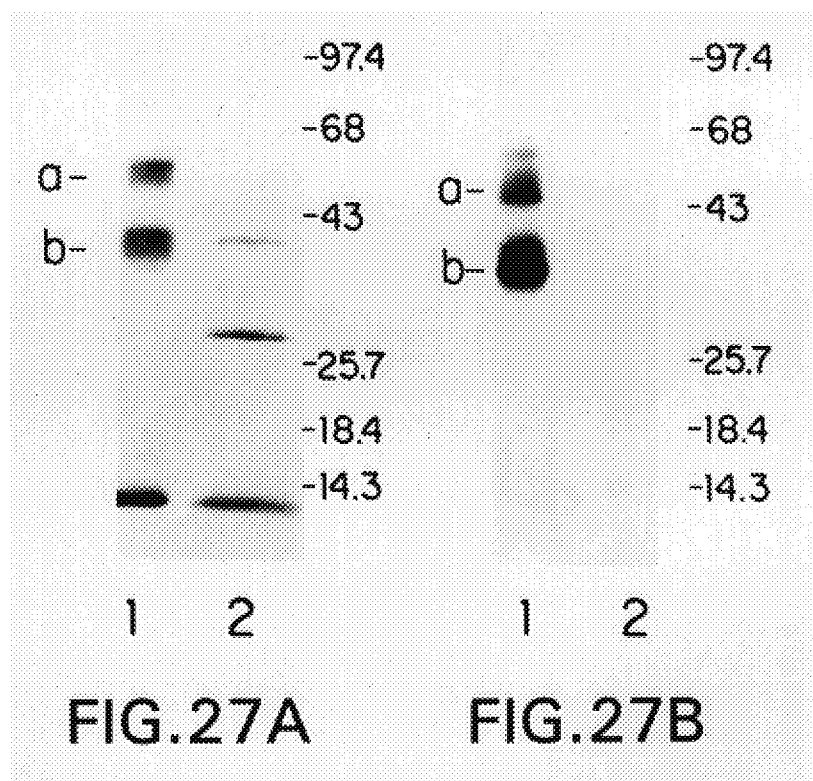

FIGS. 27A and 27B. N-glycanase digestion of TGF-β1 precursor proteins produced by clone 17 cells. FIG. 27A: [$^{35}$S]-labeled cell free supernatants were processed, treated with N-glycanase and analyzed on a 7.5–15% gradient SDS-polyacrylamide gel: lane 1, no enzyme; lane 2, plus N-glycanase. FIG. 27B: Same as in FIG. 27A, except the label was [$^{32}$P]-phosphate.

Figures 28, 29:
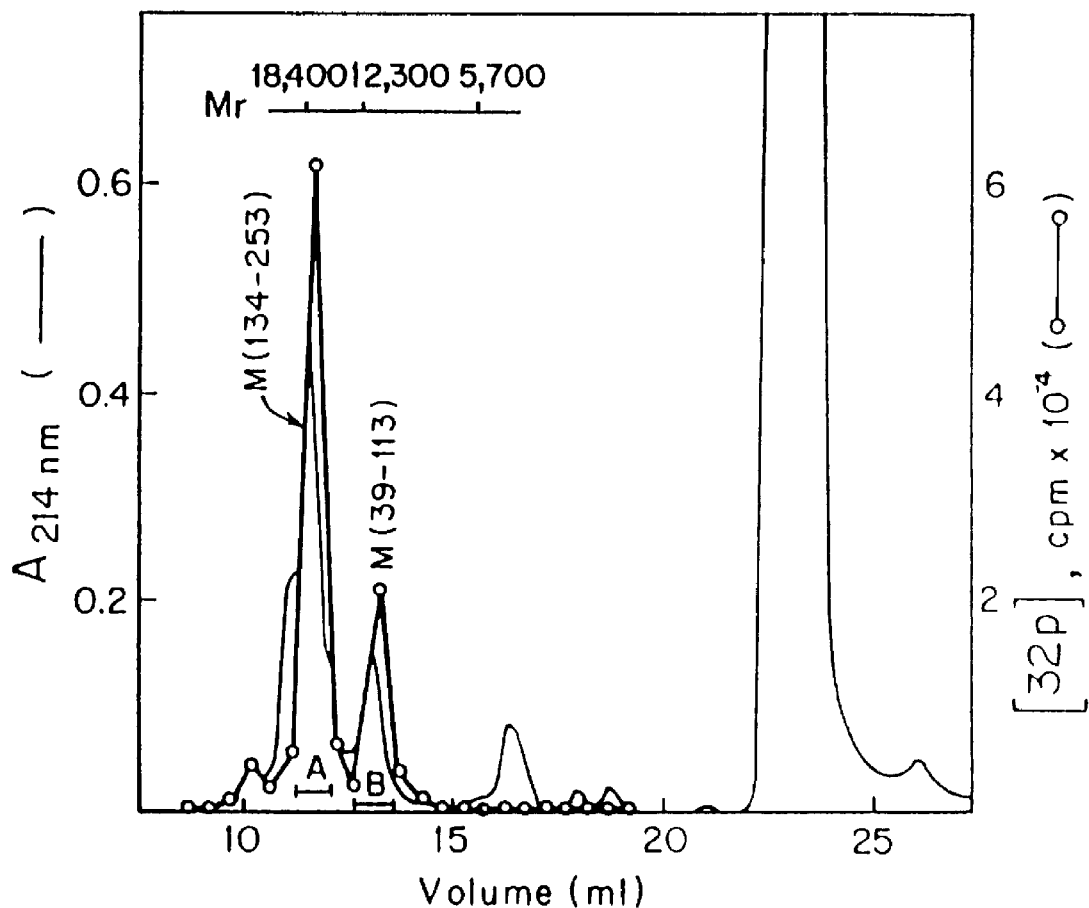

FIG. 28. Amino acid sequences of TGF-β1 precursor glycopeptides. Peptides obtained by cleavage with S. aureus V8 protease (E), and trypsin (T) are indicated. ꜟ, indicates glycosylation sites which are phosphorylated; ꜞ, indicates non-phosphorylated glycosylation sites. The numbering refers to the position of the particular glycopeptide in the complete sequence of the TGF-β1 precursor. x, unidentified residue.

FIG. 29. Gel permeation chromatography of CNBr peptides of [$^{32}$P]-labeled TGF-β1 precursor. Chromatography on a Bio-sil TSK-250 column (7.5×600 mm). Elution pattern of 650 pmol of S-pyridylethylated TGF-β1 precursor and of 165,000 cpm of S-pyridylethylated [$^{32}$P]-TGF-β1 precursor cleaved with CNBr. The indicated fractions were measured for [$^{32}$P]- radioactivity (-o-). The solid line gives the protein absorbance at 214 nm. The following proteins were used as markers: α-lactoglobulin (Mr 18,400), cytochrome C (Mr 12,300), and insulin (Mr 5,700). Peaks designated by an M refer to CNBr peptides; numbers refer to the position of that particular fragment in the complete sequence of the TGF-β1 precursor (Sharples et al., 1987, DNA 6:239–244).

Figure 30:
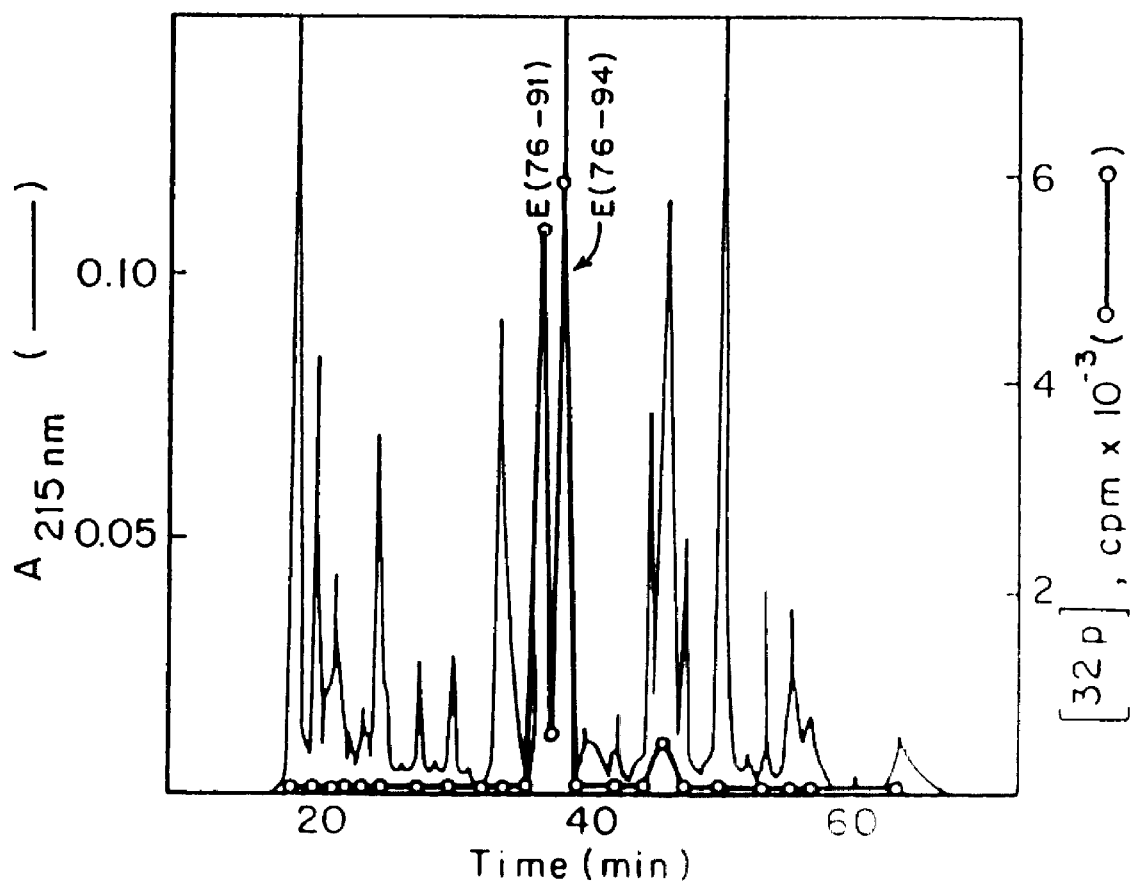

FIG. 30. Reversed-phase high performance liquid chromatography of S. aureus V8 protease peptides of CNBr peptide M(39-113). Chromotography on an RP-300 column (2.1×30 mm). Elution pattern of 370 pmol of M(39-113) containing 12,500 cpm of [ 32P]-M(39-113) digested with S. aureus V8 protease. The elution of peptides was achieved with a 2-hour linear gradient of 0.1% trifluoroacetic acid in water to 60% acetonitrile containing 0.08% trifluoroacetic acid at a flow rate of 100 pl/min, at 35° C. UV-absorbing material was monitored at 215 nm (---). [$^{32}$P] radioactivity (o) was determined in an LS 6800 liquid scintillation counter (Beckman). Peaks designated by an E refer to V8 protease peptides subjected to Edman degradation.

Figure 31A:
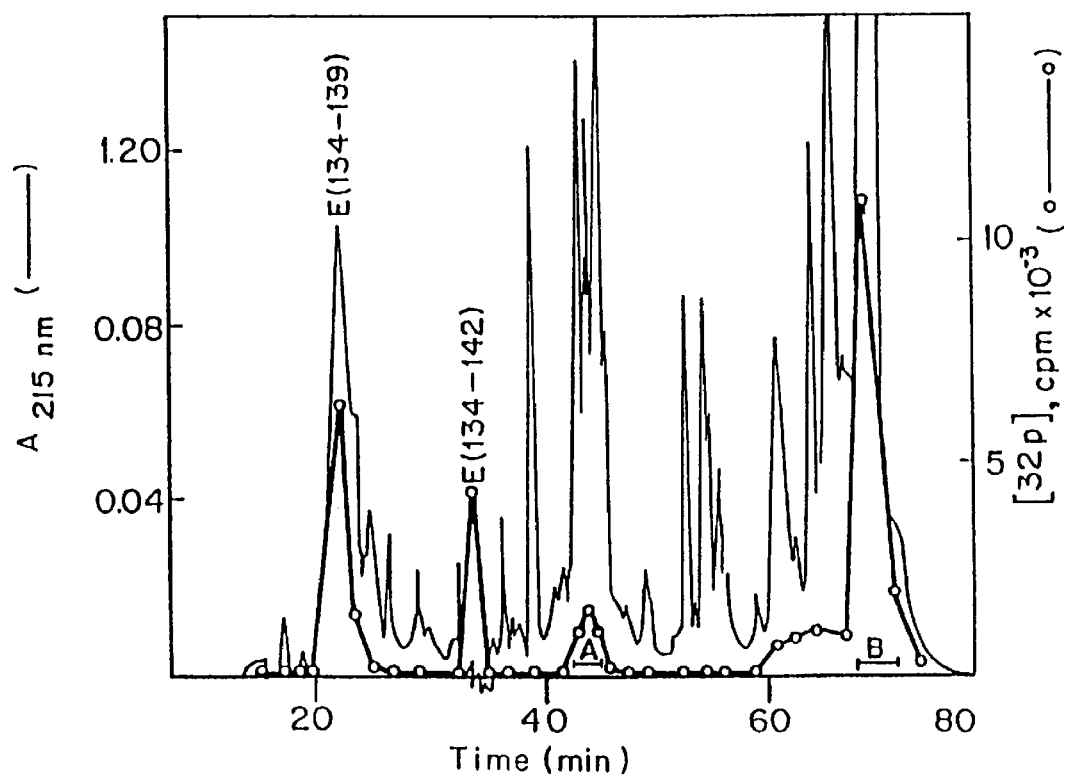
Figure 31B:
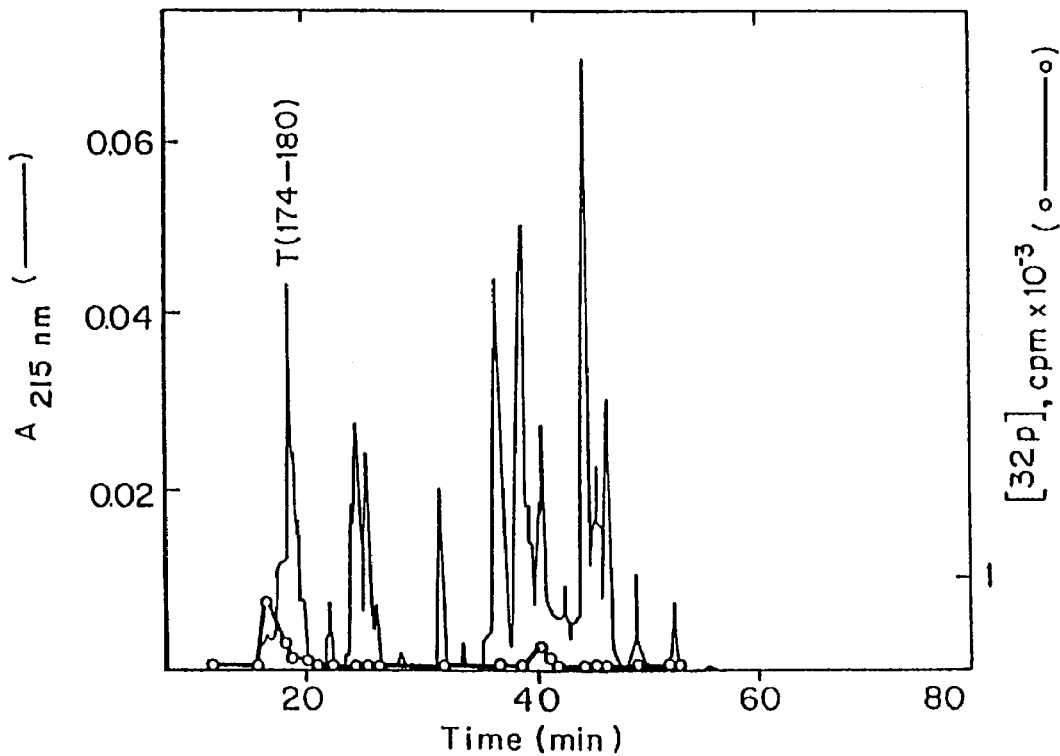

FIGS. 31A and 31B. Reversed-phase high performance liquid chromatography of S. aureus V8 protease peptides and trypsin peptides of CNBr peptide M(134-253). Chromatography on an RP-300 column (2.1×30 mm). FIG. 31A Elution pattern of 400 pmol of M(134-253) containing 44,000 cpm of [$^{32}$P]-M(134-253) digested with S. aureus V8 protease. FIG. 31B: Elution pattern of trypsin peptides derived from pool A (FIG. 31A) containing 3,100 cpm of [$^{32}$P]-E(170-194). The chromatography conditions are described in the legend to FIG. 30. Peaks designated by an E refer to V8 protease peptides, and peaks designated with a T refer to trypsin peptides subjected to Edman degradation.

Figure 32A:
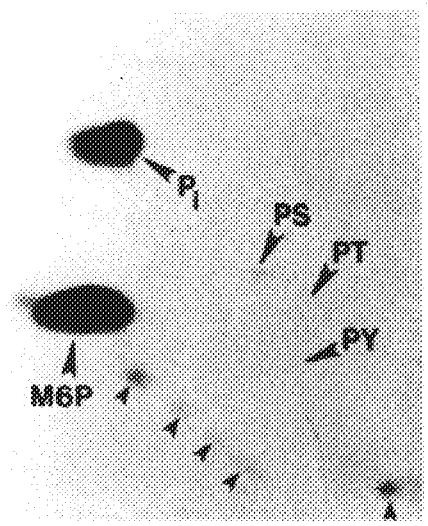
Figure 32B:
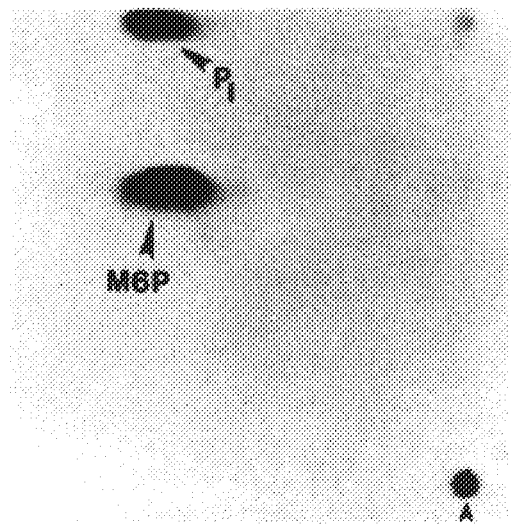
Figure 32C:
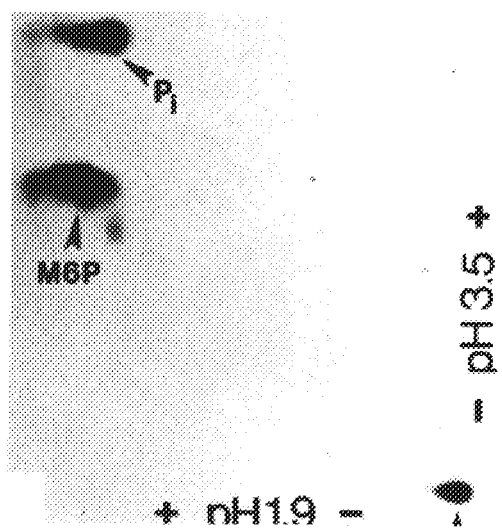
Figure 32D:
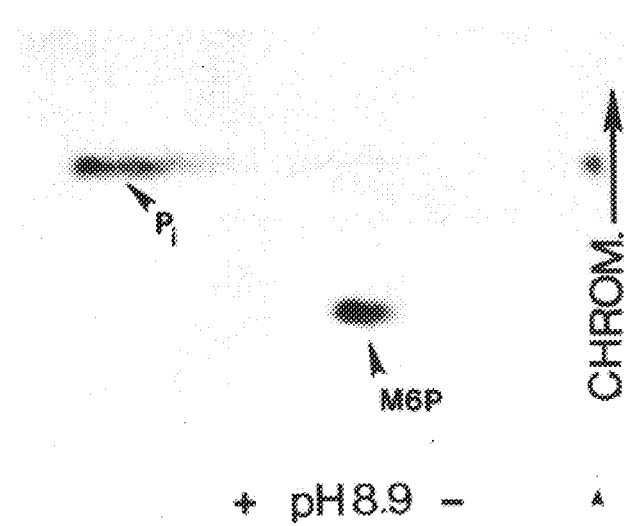

FIGS. 32A–32D. Identification of mannose-6-phosphate. FIG. 32A: [$^{32}$P]-labeled TGF-β1 precursor proteins were hydrolyzed with acid for 2 hours. Hydrolysis products were mixed with non-radioactive phosphoaminoacids and mannose-6-phosphate and separated by electrophoresis at pH 1.9, and orthogonally, at pH 3.5. An autoradiogram is shown. The sample is spotted at lower right (arrowhead). Mannose-6-phosphate (M6P), phosphoserine (PS), phosphothreonine (PT), phosphotyrosine (PY) and inorganic phosphate (Pi), are marked. [$^{32}$P]- was detected comigraging with mannose-6-phosphate and Pi, and in positions expected for phospho-oligosaccharides (small arrowheads). FIGS. 32B and 32C: Similar analyses of products of 1 hour hydrolysis of (FIG. 32B) E(76-91) and (FIG. 32C) E(134-139). FIG. 32D: [$^{32}$p]-labeled TGF-β1 precursor proteins were hydrolyzed and separated by electrophoresis at pH 8.9 followed by chromatography.

Figure 33A:
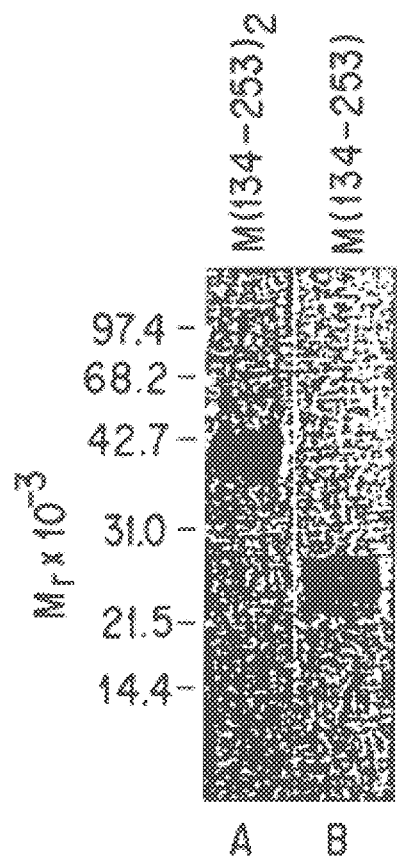

FIG. 33A. SDS-polyacrylamide gel analysis of purified cyanogen bromide peptide M(134-253). M(134-253) was fractionated on a 15% SDS-polyacrylamide gel under (1) non-reducing or, (2) reducing conditions, and statined with Coomassie brilliant blue R-250. Molecular weight markers are indicated in kilodaltons.

Figures 33B, 33C:
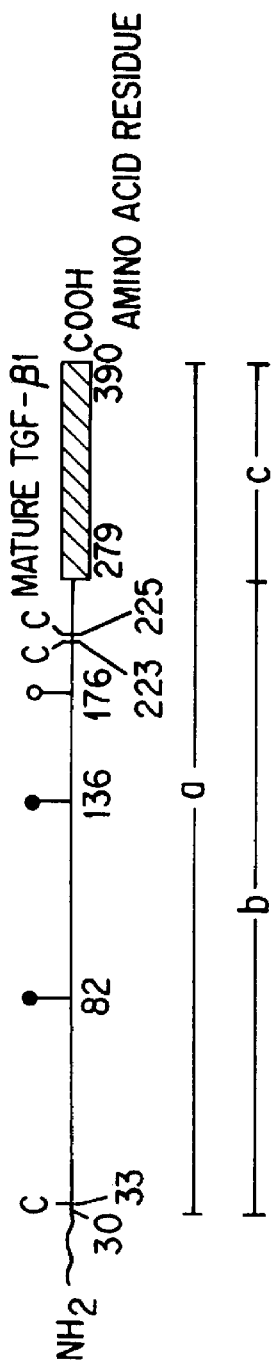

FIG. 33B. Line diagram of pre-pro-TGF-β1. Pro-TGF-β1, the pro region of the precursor, and mature TGF-β1 are indicated by lanes a,b, and c, respectively. CYS (C) residues in the pro region are indicated. Mannose-6-phosphate containing sites (↑) and non-phosphorylated sites (?) of N-linked glycosylation are shown.

FIG. 33C. TGF-β1 precursor mutants. Superscripts indicate the amino acid positions of the SER substitutions. Unmatched nucleotides are in bold print and new SER codons are underlined.

Figure 33D:
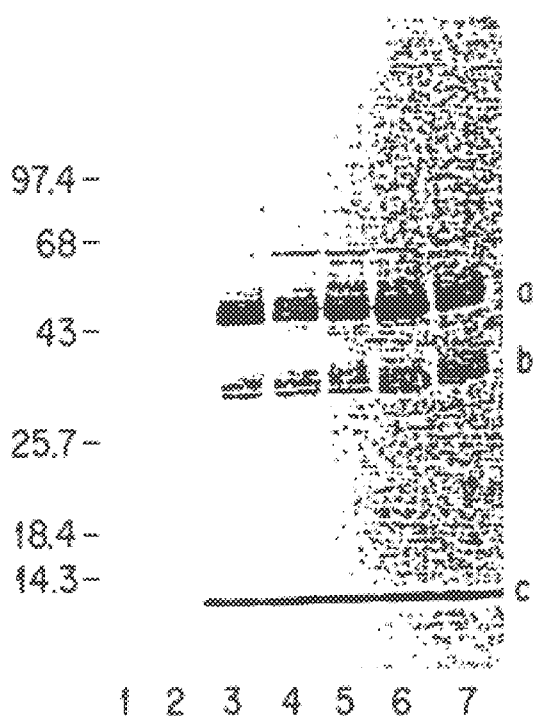
Figure 33E:
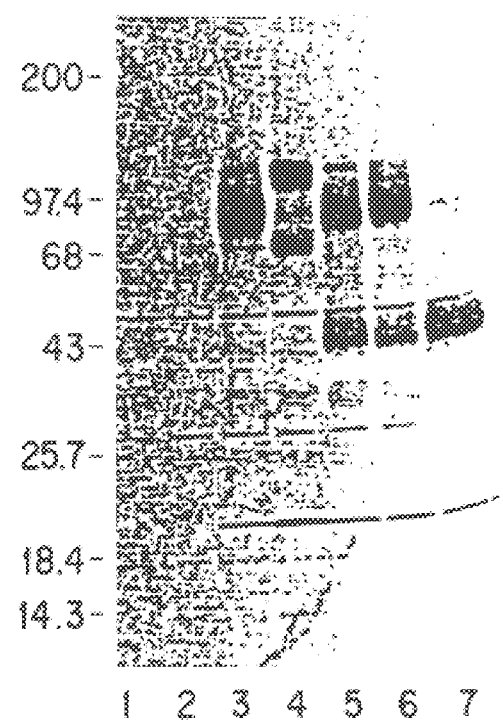

FIGS. 33D and 33E. Immunoblots of TGF-β1 mutant proteins secreted by transfected COS cells. Serum-free supernatants were collected, dialyzed against 0.2M acetic acid, fractionated on 7.5–17.5% SDS-polyacrylamide gels and analyzed by immunoblotting under reducing (FIG. 33D) or non-reducing (FIG. 33E) conditions. Blots were probed with a mixture of pro region (anti-TGF-β1$^{81\text{-}94}$) and mature (anti-TGF-β1$_{369\text{-}381}$) specific anti-peptide antibodies. COS cells were transfected with vector (πH3M) only (lane 2), or with vector encoding TGF-β1 (lane 3), TGF-β1$^{S33}$ (lane 4), TGF-β1$^{S223}$ (lane 5), TGF-β1$^{S225}$ (lane 6), and TGF-β1$^{S223/225}$ (lane 7). Lane 1 contains supernatant from non-transfected COS cells. Molecular weight standards are indicated in kilodaltons.

Figure 33F:
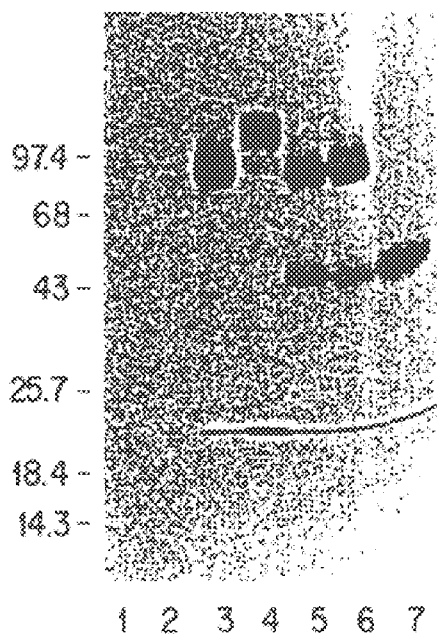
Figure 33G:
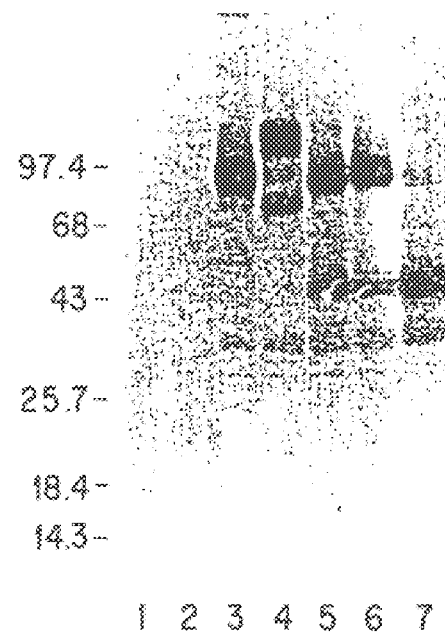

FIGS. 33F and 33G. Identification of mutant TGF-β1 precursor and mature proteins. Supernatants from COS cells transfected with πH3M (lane 2), pTGF-β1 (lane 3), pTGF-β1$^{S33}$ (lane 4), pTGF-β1$^{S223}$ (lane 5), pTGF-β1$^{S225}$ (lane 6) or pTGF-β1$^{S223/225}$ (lane 7), were collected and processed as described in the description of FIGS. 33D and 35E. Immunoblots were performed under non-reducing conditions with antibodies specific for (FIG. 33F) mature sequences (anti-TGF-β1$_{369\text{-}381}$), or (FIG. 33G) the pro region (anti-TGF-β1$_{81\text{-}94}$). Lane 1 contains non-transfected COS cell supernatant. Molecular weight standards are indicated in kilodaltons.

Figure 34:
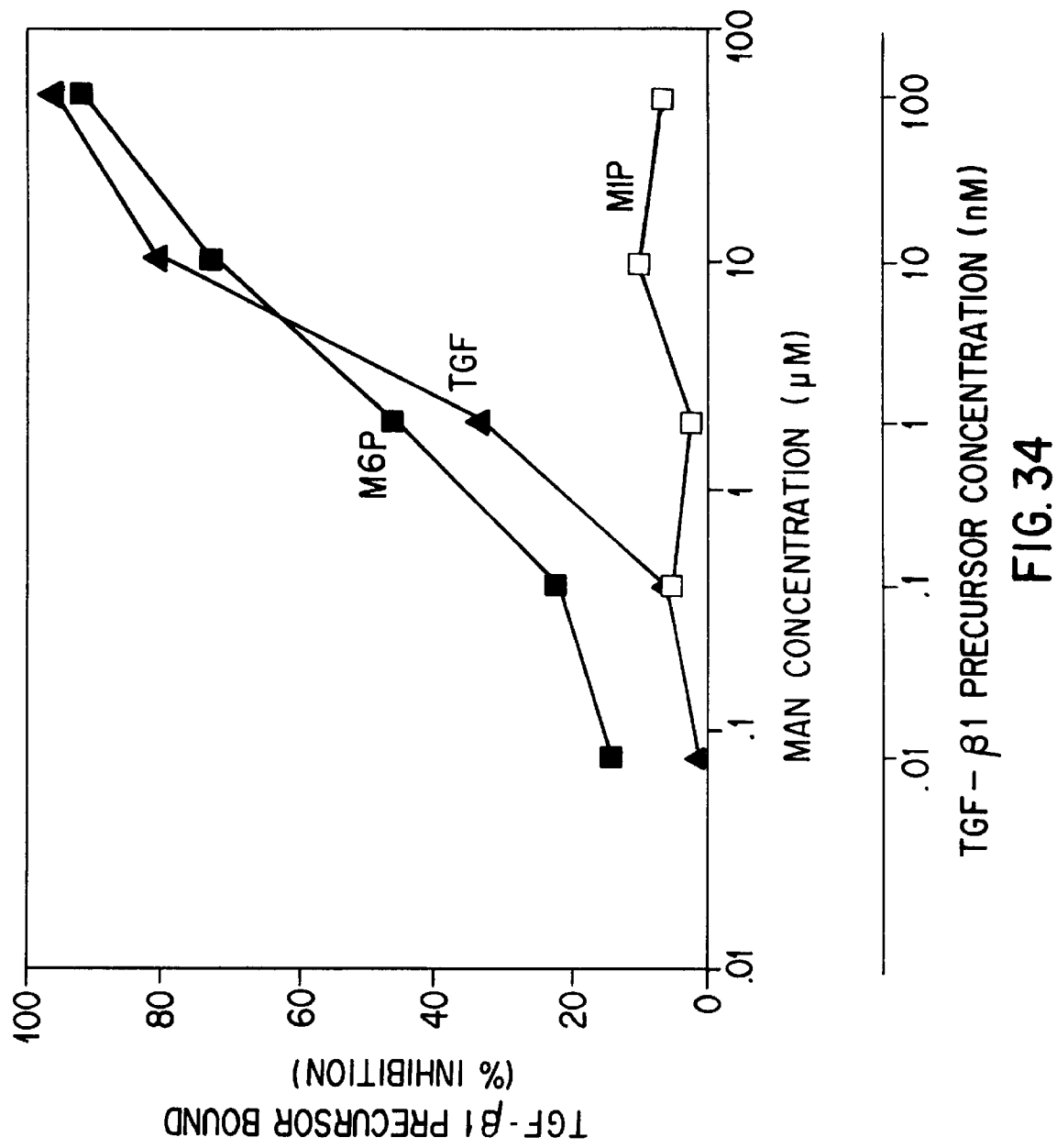

FIG. 34. Binding of $^{125}$I-labeled TGF-1 precursor to purified mannose 6-phosphate receptor. Purified human mannose 6-phosphate/IGF-II receptor (Roth et al., 1987, Biochem. Biophys. Res. Commun. 149:600–606) was adsorbed to microtiter wells coated with antibodies to this receptor. $^{125}$I-Labeled TGF-β1 precursor (100,000 cpm per well) was added in the presence of the indicated concentrations of unlabeled competitors. After 3 h at 4° C., the wells were washed, cut out, and counted. Results are averages of duplicate wells that differed by less than 10% and are representative of three experiments. In wells containing no competitor (0% inhibition), 5.2% of the labeled ligand was bound. TGF, TGF-β1 precursor; M1P, mannose 1-phosphate, M6P, mannose 6-phosphate.

Figure 35A:
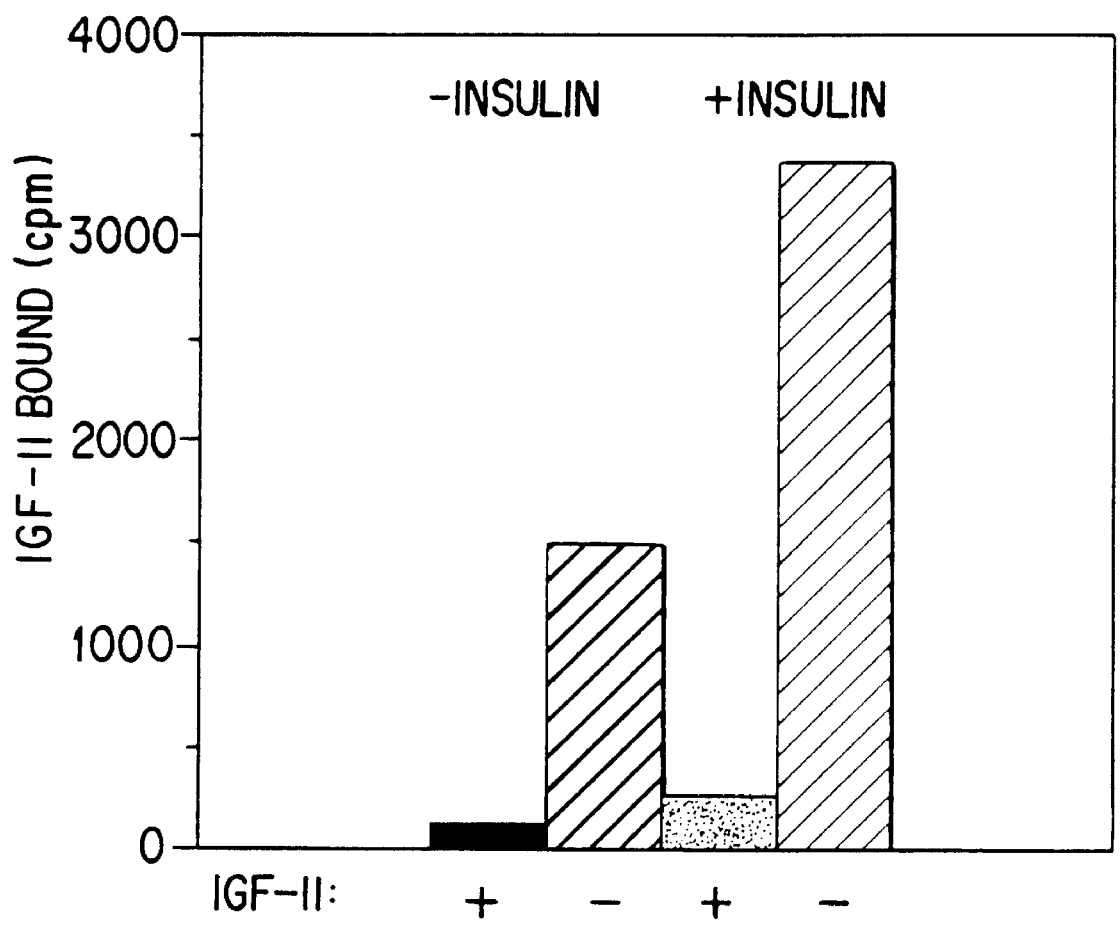
Figure 35B:
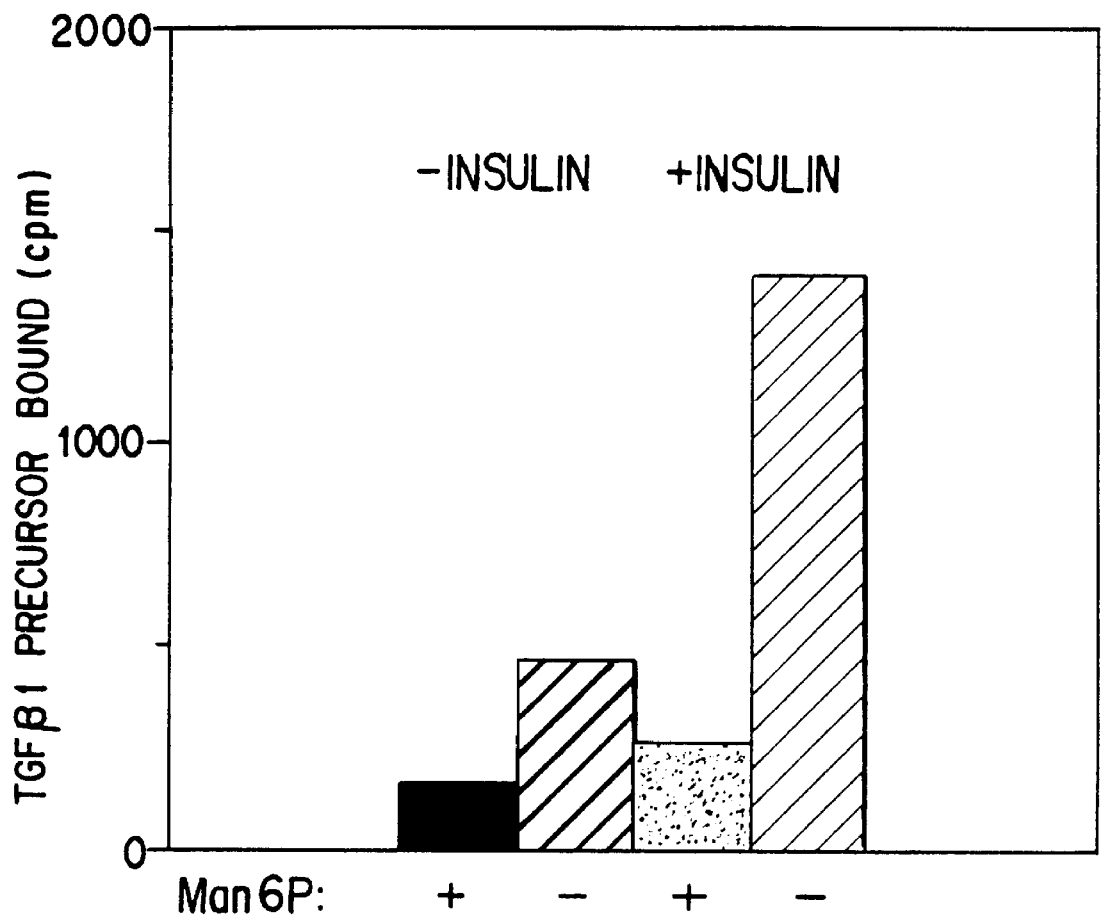

FIGS. 35A and 35B. Insulin stimulated increase in IGF-II and recombinant TGF-β1 precursor binding to rat adipocytes. Rat adipocytes pretreated or not with insulin were incubated with either (FIG. 35A) recombinant $^{125}$I-TGF-β1 precursor (4.9×10$^4$ cpm) or (FIG. 35B) $^{125}$I-IGF-II (4.2×10$^4$ cpm). To assess non-specific binding, 100 nM IGF-II or 3 mM man6P were included as indicated. Results are averages of triplicate determinations.

Figure 36A:
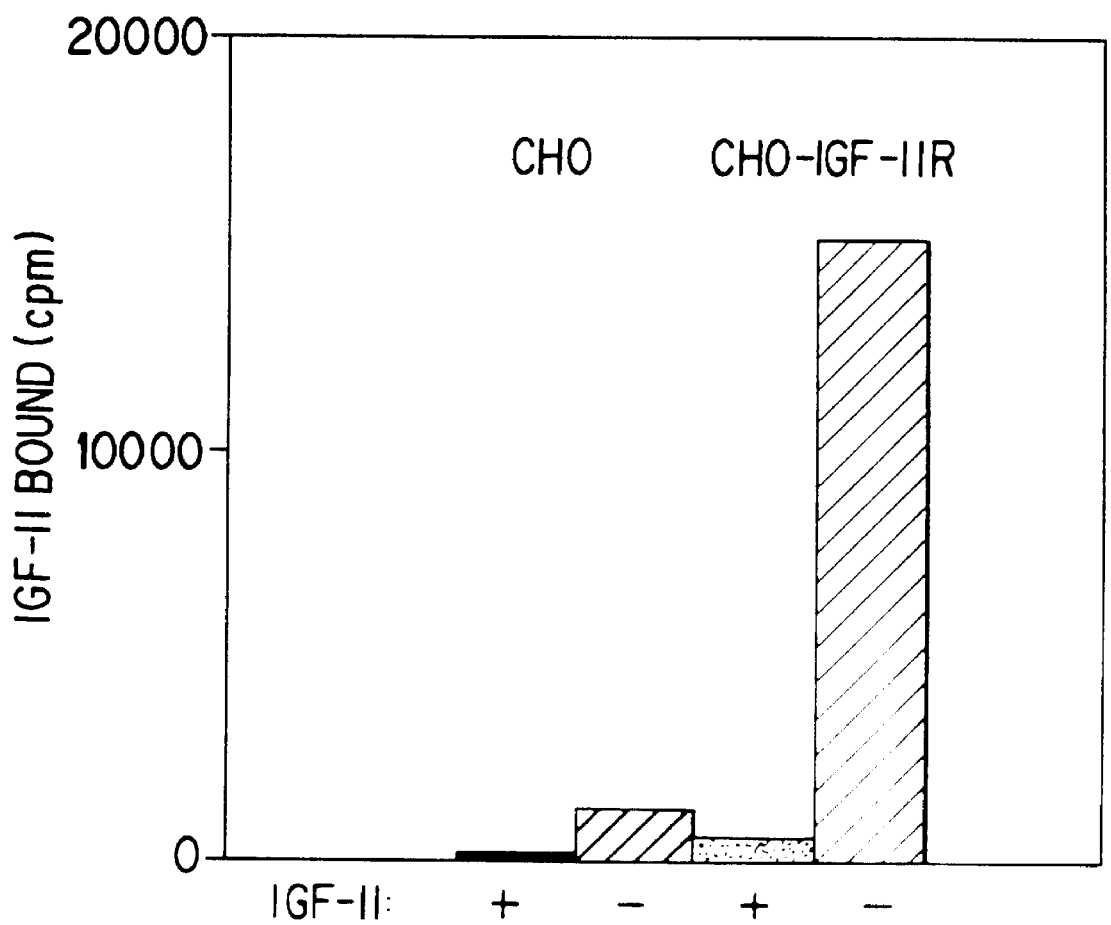
Figure 36B:
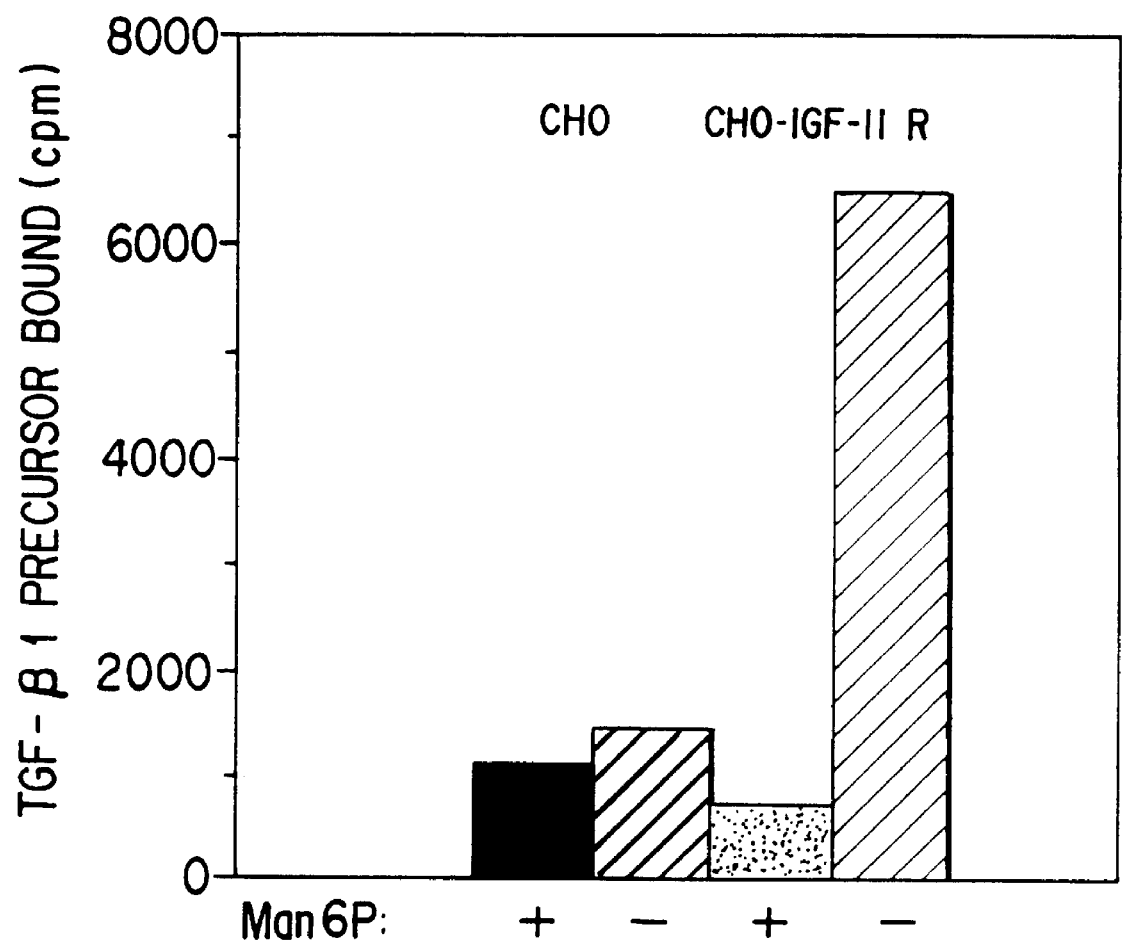

FIGS. 36A and 36B. Binding of IGF-II and recombinant TGF-β1 precursor to CHO cells and CHO cells overexpressing the human IGF-II/man6P receptor (CHO-IGF-IIR). Cells were incubated with either $^{125}$I-IGF-II (8.0×10$^4$ cpm) (FIG. 36A) or recombinant $^{125}$I-TGF-β1 precursor (1.3×10$^5$ cpm) (FIG. 36B) and where indicated, either 5 mM man6P or 100 nM IGF-II was included to assess non-specific binding. Results are averages of triplicate determinations.

Figure 37A:
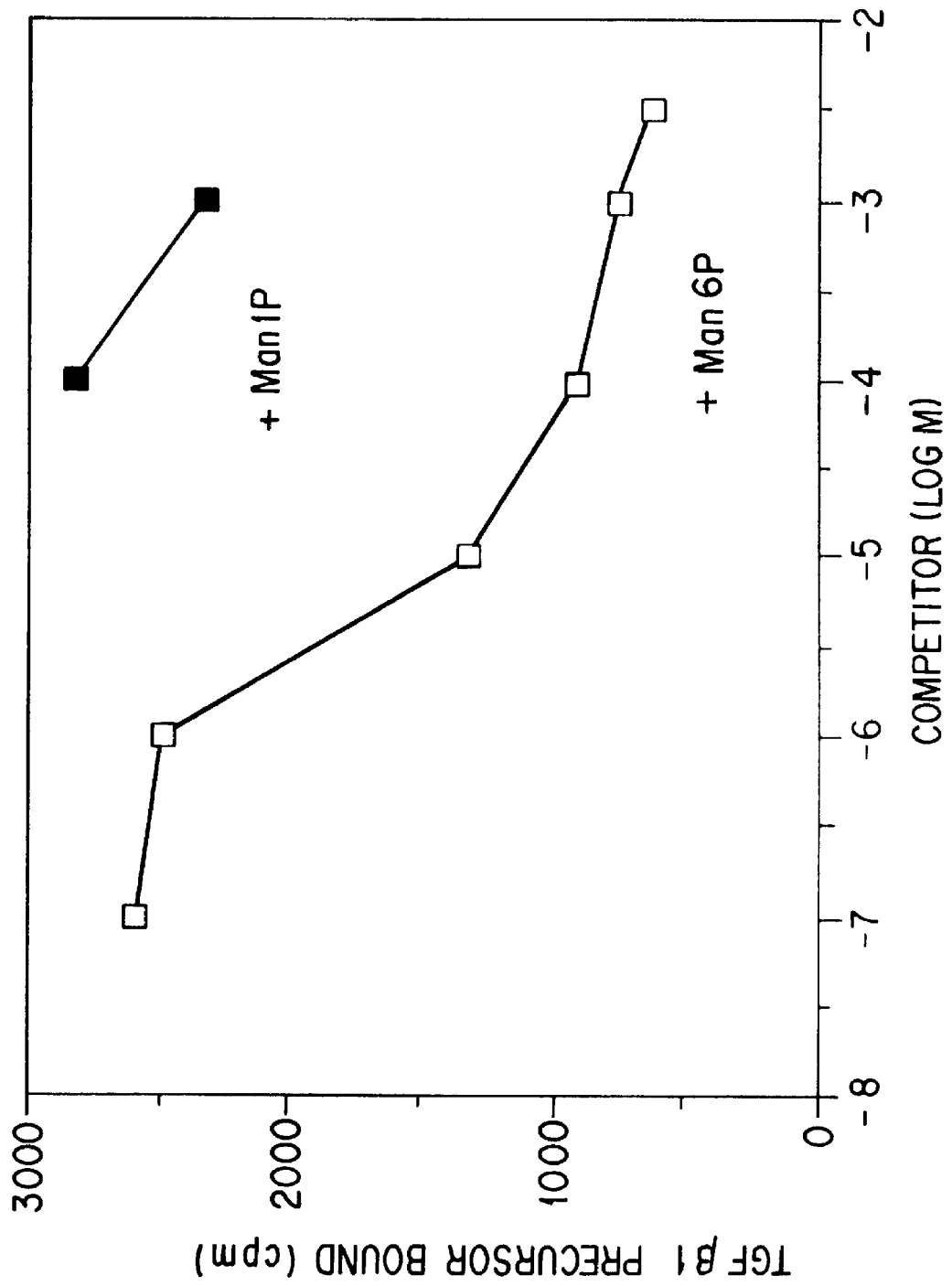
Figure 37B:
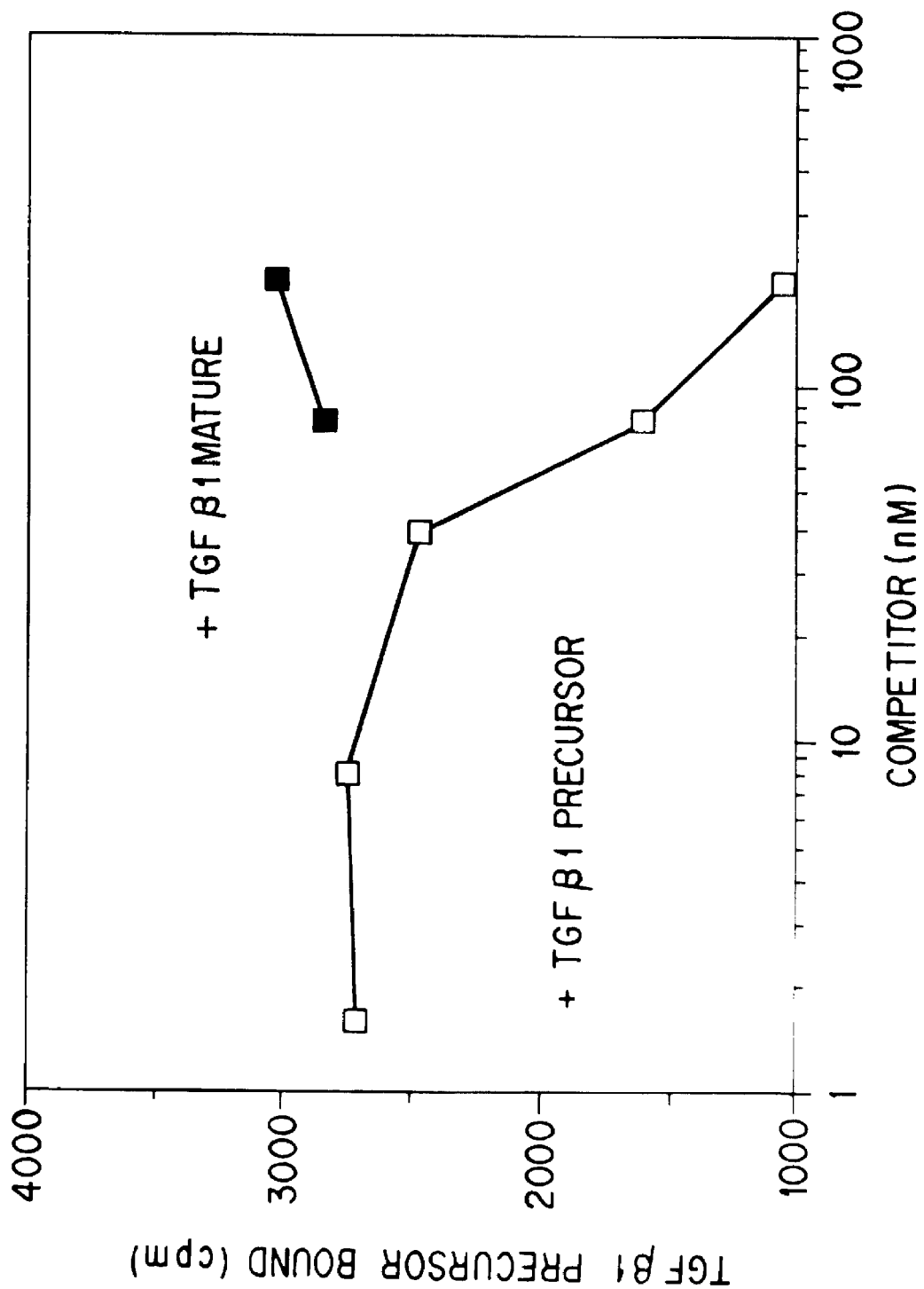

FIGS. 37A and 37B. Specificity of recombinant TGF-β1 precursor binding to CHO cells overexpressing the human IGF-II/man6P receptor. Cells were incubated with recombinant $^{125}$I-TGF-β1 precursor (6.7×10$^4$ cpm) and the indicated concentration of competing unlabeled ligand. FIG.37A (+Man 1P, +Man 6P), FIG. 37B (+TGFβ1 mature, +TGFβ1 precursor).Results are averages of triplicate determinations.

Figure 38:
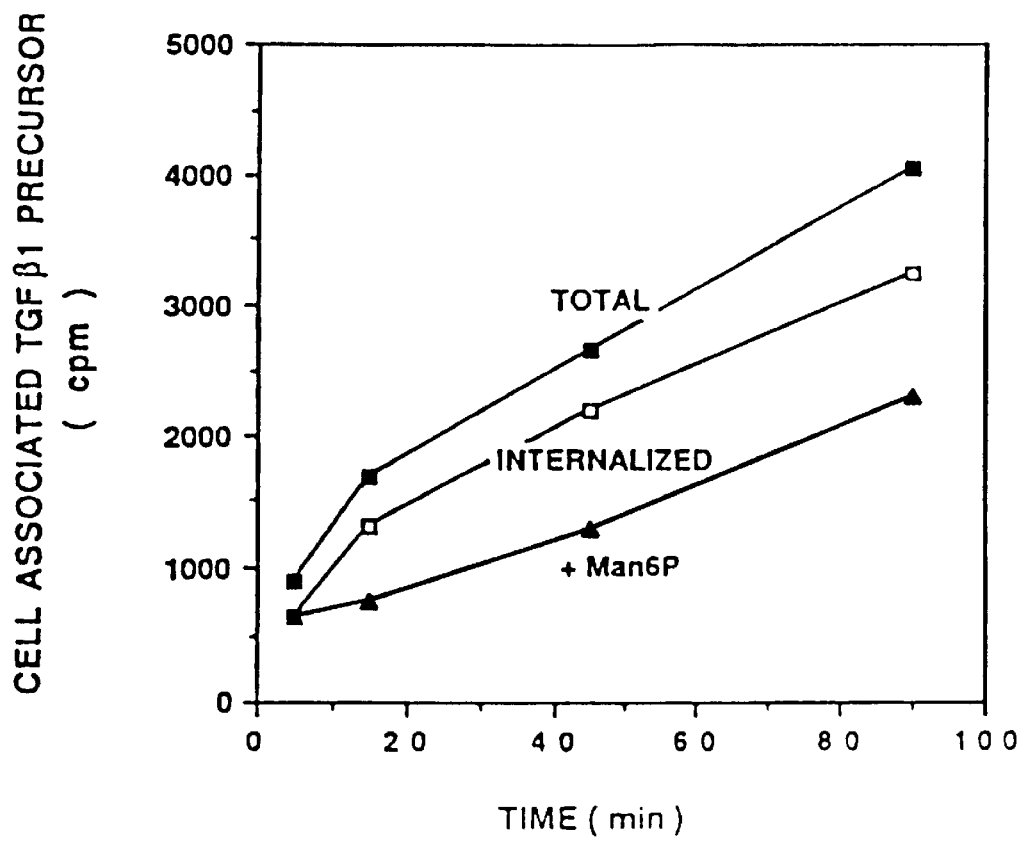

FIG. 38. Internalization of recombinant TGF-β1 precursor. CHO cells overexpressing the IGF-II/man6P receptor were incubated at 37° C. with recombinant $^{125}$I-TGF-β1 precursor (5×10$^4$ cpm) in the presence or absence of 5 mM man6P. At the indicated times, either the total or the acid-resistant (i.e., internalized) cell associated counts were determined. Results are averages of triplicate determinations.

Figure 39:
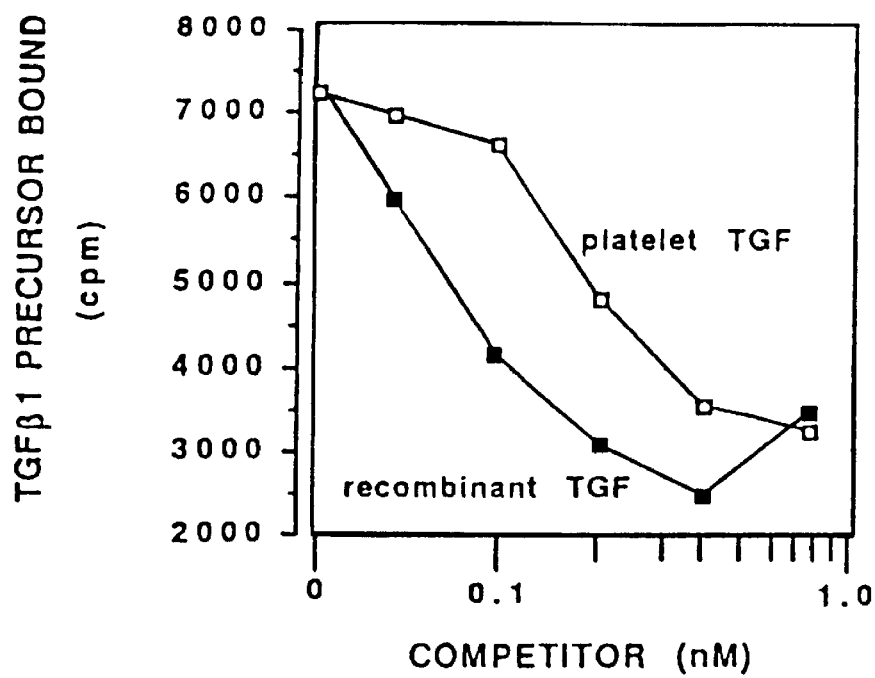

FIG. 39. Binding of the platelet TGF-β1 precursor to the isolated IGF-II/man6P receptor. Purified IGF-II/man6P receptor adsorbed to microtiter wells was incubated with $^{125}$I-labeled recombinant TGF-β1 precursor in the presence of the indicated concentrations of either purified latent TGF-β1 from platelets (□) or the recombinant TGF-β1 (■). After 3 h at 4° C., the amount of receptor-bound radioactivity was determined.

Figure 40A:
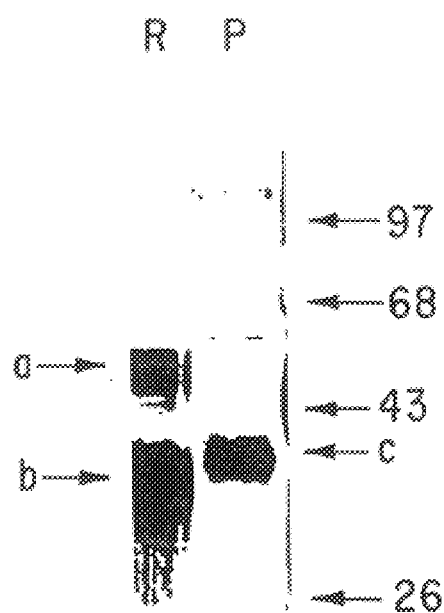
Figure 40B:
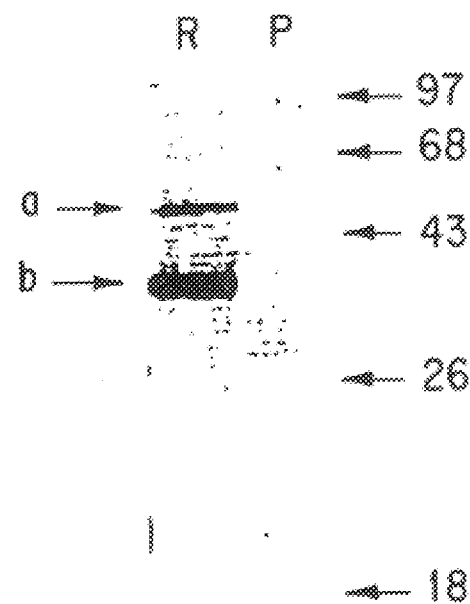

FIGS. 40A and 40B. Binding of the IGF-II/man6P receptor to recombinant TGF-β1 precursor but not platelet TGF-β1: Western blot analysis. Recombinant (R) (0.5 μg) and platelet (P) TGF-β1 precursor (2.5 μg) were electrophoresed on a reduced, SDS polyacrylamine gel, transferred to a nitrocellulose filter and reacted with either anti-peptide antibodies specific for a sequence in the precursor (FIG. 40A) or with the IGF-II/man6P receptor and antibodies to the receptor (FIG.40B). The presence of bound rabbit antibodies was detected with alkaline phosphatase conjugated to anti-rabbit Ig and a histochemical stain for alkaline phosphatase. The position of molecular weight markers (in kilodaltons) are indicated by arrows. The positions of the recombinant uncleaved precursor (a), recombinant precursor remnant (b), and platelet precursor remnant (c) are also indicated.

Figure 41:
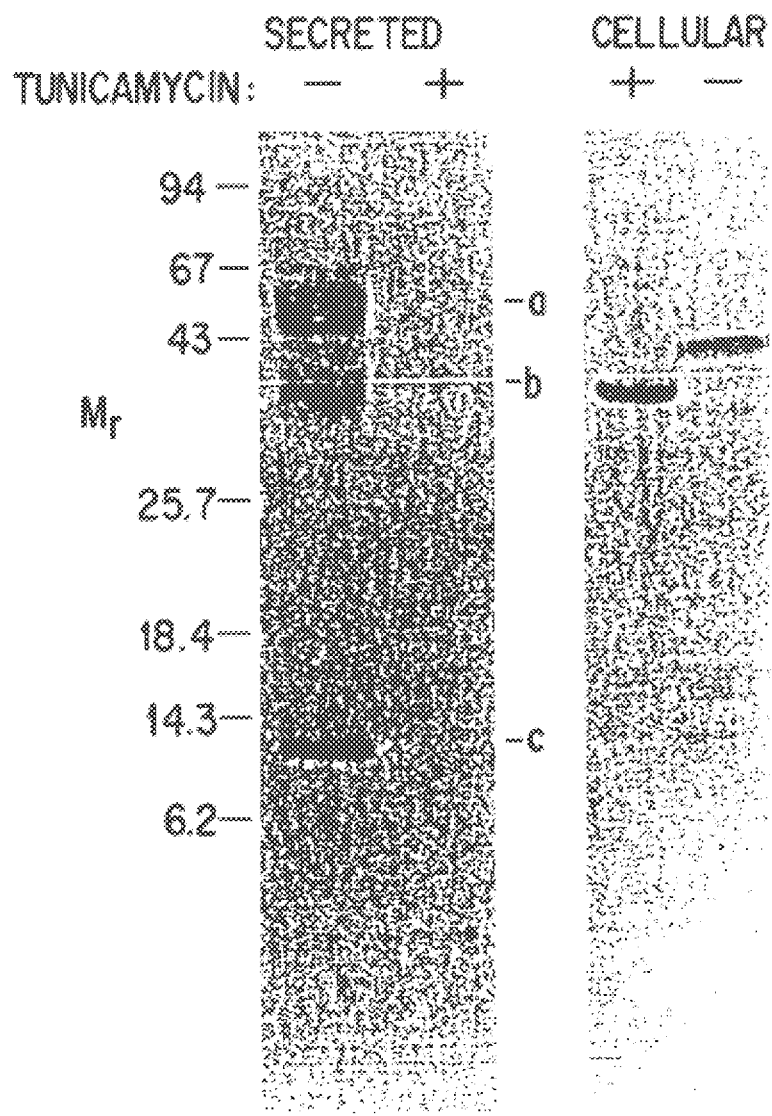

FIG. 41. Identification of immunoreact:ive TGF-β1 from tunicamycin (TU) treated CHO cells and from untreated CHO cells. Cells grown to confluency in complete culture medium were treated with 2.5 μg/ml TU at a final dimethyl sulfoxide concentration of 0.1% (v/v) for 4h. Serum-free medium containing TU was then added and collected after 24 h. Control cells received only 0.1% (v/v) dimethyl sulfoxide. For secreted proteins, the medium was dialyzed against 0.1M acetic acid, dried and analyzed by immunoblotting. The letters a, b and c denoted at the center of the immunoblot indicate the three forms of TGF-β1. This immunoblot represents proteins secreted from 2×10$^5$ cells into 1 ml of medium. For the cellular associated form of TGF-β1, 5×10$^5$ cells were collected and analyzed by immunoblotting. The antibodies utilized were a mixture of precursor- and mature-specific antipeptide antibodies (Section 7.1.8., infra).

Figure 42A:
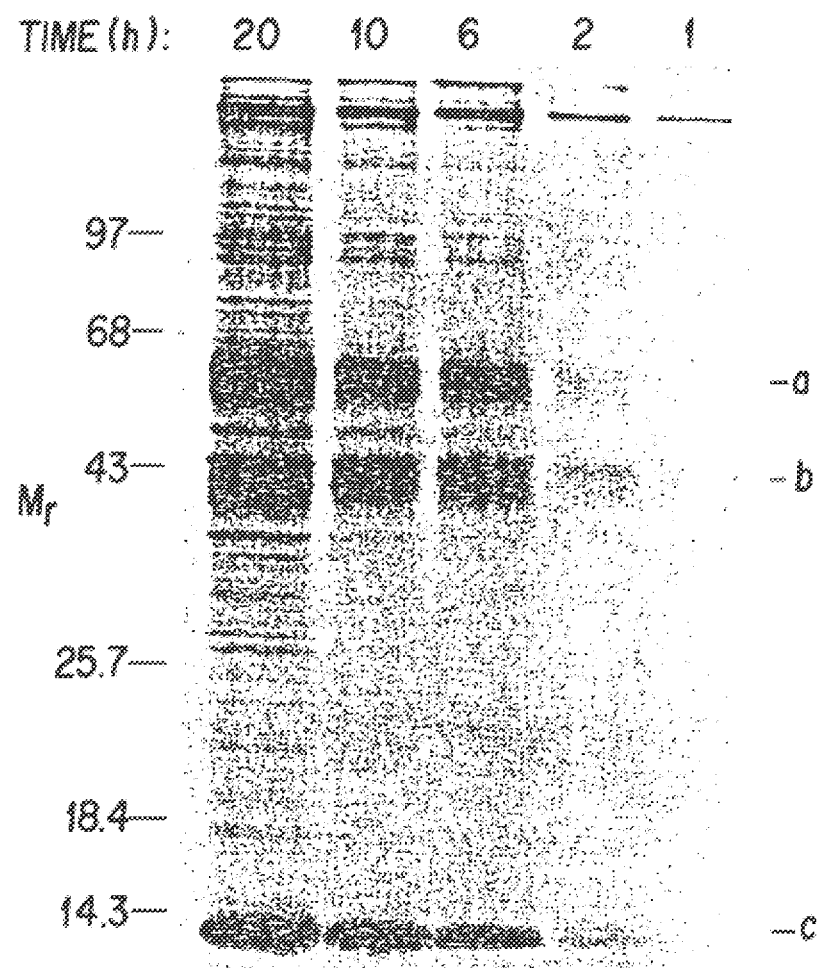
Figure 42B:
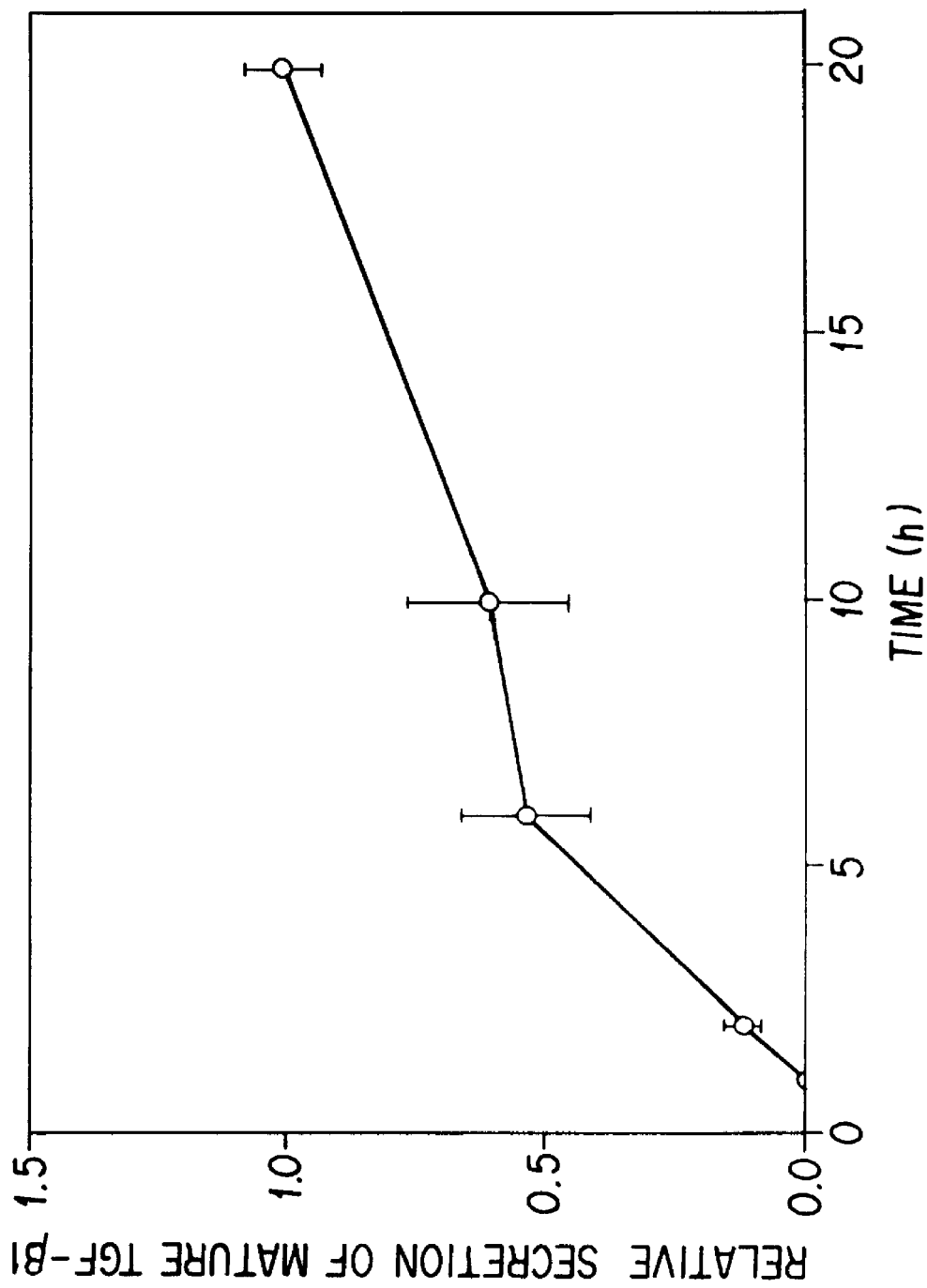

FIGS. 42A and 42B. Time course for secretion of TGF-β1 by transfected CHO cell line TGF-β3-2000 clone 17. FIG. 42A: SDS-PAGE of conditioned medium collected at various times from pulse labeled CHO cells. Cells were pulse labeled for 0.5 h with a combinations of [35-S]-cysteine and [35-S]-methionine. The medium was fractionated on a 7.5–20% gradient SDS-polyacrylamide gel under reducing conditions. Marker proteins (kDal) are located to the right of the figure. FIG. 42B: Quantitation of TGF-β1 secreted from the CHO cells at various chase times. Since the ratio of mature TGF-β1 to the amount of TGF-β1 precursor was invariant during secretion, relative levels of recombinant growth factor secreted were measured by densitometric scans of the 12 kDal TGF-β1 observed in the flourographs. Each point represents the mean of triplicate experiments and includes standard deviation. The relative amount of mature TGF-β1 secreted at 20 h was considered as 1.0.

Figure 43A:
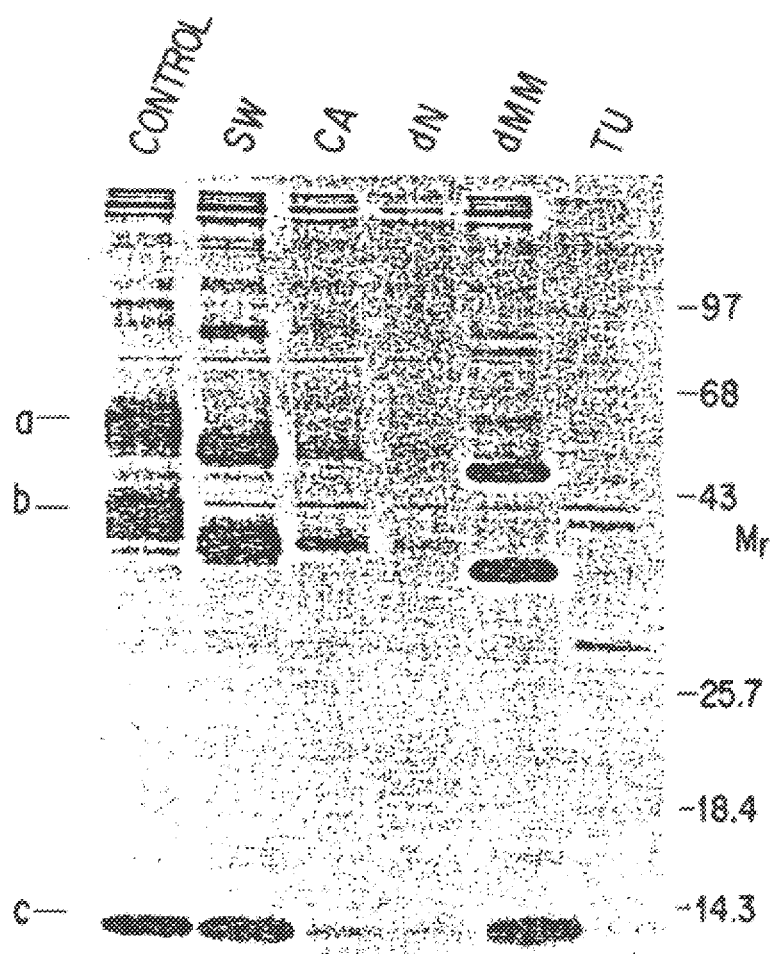
Figure 43B:
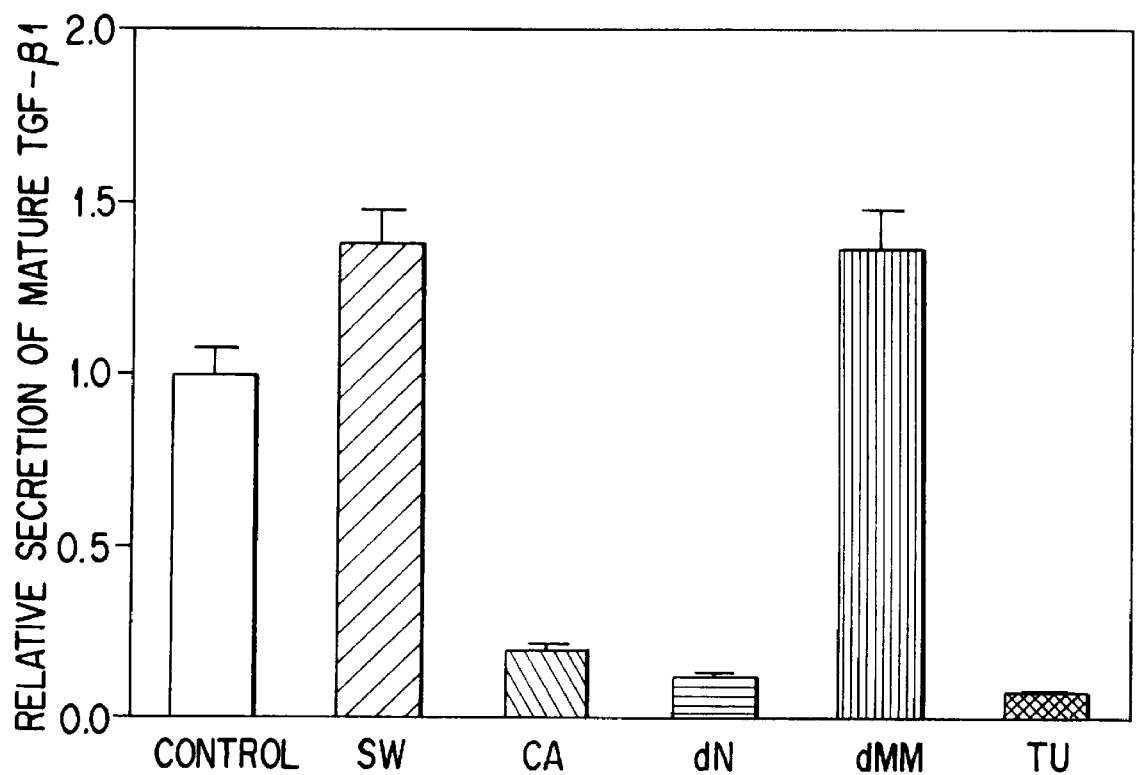

FIGS. 43A and 43B. Effects of glycoslylational inhibitors on secretion of TGF-β1 in CHO cells. FIG. 43A: Confluent cultures of cells were incubated in medium lacking serum, methionine, and cysteine for 1 h prior to a 0.5 h pulse labeling with [35-S]-cysteine and -methionine. Inhibitors were utilized at the following concentrations; 0.23 mM SW, 0.52 mM CA, 4 mM dN, 4 mM dMM and 6 μM TU. Following a 6 h chase, conditioned medium was fractionated on SDS-polyacrylamide gels and flourographed. Markers are identical to those described in FIG. 41. FIG. 43B: Quantitation of recombinant growth factor secreted by CHO cells following treatment with the inhibitors. The relative amount of growth factor was determined by densitometric scans of the flourographs. Results are from 3 independent experiments with standard deviations illustrated. The relative amount of mature TGF-β1 in control CHO cells was considered as 1.0.

Figure 44A:
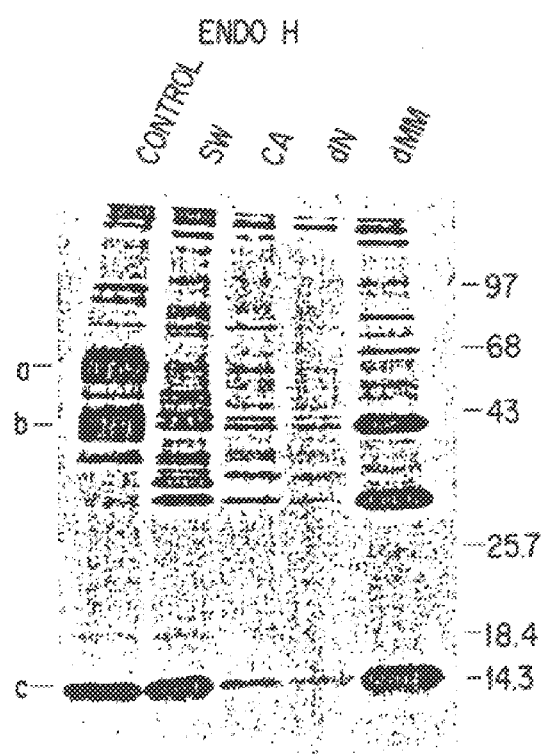
Figure 44B:
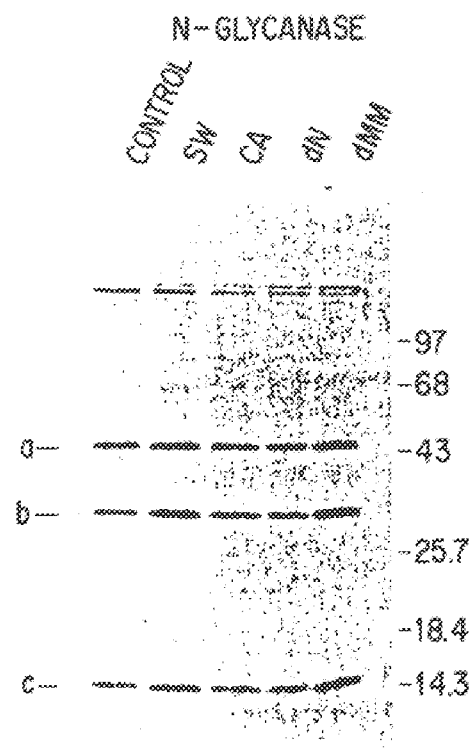
Figure 44C:
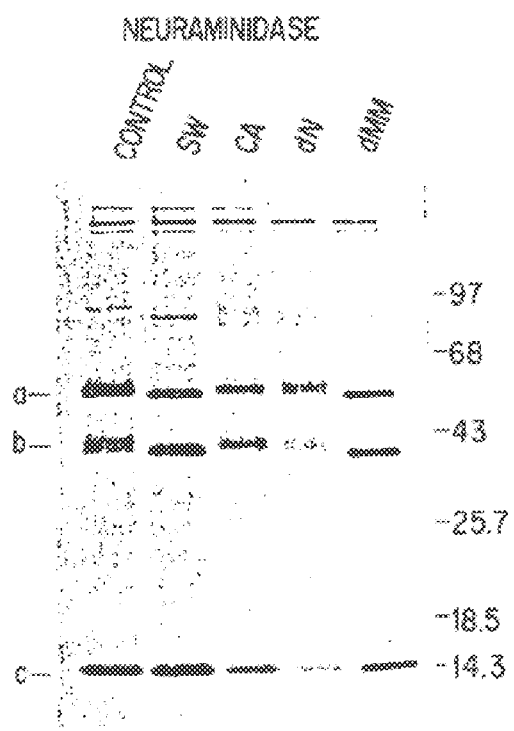

FIGS. 44A–44C. Digestion of secreted TGF-β1 proteins from inhibitor-treated cells with glycosylational trimming enzymes. Conditioned culture medium from the transfected CHO cells labeled with [35-S]-methionine and -cysteine were collected after a 6 h chase and digested with endo H (FIG. 44A), neuraminidase (FIG. 44C), or N-glycanase (FIG. 44B). The digestion products were fractionated on reducing 7.5–20% gradient polyacrylamide gels and flourographed. Markers designated at the left and right of the flourographs are identical to those described in FIG. 41.

Figure 45:
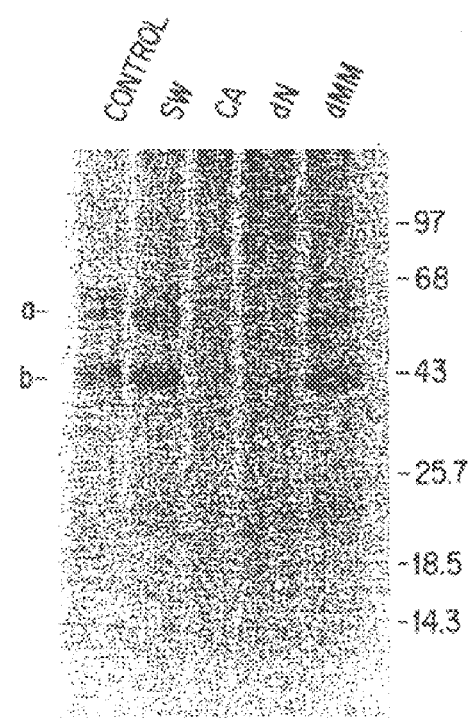

FIG. 45. Phosphorylation of TGF-β1 precursors from CHO cells treated with the glycosylational inhibitors. Confluent cultures of TGF-β3-2000 clone 17 CHO cells were labeled with [32-P]-orthophosphate and processed as described in Section 12.1., et seq. herein. The labeled culture medium was collected and excess [32-P]-orthophosphate removed by a Sephadex G-25 desalting column. 32-P-Labeled proteins were fractionated by reducing SDS-PAGE and autoradiographed. Marker proteins (KDal) are located to the right of the autoradiograph and the letters "a" and "b", which are shown to the left, represent the TGF-β1 precursor polypeptides.

Figure 46A:
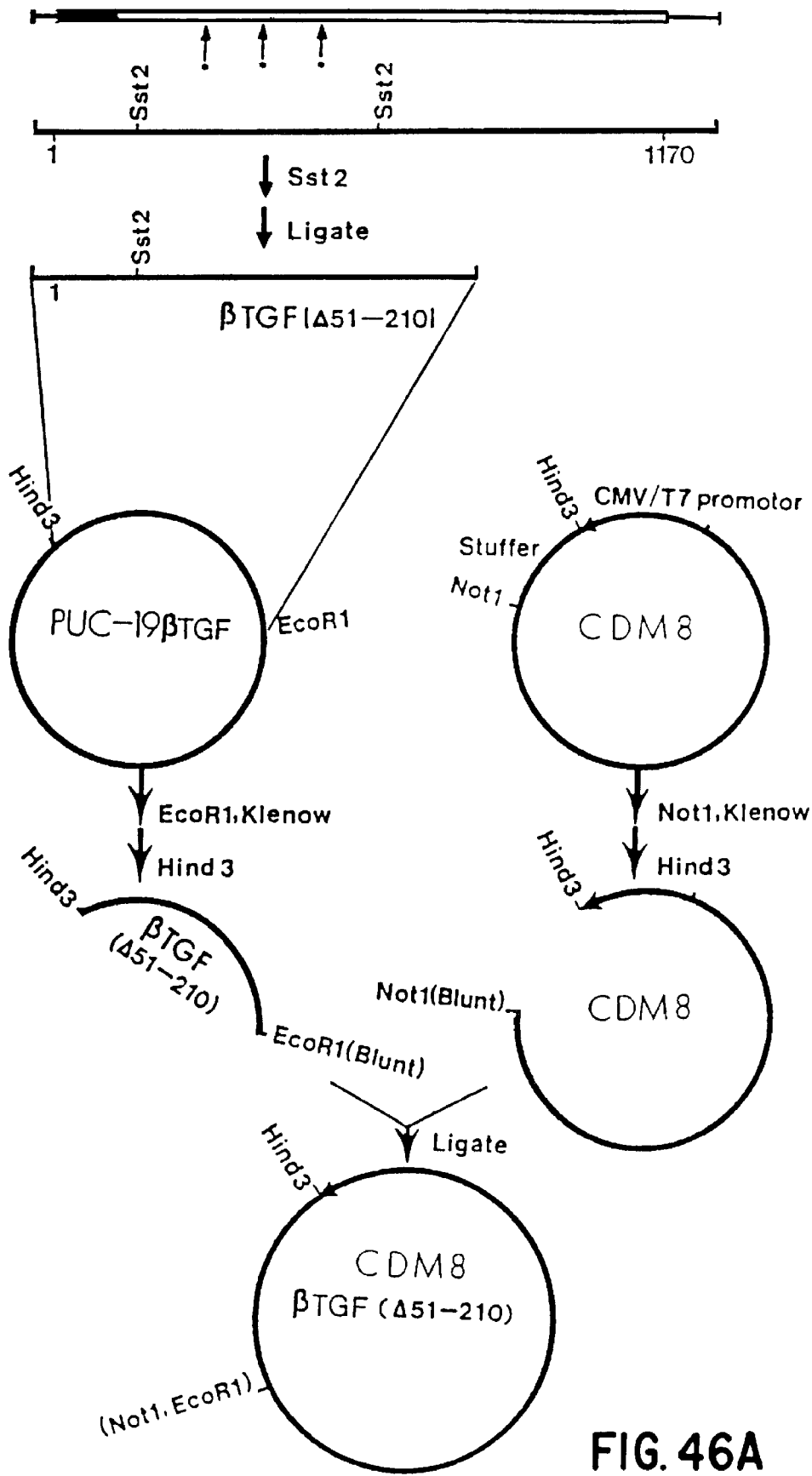
Figure 46B:
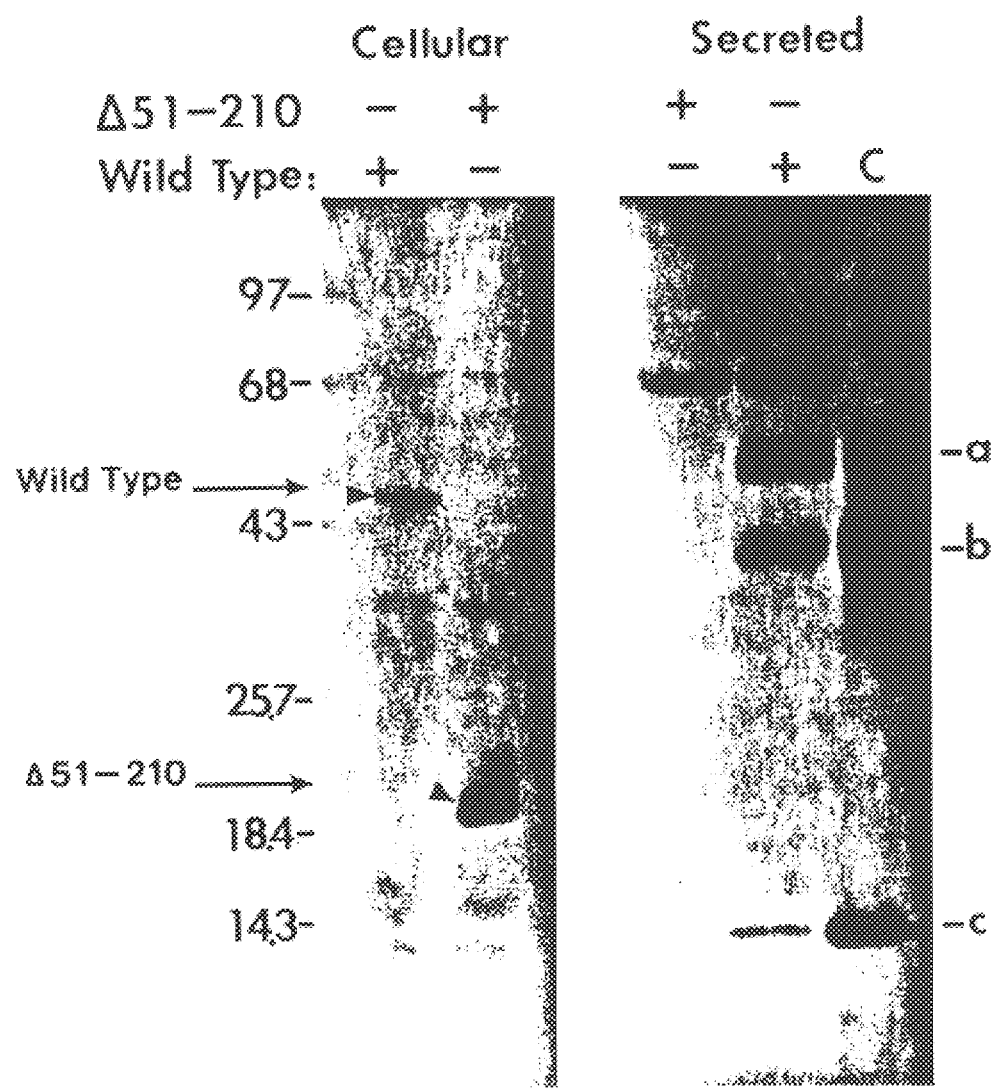

FIGS. 46A and 46B. Deletion mutant lacking the three glycosylational signals is not secreted from cells. FIG. 46A: Diagram for the construction of a deletion mutant of TGF-β1 lacking the glycosylational signal sequences and its insertion into the transient expression plasmid CDM8. Sac II was utilized to remove DNA coding for the three glycosylational sequences of TGF-β1. This deletion results in the in frame removal of 160 amino acids; the mutant protein is fused between Arg-50 and Gly-211 using the numbering nomenclature of Sharples et al. and will be referred to as Δ51–210 TGF-β1. FIG. 46B: Transient expression of Δ51-210 TGF-β1 in Cos-1 cells. Cos-1 cells were grown to semiconfluency and transfected with CDM8 containing the Δ51-210 TGF-β1 cDNA insert. Transfection conditions were as described in Section 12.1.7., infra. 48 h after the transfection, the cells were incubated in medium lacking serum and collected 48 h later. Conditioned medium was dialyzed against 0.1M acetic acid, dried and analyzed by immunoblotting using precursor- and mature-specific antipeptide antibodies to TGF-β1.

Figure 47A:
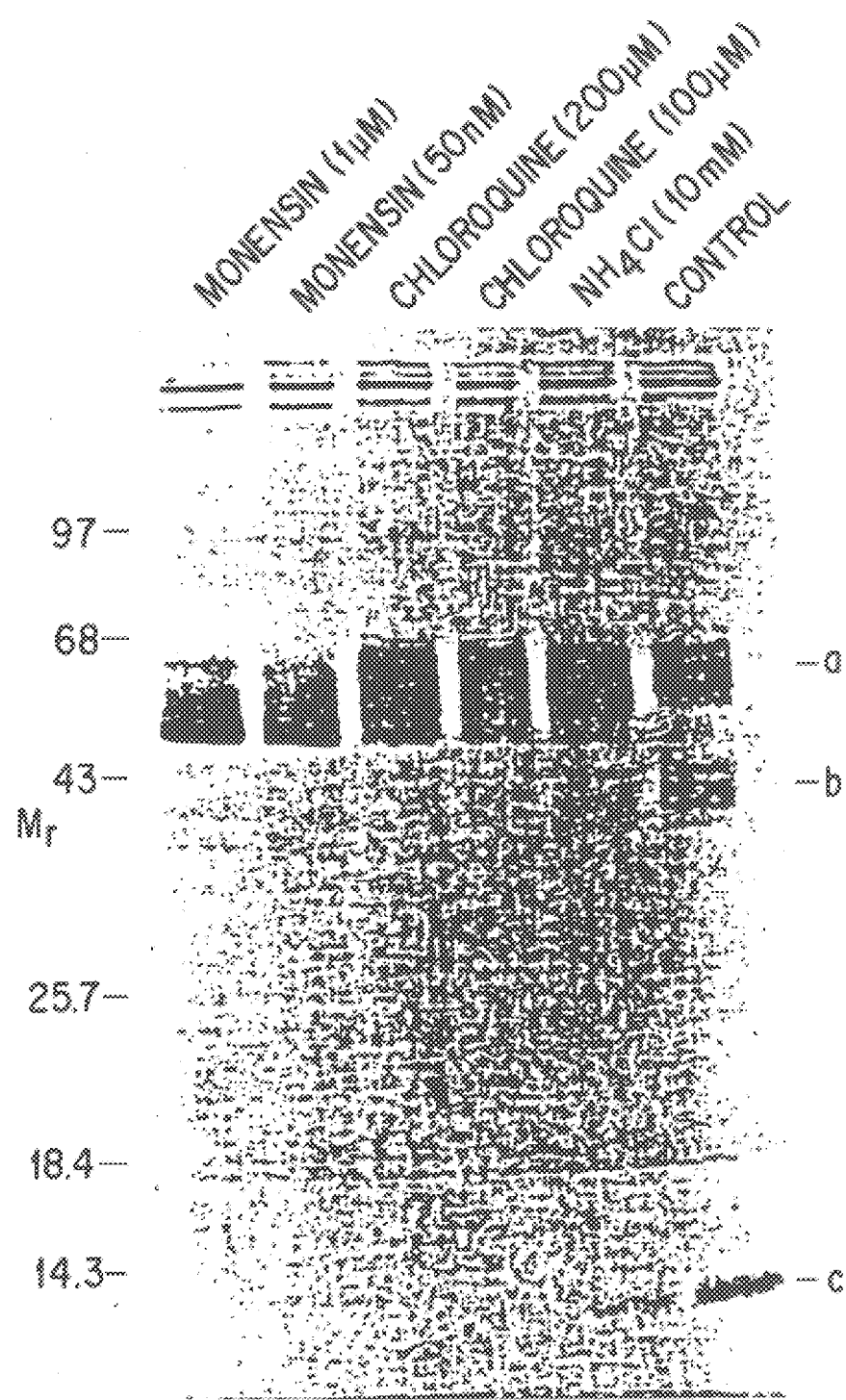
Figure 47B:
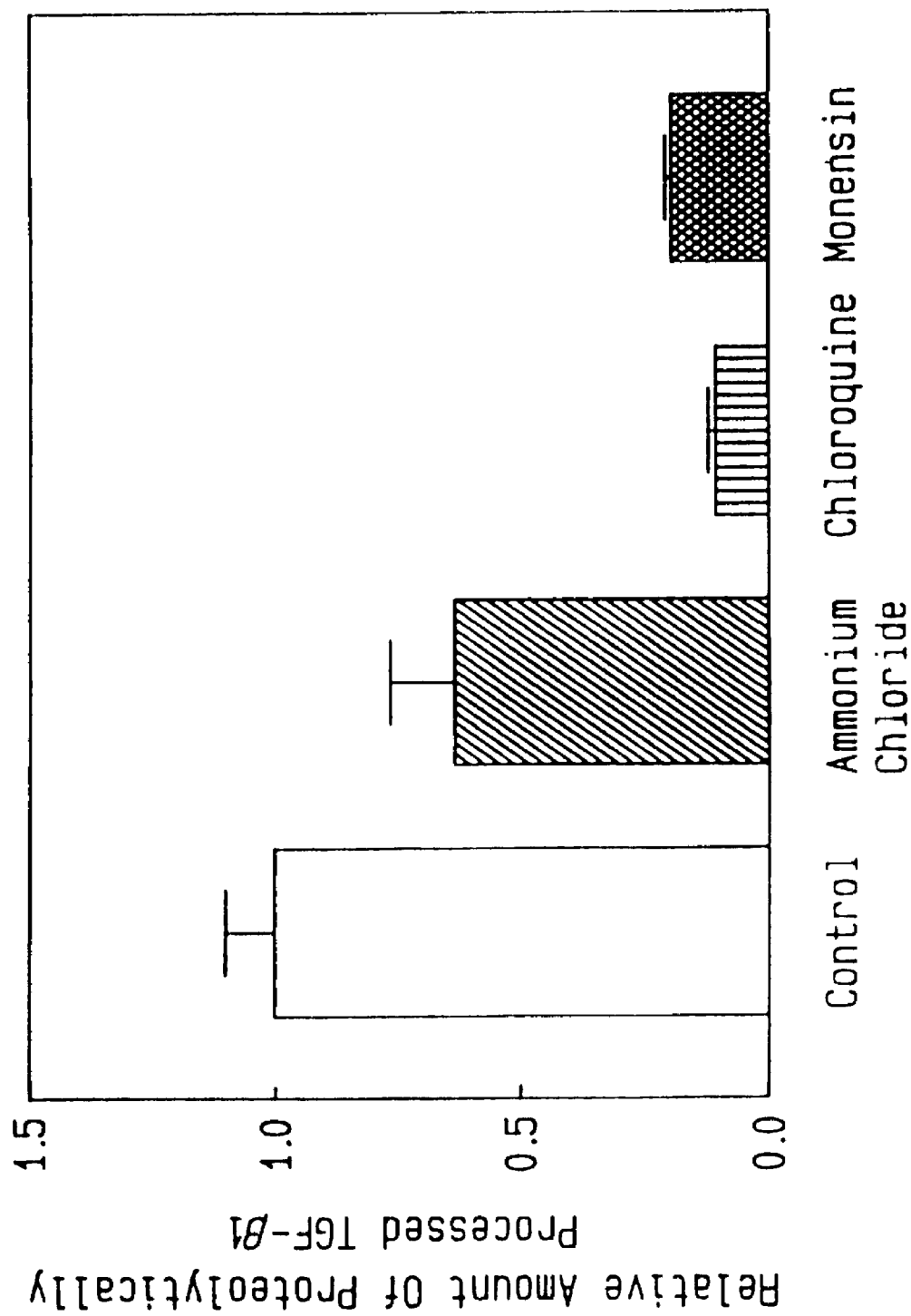

FIG. 47. Ionophores or weak bases, which affect the intra-lysosomal pH, inhibit the proteolytic processing of the TGF-β1 molecule in CHO cells. FIG. 47A: SDS-PAGE analysis of conditioned medium collected after a 6 h chase. Cells were treated at the concentrations indicated. Markers at the left and right of the figure are identical to those shown in FIG. 41. FIG. 47B: Quantitative assessment of proteolytic processing of the secreted TGF-β1 molecules. For these experiments, cells were treated with 200 μM chloroquine, 1 μM monensin or 10 mM ammonium chloride. The relative amounts of recombinant growth factor were calculated from densitometer scans of the fluorograph by summing the total TGF-β1 secreted and normalizing the levels of the recombinant growth factor. After normalization, the amount of mature TGF-β1 present was determined by densitometry and indicated the level of proteolytic processing. Each point represents three independent experiments and includes the standard deviation. The relative processing of recombinant TGF-β1 from control cells is treated as 1.0.

Figure 48:
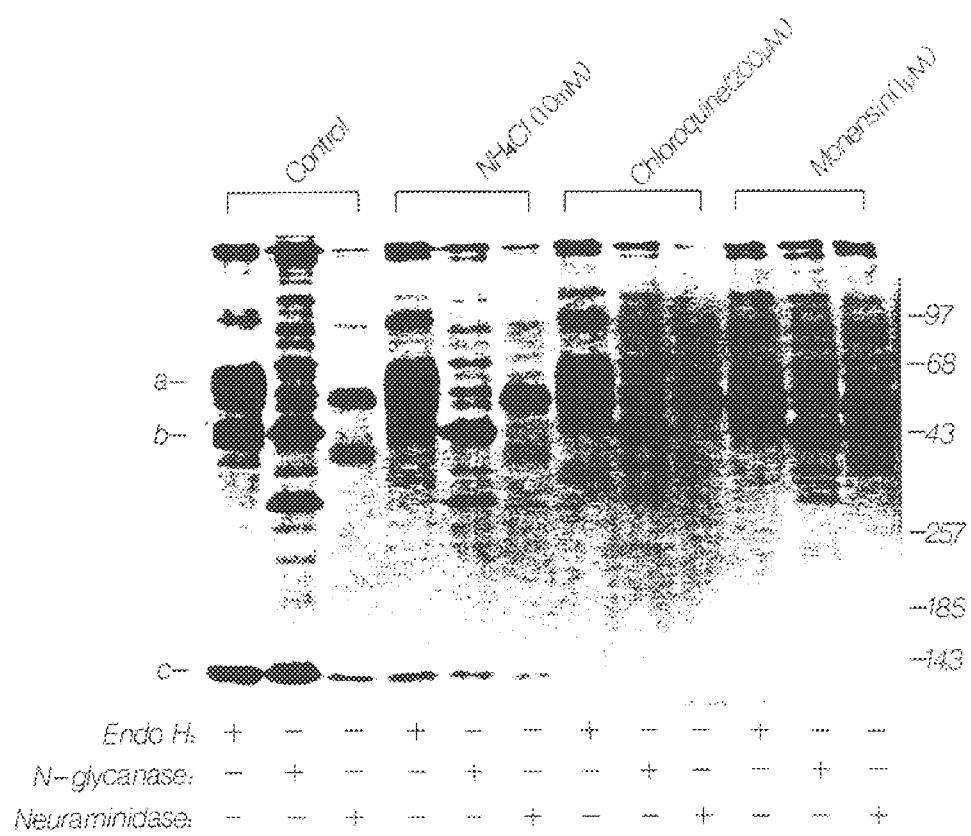

FIG. 48. Glycosidase treatment of recombinant TGF-β1 polypeptides secreted from CHO cells which had been treated with chloroquine, monensin, and ammonium chloride. Conditioned medium from TGF-β3-2000 clone 17 cells pulse labeled and incubated with ammonium chloride (10 mM), chloroquine (200 μM) or monensin (1 μM) were treated with Endo H, neuraminidase, or N-glycosidase. The digestion products were analyzed by SDS-PAGE and flourography. Markers were as described in FIG. 41.

Figure 49:
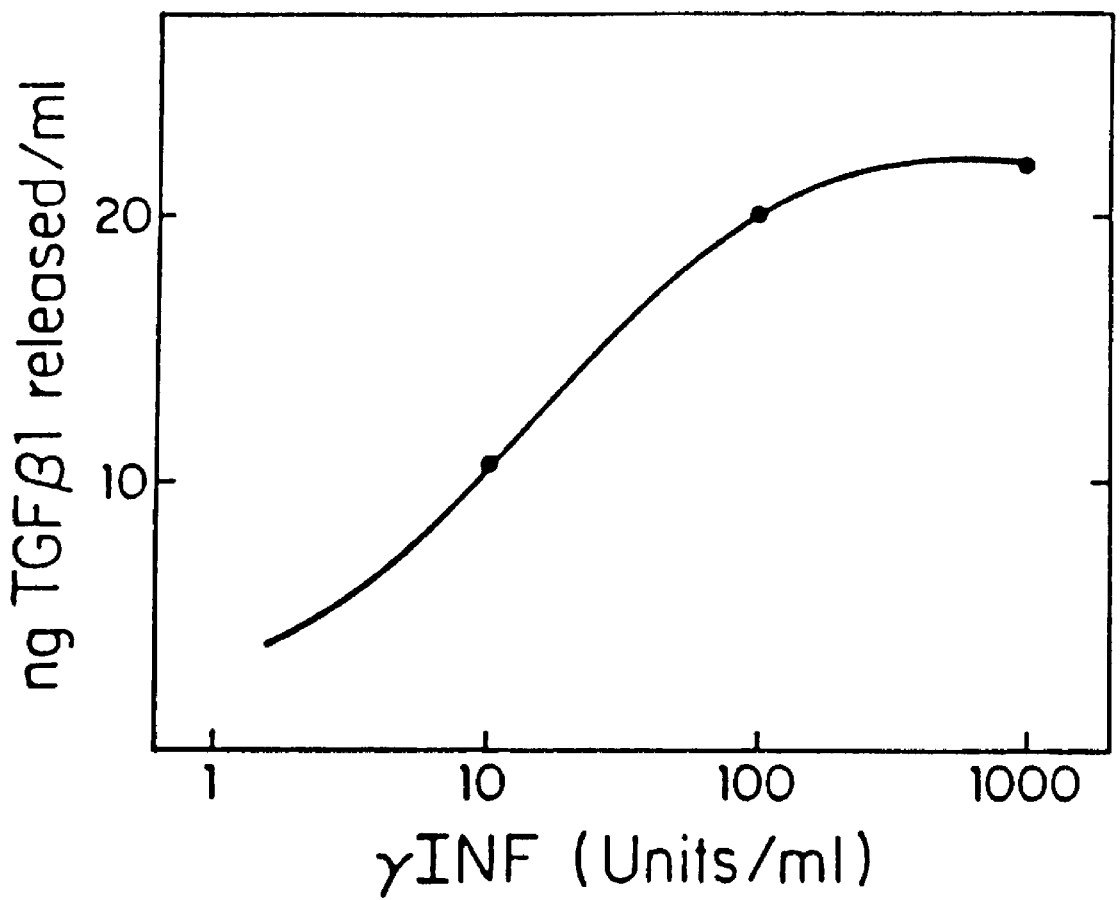

FIG. 49. Gamma interferon-induced activation of LnTGF-β1 by monocytes is dose dependent. Monocytes ($2 \times 10^6$ cells/ml) were cultured in Costar 96-well microtiter plates with 5 μg/ml of purified latent rTGF-β1 (LnTGF-β1), in the absence (control) or presence of increasing concentrations of rγINF from 10 to 1000 U/ml. Cytokine was added to culture wells simultaneously with Ln TGF-β1 and supernatants were harvested 24 hrs later and assayed for TGF-β activity using the growth inhibition assay described in Section 7.1.6., infra.

Figure 50:
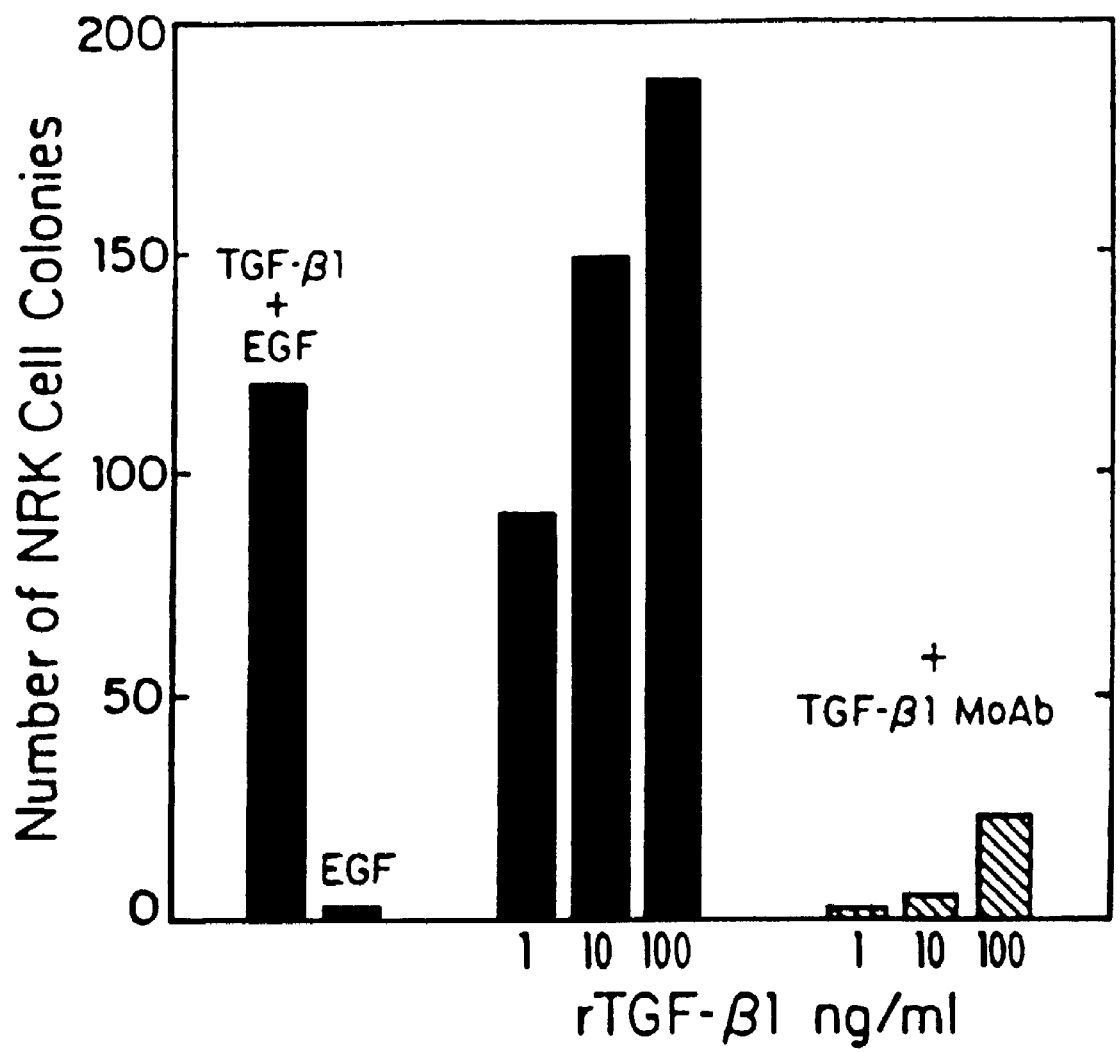

FIG. 50. Functional identity of γINF-mediated, monocyte-activated TGF-β1 with platelet-derived TGF-β. Serum-free 24 hr supernatants were harvested from monocytes cultured in the presence of 100 U/ml of rγINF and 5 μg/ml of LnTGF-β activity was quantiated in pooled samples by testing in triplicate serial dilutions in the growth inhibition assay described in Section 7.1.6., infra, using a known TFG-β platelet standard. Log dilutions of monocyte-activated TFG-β (1, 10, 100 ng) were then tested in normal rat kidney (NRK) cell anchorage independent growth assay (Twardzik et al., 1982, Science 216: 894–897) in the presence or absence of 30 ug/ml of a neutralizing monoclonal antibody, ID 11.16, made against bovine TFG-β1 as previously described (Dasch et al., 1989, J. Immunol. 142: 1536–1541. Colonies larger than 20 cells were scored in 8 random low power fields.

Figure 51:
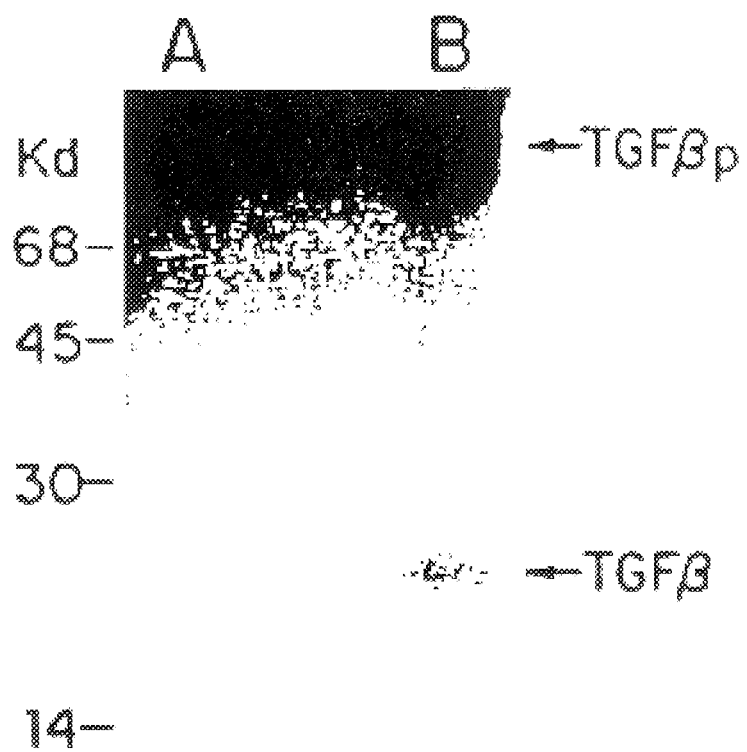

FIG. 51. SDS-PAGE analysis of γINF-induced, monocyte-activated TGF-β1. Cells derived from the parental TGF-β3-2000 cell line were incubated overnight in serum-free DMEM containing 3H-leucine (Amersham L-C4,5-3H); 45–70 Ci/mM, 0.5 mCi/ml. Supernatants were harvested and $^3$H-leucine labeled LnTFG-β1 complex was purified as described in Section 13.1.1., infra. Monocytes ($1 \times 10^7$ cells/ml) were incubated in DMEM containing 0.5% human serum with $1.6 \times 10^6$ cpm of $^3$H-leucine labeled TFG-β1p complex in the presence or absence of 100 U/ml of rγ-INF for 12 hr, supernatants were clarified and analyzed by SDS-PAGE (12.5%) under non-reducing conditions. Markers included bovine serum albumin, 68 kd; ovalbumin, 45 kd; carbonic anhydrase, 30 kd; cytochrome C, 14 kd and TGF-β, 24 Kd, and were visualized by silver stain (Dasch et al., 1989, J. Immunol. 142: 1536–1541). $^3$H-leucine labeled protein was detected by autoradiography on Kodak X-omat AR film with lightening plus intensifying screen. Lane A, monocytes plus γ-INF, lane B, monocytes without γ-INF.

5. DESCRIPTION OF THE INVENTION

The present invention relates to the production of a biologically active, mature form of rTGF-β1 from the simian TGF-β1 precursor gene coding sequence and its product. The mature biologically active TGF-β1 may be produced by the cloning and expression of the full-length nucleotide coding sequence of simian TGF-β1 in a host cell which processes the precursor correctly so that a mature rTGF-β1 is produced, which has a biological activity that is virtually indistinguishable from that of authentic natural TGF-β1.

The present invention also relates to a biologically active rTGF-β1 precursor protein which can be produced using the simian TGF-β1 precursor gene. Biologically active rTGF-β1 precursors may be produced by the cloning and expression of the full-length nucleotide coding sequence of simian TGF-β1 in an appropriate host cell capable of secreting the TFG-β1 precursors.

The method of the invention may be divided into the following stages solely for the purposes of description: (a) isolation or generation of the coding sequence for the precursor form of simian TGF-β1; (b) construction of an expression vector which will direct the expression of the simian TGF-β1 coding sequence; (c) transfection of appropriate host cells which are capable of replicating and expressing the gene and processing the gene product to produce the mature biologically active form of TGF-β1 and/or TGF-β1 precursors; and (d) identification and purification of the TGF-β1 precursors and the mature, biologically active TGF-β1.

Once a transfectant is identified that expresses high levels of TGF-β1 precursors and/or bioactive, mature TGF-β1, the practice of the invention involves the expansion of that clone and isolation of the gene product expressed.

The method of the invention is demonstrated herein, by way of examples in which the cDNA of the simian TGF-β1 precursor coding region was prepared, cloned, and sequenced. The coding region was then placed under the control of SV40 expression control elements and used to transfect CHO cells. The CHO transfectants produced a mature rTGF-β1 with biological activity that was indistinguishable from that of natural TGF-β1 as well as larger biologically active precursor forms.

The various aspects of the method of the invention are described in more detail in the subsections below and in the examples that follow.

5.1. ISOLATION OR GENERATION OF THE SIMIAN TGF-β1 CODING REGION

The nucleotide coding sequence for simian TGF-β1 is depicted in FIG. 1. In the practice of the method of the invention, this nucleotide sequence, or its functional equivalent can be used to generate the recombinant molecules which will direct the expression of the TGF-β1 product. Due to the degeneracy of the nucleotide coding sequences, other DNA sequences which encode substantially the same amino acid sequence as depicted in FIG. 1 may be used in the practice of the present invention for the cloning of TGF-β1. Such alterations of the nucleotide sequence of FIG. 1 include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

The nucleotide coding sequence for TGF-β1 may be obtained from simian cell sources that produce high levels of TGF-β1-like activity. The coding sequence may be obtained by cDNA cloning of RNA isolated and purified from such cellular sources or by genomic cloning. Either cDNA or genomic libraries of clones may be prepared from the DNA fragments generated using techniques well known in the art including but not limited to the use of restriction enzymes. The fragments which encode TGF-β1 may be identified by screening such libraries with a nucleotide probe that is substantially complementary to any portion of the sequence depicted in FIG. 1. Full length clones, i.e., those containing the entire coding region for the TGF-β1 precursor may be selected for expression.

In an alternate embodiment of the invention, the coding sequence of FIG. 1 could be synthesized in whole or part, using chemical methods well known in the art.

In the examples described herein, the simian TGF-β1 coding sequence was obtained by cDNA cloning of the TGF-β1 precursor coding sequence derived from polyadenylated RNA isolated from the African green monkey cell line, BSC-40, which had been shown to produce high levels of a growth inhibitor functionally related to TGF-β1. The entire coding region was sequenced and compared to the published sequences of human and murine TGF-β1 (see FIG. 1). The deduced amino acid sequence of the mature simian TGF-β1 demonstrates 100% homology with that of mature human TGF-β1. The precursor sequences also demonstrate strong sequence homology with only five amino acid differences between the human and simian precursor sequences. Interestingly, the simian (and murine) precursor sequence encode one less amino acid residue than the sequence reported for human TGF-β1 (see FIG. 1, amino acid residue numbers 158–159).

The remarkable conservation in the sequence of TGF-β1 between simian, rodent and human species suggests that strong evolutionary pressure was required, by necessity, to conserve important functionality. This applies not only to the mature form of TGF-β1, which has an important bi-functional role as a growth regulator, but also to the polypeptide region of the precursor upstream of the mature TGF-β1 sequence which may also exhibit coordinate growth modulatory activities.

The major TGF-β1 mRNA species in BSC-40 cells is 2.5 kb, in agreement with results obtained for murine and human TGF-β1 specific messages (FIG. 2). The minor bands seen at 4 kb and 1.45 kb may represent either aberrantly processed transcripts or may code for a TGF-β1 like molecule (CIF-B) recently described by Seyedin (1987, J. Biol. Chem. 262: 1946–1949) which contains extensive homology to TGF-β1.

The deduced polypeptide sequence of the simian, human, and mouse clones contain a nearly identical contiguous stretch of 14 hydrophobic residues in positions 8–21 which may constitute an amino terminal signal peptide. In addition, an Arg-Arg dipeptide immediately preceeds the amino terminus of mature TGF-β1 suggesting similar proteolytic cleavage sites. The simian TGF-β1 precursor also contains three potential N-glycosylation sites not found in the mature molecule. Thus, not only has the primary structure of the mature and precursor polypeptide of TGF-β1 been conserved among species, but distinct post translational modification sites as well.

BSC-40 cells synthesize and release high levels of TGF-β1 relative to other cell lines we have tested. Media conditioned by BSC cells contain an activity which in the presence of nanogram levels of EGF and TGF-alpha stimulates the anchorage independent growth of NRK cells and exhibits biochemical characteristics identical to TGF-β1 purified from human platelets (Frolik et al., 1983, Proc. Natl. Acad. Sci. USA 80:3676–3680; Roberts et al., 1983, Biochemistry 22:5692–5698). In addition, the isolation of a growth inhibitor from BSC-1 cells functionally similar to TGF-β1 which competes with platelet derived TGF-β1 for binding to TGF-β1 membrane receptors has been described (Tucker et al., 1984, Science 226:705–707). The large amount of TGF-β1 specific mRNA synthesized by BSC-40 cells, a cell line derived from BSC-1 cells, suggests that the bifunctional growth modulator identified by Tucker et al. in BSC-1 conditioned media is indeed TGF-β1. This is also supported by recent data which confirms Tucker et al.'s observations that TGF-β1 from other sources also inhibits the growth of some tumor cells in culture (Roberts et al., 1985, Proc. Natl. Acad. Sci. USA 82:119–123). However, formal proof that the BSC-1 derived inhibitor is indeed the product of the gene described herein will require sequence analysis of the TGF-β1 like activity released by BSC-1 cells in culture.

5.2. CONSTRUCTION OF EXRESSION VECTORS CONTAINING THE TGF-β1 CODING SEQUENCE

In order to express a biologically active, mature form of TGF-β1, an expression vector/host system should be chosen which provides not only for high levels of transcription and translation but for the correct processing of the gene product. This is especially important when employing the entire coding sequence of the simian TGF-β1 precursor in the expression constructs because the mature form of TGF-β1 appears to be derived from the precursor product via cellular processing events. The proposed processing scheme is presented in FIG. 20. In addition an expression/host cell system which provides for secretion of the product may be selected.

In particular, it appears that the mature TGF-β1, a disulfide linked homodimer of 112 amino acids per subunit is formed by cellular processing involving proteolytic cleavage of the full length precursor at the Arg-Arg amino acid (residue numbers 277 and 278 in FIG. 1). In addition, the simian TGF-β1 precursor contains three potential N-glycosylation sites not found in the mature form and analysis of [$^3$H] glucosamine labeled serum free supernatants from a line of chinese hamster ovary cells which secrete high levels of recombinant TGF-β1 indicate that the TGF-β1 precursor, but not the mature form, is glycosylated. Thus, the proper glycosylation of the precursor may be important to the cellular synthesis and release or secretion of the mature molecule. The TGF-β1 precursor, but not the mature form, is also phosphorylated, further suggesting the functional importance of the precursor. Moreover, the mature form of TGF-β1 comprises a disulfide linked dimer involving nine cysteine residues per subunit. Some of these are involved in interchain and others in intrachain disulfide bonds which affect the tertiary structure and configuration of the mature molecule, and, as a result, its biological activity. Thus, the ability of a host cell used in the expression system to correctly express and process the simian TGF-β1 gene product is important to the production of a biologically active, mature TGF-β1.

In the examples described herein, the mature, bioactive form of TGF-β1 was successfully produced using simian virus 40 (SV40) expression control elements in a Chinese Hamster ovary (CHO) host cell system. However, a variety of other animal host/expression vector systems (i.e., vectors which contain the necessary elements for directing the replication, transcription and translation of the TGF-β1 coding sequence in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionine promoter).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionien promoter) or from viruses that grow in these cells, (e.g. vaccinia virus 7.5K promoter) may be used. Promoters produced by recombinant DNA or synthetic techniques may also be used to provide for transcription of the inserted sequences.

Specific initiation signals are also required for suficient translation of inserted protein coding sequences. These signals include the ATG initiation codon and adjacent sequences. In cases where the entire TGF-β1 gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the TGF-β1 coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

Any of the methods previously described for the insertion of DNA fragments into a vector may be used to construct expression vectors containing the TGF-β1 gene and appropriate transcriptional/translational control signals. These methods may include in vitro recombinant DNA techniques, synthetic techniques and in vivo recombinations (genetic recombination).

In cases where an adenovirus is used as an expression vector, the TGF-β1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing TGF-β1 in infected hosts. Similarly, the vaccinia 7.5K promoter may be used.

An alternative expression system which could be used to express TGF-β1 is an insect system. In one such system, *Autographa californica* nuclear polyhedrosis virus (ACNPV) is used as a vector to express foreign genes. The virus grows in *Spodoptera frugiperda* cells. The TGF-β1 coding sequence may be cloned into non-essential regions (for example the polyhedrin gene) of the virus and placed under control of an AcNPV promoter (for example the polyhedrin promoter). Successful insertion of the TGF-β1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed.

In addition, a host cell strain may be chosen which modulates the expression of the inserted sequences, or modifies and processes the gene product in the specific fashion desired. Expression from certain promoters can be elevated in the presence of certain inducers, (e.g. zinc and cadmium ions for metallothionein promoters). Therefore, expression of the genetically engineered TGF-β1 may be controlled. This is important if the protein product of the cloned foreign gene is lethal to host cells. Furthermore, modifications (e.g. glycosylation) and processing (e.g., cleavage) of protein products are important for the function of the protein. Different host cells have characteristic and specific mechanisms for the post-translational processing and modificatin of proteins. Appropriate cell lines or host systems can be chosen to ensure the correct modification and processing of the foreign protein expressed.

5.3. IDENTIFICATION OF TRANSFECTANTS OR TRANSFORMANTS EXPRESSING THE TGF-β1 GENE PRODUCT

The host cells which contain the simian TGF-β1 coding sequence and which express the biologically active, mature product may be identified by at least four general approaches: (a) DNA-DNA hybridization; (b) the presence or absence of "marker" gene functions; (c) assessing the level of transcription as measured by the expression of TGF-β1 mRNA transcripts in the host cell; and (d) detection of the mature gene product as measured by immunoassay and, ultimately, by its biological activity.

In the first approach, the presence of the simian TGF-β1 coding sequence inserted in the expression vector can be detected by DNA-DNA hybridization using probes comprising nucleotide sequences that are homologous to the simian TGF-β1 coding sequence substantially as shown in FIG. 1, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the TGF-β1 coding sequence is inserted within a marker gene sequence of the vector, recombinants containing the TGF-β1 coding sequence can be identified by the absence of the marker gene function. Alternatively, a marker gene can be placed in tandem with the TGF-β1 sequence under the control of the same or different promoter used to control the expression of the TGF-β1 coding sequence. Expression of the marker in response to induction or selection indicates expression of the TGF-β1 coding sequence.

In the third approach, transcriptional activity for the TGF-β1 coding region can be assessed by hybridization assays. For example, polyadenylated RNA can be isolated and analyzed by Northern blot using a probe homologous to the TGF-β1 coding sequence or particular portions thereof. Alternatively, total nucleic acids of the host cell may be extracted and assayed for hybridization to such probes.

In the fourth approach, the expression of the mature protein product can be assessed immunologically, for example by Western blots, immunoassays such as radioimmuno-precipitation, enzyme-linked immunoassays and the like. The ultimate test of the success of the expression system, however, involves the detection of the biologically active TGF-β1 gene product. Where the host cell secretes the gene product the cell free media obtained from the cultured transfectant host cell may be assayed for TGF-β1 activity. Where the gene product is not secreted, cell lysates may be assayed for such activity. In either case biological assays such as the growth inhibition assay described herein or the stimulation of anchorage independent growth in target cells, also described herein or the like may be used.

Once a clone that produces high levels of biologically active, mature TGF-β1 is identified, the clone may be expanded and the TGF-β1 may be purified using techniques well known in the art. Such methods include immunoaffinity purification, chromatographic methods including high performance liquid chromatography, and the like.

Despite the fact that the amino acid sequence of the simian TGF-β1 precursor differs somewhat from that of the predicted human precursor, the amino acid sequence of the biologically active mature form of the simian TGF-β1 produced in accordance with the invention is identical to that of the human mature form. In addition, the simian TGF-β1 of the invention has a biological activity that is indistinguishable from that of natural TGF-β1. This indicates that the expression/host cell systems of the invention are capable of processing the expression product so that a molecule having biological activity identical to that of authentic natural TGF-β1 is produced. As a result, the simian TGF-β1 produced in accordance with the invention may be used for all applications in which TGF-β1 may be used.

5.4. INITIAL CHARACTERIZATION OF THE TGF-β1 GENE PRODUCT

The amino portion of the precursor region of TGF-β1 from human, rodent and simian sources show a high degree of homology (Derynck et al., 1985, Nature 316:701–705; Derynck et al., 1986, J. Biol. Chem. 261:4377–4379; Sharples et al., 1987, DNA 6:239–244), suggesting an important biological function may be associated with this part of the molecule. The data presented in Section 8, infra, demonstrating that this portion of the TGF-β1 precursor is glycosylated and phosphorylated support this contention since one might assume that a cell would not go through the expense of performing these secondary modifications were it not for a specific function. These modifications may be important for dimerization of the precursor or for directing its movement out of the cell: perhaps this phospho-glycoprotein is free to perform other intra- or extracellular functions. There is evidence which suggests that glycosylation of the precursor is involved in the transport of mature TGF-β1 out of the cell.

5.5. THE TGF-β1 PRECURSOR: CELLULAR PROCESSING, STRUCTURAL NATURE AND POSSIBLE FUNCTION

The cDNA cloning of TGF-β1 described in section 6, infra, suggests that the molecule undergoes a variety of post translational processing events before secretory exit (Derynck et al., 1985, Nature 316:701–705; Derynck et al., 1986, J. Biol. Chem. 261:4377–4379; Sharples et al., 1987, DNA 6:239–244). Protein purification and amino terminal sequencing techniques were used to characterize the recombinant TGF-β1 proteins produced and released by CHO-TGF-β1-3-2000 cells (Section 8, infra).

The amino-terminal sequence analysis of isolated precursor and mature TGF-β1 polypeptides, described in section 8.3 and 8.4, infra provides information about these proteolytic processing events. Precursor polypeptides isolated from reduced polyacrylamide gels generated a major protein sequence which, according to that predicted from the simian cDNA (Sharples et al., 1987, DNA 6:239–244), begins at Leu-30 of the TGF-β1 precursor. No heterogeneity in the amino-terminal sequence was observed indicating a specificity in proteolytic processing. This result implicates the Gly-29/Leu-30 peptide bond as the signal peptidase cleavage site and is consistent with that predicted by the signal peptide prediction method of von Heijne (von Heijne, 1986, Nucleic Acids. Res. 14:4683–4690). In addition to signal peptide cleavage, purification and examination of the mature TGF-β1 (Sections 8.2 and 8.4, infra) revealed that rTGF-β1 is proteolytically processed at the predicted dibasic protease site (Sharples et al., 1987, DNA 6:239–244) resulting in a mature polypeptide. Furthermore, protein sequence analysis of the carboxy-terminal CNBr fragment of mature TGF-β1 suggests an intact molecule. Thus, CHO cells possess the appropriate proteases necessary for correctly processing pre-pro-TGF-β1.

The major biological activity secreted by transfected CHO cells is the mature dimeric growth factor. The results presented in Section 8.2., infra indicate that greater than 95% of the activity present in CHO conditioned medium co-purifies with mature rTGF-β1, whereas less that 5% co-purifies with the larger rTGF-β1 precursor. In addition, recombinant TGF-β1 behaved identically to rTGF-β1 and possessed an identical specific biological activity (Section 8.5, infra). The rTGF-β1 precursor, in contrast, was 50-fold less active than the mature growth factor. A comparison of mink lung inhibition profiles show a slightly altered dose-response curve suggesting a different receptor affinity for the precursor as compared to the mature TGF-β1.

Although the results presented in Section 8.5, infra and discussed above suggest that the rTGF-β1 precursor is biologically active, an indepth structural analysis has revealed some intriguing anomalies complicating definitive interpretations. Protein sequence analysis and SDS-PAGE reveal that the isolated precursor consists of pro-TGF-β1 mature TGF-β1, and the pro region of the precursor interlinked by disulfide bonds. Chemical cleavage of this disulfide linked mixture with CNBr and separation of CNBr peptides clearly show that the CYS-33 of the precursor forms a disulfide bond with one cysteine residue of mature TGF-β1 (FIG. 20A). The existence of the monomeric chain of TGF-β1 interconnected with precursor sequences limits any definite conclusions which can be made concerning the biological activity of the intact precursor. The formation of this disulfide-linked complex in CHO cells raised a question about its significance in tissues and cells which secrete TGF-β1 naturally. The very high level secretion of rTGF-β1 polypeptides by CHO cells may lead to an unnatural crosslinking due to improperly folded rTGF-β1 resulting in an expression artifact. Alternatively, the disulfide-linked precursor complex may represent an important intermediate in TGF-β1 processing. However, studies which show that the disulfide linkage formed by CYS-33 of the precursor is not necessary for the production of mature, bioactive TGF-β1 suggest that such complexes may not be requisite intermediates (Section 5.7 and 10, infra). Disulfide-linked precursor complexes have been observed in latent isolated forms of TGF-β1 (Miyazono et al., 1988, J. Cell Biochem. Suppl. 12A:200; Wakefield et al., 1987, J. Biol. Chem. Suppl. 11A:46).

Based on results presented in Section 8.2–8.5, infra, the processing of pre-pro-TGF-β1 in transfected CHO cells is proposed (FIG. 20B). While the proposed processing scheme is not complete, it emphasizes several of the steps which have been at least partially defined. Although the order of the various processing steps has not been characterized completely, they are described as occuring in succession to facilitate comprehension. The first step involves signal peptide cleavage at the Gly-29/Leu-30 peptide bond. This cleavage event most likely occurs co-translationally during transit of the precursor through the rough endoplasmic reticulum membrane (Blobel and Dobberstein, 1975, J. Cell. Biol. 67:835–851; Walter et al., 1984, Cell 38:5–8). Following cleavage of the signal peptide, core glycosylation units (Rothman et al., 1978, Cell 15:1447–1454) are added to pro-TGF-β1 at each of the predicted N-glycosylation sites located at Asn-82, Asn-136 and Asn-176 (Sections 8.1 and 9). The core glycosylated pro-TGF-β1 is then sequentially processed during transit through the golgi to yield a phosphorylated glycoprotein, containing complex, sialated oligosaccharides. At some stage during synthesis or transit, proteolytic cleavage at the dibasic residue and disulfide isomerization occurs, releasing mature TGF-1.

The results presented in Section 12., et seq. herein indicate that proper carbohydrate processing is necessary for secretion of the TGF-β1 polypeptide from the transfected CHO line TGF-β3-2000 clone 17. Glycosylation inhibitors which affect early stages of carbohydrate processing drastically altered the efficiency of the secretion process. Further studies with a deletion mutant of TGF-β1 which lacked the three glycosylation sites also revealed defects in secretion, and is most likely defective in intracellular routing and presumably accumulate in the endoplasmic reticulum. Conversely, inhibitors which affect later stages of processing by inhibiting the presence of mannosidases within the golgi led to increases in TGF-β1 secretion. Although the signals involved in intracellular routing are not well understood, these results suggest that carbohydrate processing is necessary for proper secretory exit of TGF-β1 and that early stages of remodeling are most crucial for its intracellular routing. The carbohydrate itself may play a direct role in secretion whereby specific receptors for the oligosaccharide side chains may help direct the protein through the secretory process. Alternatively, the carbohydrate may function in a more indirect role by determining a specific and required confirmation for TGF-β1 transport.

There are two types of pathways which lead to secretion of proteins, regulated and nonregulated (constitutive). Regulated pathways are predominantly found in secretory cell types and require an external stimuli in order to release material within the secretory vesicles. The transfected CHO cells described herein are most likely of the nonregulated type. Applicants' results showing low levels of proteolytically processed TGF-β1 within the CHO cells indicate no accumulation of mature growth factor, consistent with a nonregulated type of release. TGF-β1 may also be secreted and released by a regulated pathway. This polypeptide growth factor is a major component of platelets and is released from platelets by thrombin treatment.

The TGF-β1 propeptide is cleaved at the carboxy-terminal side of four basic residues releasing mature TGF-β1 beginning at Ala-279. Studies presented in Section 12., et seq. herein using reagents which affect intravesicular pH demonstrate that cleavage occurs within acidic vesicular compartments much the same as the processing of insulin and neuropeptide precursors. Properties of these processing proteases are generally not well understood. The existence of paired basic residues at the cleavage site may be required for efficient proteolysis. It is interesting to note that in all TGF-β family members identified recently, the amino terminal residue of the mature TGF-β polypeptide is preceded by several basic amino acid residues. Inhibitors of glycosylational processing which should alter the tertiary structure of the TGF-β1 peptide had little or no effect on proteolytic processing suggesting that this region may be adequately exposed in the precursor regardless of carbohydrate processing. The multiple basic residues preceding the amino-terminal groups of mature TGF-β family members may highlight this region for specific proteolysis.

5.6. INTERACTIONS OF TGF-β1 PRECURSOR WITH THE INSULIN-LIKE GROWTH FACTOR-II/MANNOSE 6-PHOSPHATE RECEPTOR

The results described in Section 9, infra, show the presence of mannose-6-phosphate in the TGF-β1 precursor and raise the possibility that the precursor possesses an independent function. The additional studies described in Section 11., et seq. demonstrate that the TGF-β1 precursor binds to the insulin-like growth factor-II/mannose 6-phosphate cell surface receptor. These studies also present evidence that bound TGF-β1 precursor is internalized.

Mannose-6-phosphate, a phosphorylated sugar analog, appears to play a fundamental role in the targeted transport and intercellular exchange of lysosomal enzymes (von Figura, 1986, Ann. Rev. Biochem. 55: 167–193). Specific receptors which recognize the mannose-6-phosphate residues of lysosomal enzymes have been identified and are essential components of the transport system. Secreted lysosomal proteins containing mannose-6-phosphate have been identified in the conditioned medium of tissue culture cells (Gal and Gottesman, 1986, J. Biol. Chem. 261:1760–1765; Capony et al., 1981, J. Cell. Biol. 104:253–262; Baumbach et al., 1984, Proc. Natl. Acad. Sci. USA 81:2985–2989; Sahagian and Gottesman, 1982, J. Biol. Chem. 257:11145–11150). All of these proteins, however, exhibit acid hydrolase activity.

The mannose-6-phosphate residues of the TGF-β1 precursor may direct pro-TGF-β1 to lysosomes for proteolytic processing to yield mature TGF-β1. Alternatively, the mannose-6-phosphate residues may function to target the cleaved TGF-β1 precursor to lysosomes for degradation.

It has recently been reported that the cation-independent mannose-6-phosphate receptor is identical to the insulin-like growth factor II (IGF-II) receptor (Morgan et al., 1987, Nature 329:301–307; Roth et al., 1987, Biochem. Biophys. Res. Comm. 149:600–606; MacDonald, 1988, Science 239:1134–1137). This receptor appears to be bifunctional, containing separate binding sites for IGF-II and mannose-6-phosphate. Although the biological significance of a single receptor which binds IGF-II and proteins containing mannose-6-phoshate is unclear, this bifunctional receptor may play important roles for signal transduction and/or for targeted sorting of receptor bound proteins. Proliferin, a prolactin-related glycoprotein, thought to be an autocrine growth regulator (Lee and Nathens, 1987, Endocrinology 120:208–213), has been shown to contain mannose-6-phosphate and to bind tightly to IGF-II/mannose-6- phosphate receptors (Lee and Nathens, 1988, J. Biol. Chem. 263:3521–3527). It is possible that the TGF-β1 precursor interacts specifically with this bifunctional or other mannose-6-phosphate cell surface receptor.

Applicants have determined that recombinant TGF-β1 precursor is capable of binding to the IGF-II/man6P receptor on the plasma membrane of cells based on results of in vitro studies, such as those described in Section 11., et seq. herein, demonstrating that: (1) rTGF-β1 precursor binding to rat adipocytes is enhanced by insulin-induced translocation of the IGF-II/man6P receptor to the plasma membrane; (2) rTGF-β1 precursor binding to CHO cells overexpressing the IGF-II/man6P receptor is greater than binding to parental CHO cells; and (3) rTGF-β1 precursor binding to both rat adipocytes and CHO cells is specifically inhibited by mannose 6-phosphate.

Mannose 6-phosphate half-maximally inhibited the binding of rTGF-β1 to CHO cells overexpressing the IF-II/man6P receptor (transfected CHO cells) at a concentration of 10 μM, a value close to that previously found (8 μM) to half-maximally inhibit binding to the isolated receptor (Section 9.2., supra.). In addition, mannose 1-phosphate was much less effective at inhibiting binding than was man6P, results which are consistent with the known specificities of the IGF-II/man6P receptor for these two sugars (Von Figuro and Hasilik, 1986, Ann. Rev. Biochem. 55:167–193).

Applicants believe that rTGF-β1 precursor is rapidly internalized after binding to the IGF-II/man6P receptor on transfected CHO cells based on the results described in Section 11.2.1., infra. After binding at 37° C. to the IGF-II/man6P receptor on transfected CHO cells, rTGF-β1 precursor rapidly became resistant to removal by an acid wash of these cells. For example, after only 10 minutes at 37° C., greater than 75% of specifically bound radioligand was resistant to the acid wash, suggesting that the great majority of bound rTGF-β1 precursor had become internalized during this time period (Haigler, 1980, J. Biol. Chem. 255:1239–1241). After longer incubations at 37° C., further increases in the cellular uptake of radiolabeled material were observed and, since the additional increase was not blocked by mannose 6-phosphate, is likely due to the uptake of breakdown products of degraded TGF-β1 precursor.

Additional studies were conducted to determine whether latent TGF-β complex isolated from platelets could also bind to the IGF-II/man6P receptor. The results of these experiments, presented in Section 11.2.2., infra, indicate that platelet-derived TGF-β1 complex strongly competed with rTGF-β1 precursor for binding to the receptor, suggesting that the latent TGF-β complex also contains mannose 6-phosphate. Attempts to detect binding of the IGF-II/man6P receptor to the platelet-derived TGF-β1 precursor remnant following electrophoresis and transfer to nitrocellulose filters were unsuccessful and may be due to the presence of fewer man6P residues on the platelet TGF-β1 precursor than on the rTGF-β1 precursor. Such an explanation is consistent with the observed differences between platelet and recombinant TGF-β1 precursors in their abilities to compete with rTGF-β1 precursor for binding to isolated man6P receptors: platelet-derived precursor is about one-third as potent as rTGF-β1 in this regard. Alternatively, it is possible that some phosphate is removed by phosphatases during the lengthy purification procedure used to obtain the platelet-derived TGF-β1 precursor.

Recent studies of the platelet TGF-β1 precursor indicate that its carbohydrate structure may be important in maintaining this complex in the inactive state (Miyazono and Heldin, 1989, Nature, in press); digestion by endoglycosidase or sialidase was found to activate the latent platelet TGF-β1 complex. Moreover, incubation of the complex with man6P and sialic acid, but not other sugars, was also found to activate the latent TGF-β1, supporting a role for the carbohydrate in maintaining the platelet TGF-β1 precursor in its latent state. The results described in Section 11.2., et seq. herein suggest that man6P on the TGF-β1 precursor can direct this molecule to cells via its interaction with the IGF-II/man6P receptor. This interaction may lead to either the activation or degradation of TGF-β1 precursor via its internalization and delivery to an endoctic compartment.

5.7. BIOLOGICAL ACTIVITY OF TGF-β1

The mature TGF-β1 product of the invention is a potent inhibitor of tumor cell growth in vitro and in vivo. Experiments measuring the anti-proliferative effect of TGF-β1 on mink lung epithelial cells demonstrated that the recombinant TGF-β1 of the invention (rTGF-β1) and natural TGF-β1 (nTGF-β1) have identical specific activities (Section 8.5, infra). In addition, the dose response curves of rTGF-β1 and nTGF-β1 are virtually indistinguishable.

The results in Section 8.6., infra demonstrate that both natural TGF-β1 and the rTGF-β1 of the invention inhibit tumor growth in vivo. The tumorstasis observed in TGF-β treated human lung tumors is also accompanied by induction of a more differntiated-like phenotype. Mucous secreting cells, a minor population in the mock-treated, poorly differentiated tumors, dominated TGF-β treated tumors. Consistent with the secretory role of the goblet cell in normal tissues (Robbins and Angell, 1971, Basic Pathology, W. B. Sander G., Philidelphia, Pa.) and thus a more differentiated state, is the enhanced expression of mucinlike and hyaluronic acid products found in TGF-β treated tumors. Innumerable other histological indices also suggest the TGF-β mediated induction of the differentiated phenotype, including the pronounced display of columnar epithelial cell organization surrounding the vessel wall and increased deposition of extracellular matrix, i.e., collagen.

The powerful inhibitory effect of rTGF-β1 on the growth and differentiation of human lung adenocarcinomas in athymic nude mice provide additional evidence that the rTGF-β1 of the invention may find use in the development of novel, perhaps less cytotoxic, cancer therapy regimens.

5.8. IMPROVED METHOD FOR PRODUCING MATURE TGF-β1

In a specific embodiment of the invention, the TGF-β1 precursor was modified by eliminating the amino acid cysteine at position 33 (CYS-33) of FIG. 1 and replacing it with serine. The modification was introduced at the DNA level using site directed mutagenesis. COS cells transfected with plasmids encoding the modified precursor gene ultimately secrete between three and five times more mature TGF-β1 than do CHO cells expressing the unmodified precursor gene. It is believed that this modification prevents the formation of certain disulfide-linked precursor complexes in the transfected COS cells and therefore allows for the secretion of more mature TGF-β1. Preliminary analysis indicates that the mature TGF-β1 produced by this method is correctly processed and biologically identical to natural TGF-β1.

Modifications of the TGF-β1 precursor at two other cysteines, CYS-223 and CYS-225, resulted in the secretion of mature TGF-β1 but did not result in the secretion of higher levels. Details of the construction and expression of the modified TGF-β1 genes are given in Section 10, infra.

Although the three cysteines located in the pro region of the TGF-β1 precursor may not be essential for the production of mature rTGF-β1, they may be important in the regulation of TGF-β1. In this regard, dimerization of the precursor seems unnecessary for proteolytic cleavage of mature TGF-β1, but it may be required for latency.

Cells transfected with a plasmid coding for pre-pro-TGF-β1$^{S223/225}$ released TGF-β1 in an active form (Section 10.2.4., infra). Recently latent TGF-β1 has been purified from human platelets as high molecular weight complex in which the dimeric pro portion of the TGF-β1 precursor is disulfide-linked to an unknown protein and non-covalently associated with mature TGF-β1 (Miyazono et al., 1988, J. Biol. Chem. 263:6407–6415; Wakefield et al., 1988, J. Biol. Chem. 263:7646–7654). In the CHO cell expression system, there is no evidence that another protein is involved in the formation of complexes with the precursor and mature forms of TGF-β1. This is also likely to be true in the COS cell system, since the rTGF-β1 precursor and mature forms produced by COS cells appear similar if not identical to those produced by CHO cells when examined by immunoblotting.

Applicants' results indicate that mature rTGF-β1 is non-covalently associated with the precursor pro region and when the pro region can not form a dimer, latency is not conferred. While this is most likely due to the disruption of the non-covalent association, applicants can not rule out the possibility that mature TGF-β1 is non-covalently associated with the monomeric TGF-β1$^{S223/225}$ pro region, (forming a complex that is not latent because the mature sequences necessary for activity are sufficiently exposed).

Recent studies (Miyazono et al., 1988, J. Biol. Chem. 263:6407–6415) indicate that carbohydrate structures in the pro region are involved in non-covalently binding TGF-β1 to form a latent complex. Perhaps, dimerization of the pro region provides the proper framework and stability for such interactions. Litle is known about the in vivo regulation of TGF-β1. Since most cell types release TGF-β1 in a latent form (Lawrence et al., 1984, J. Cell. Physiol. 121:184–188; Pircher et al., 1986, Biochem. Biophys. Res. Commun. 136:30–37; Wakefield et al., 1987, J. Cell. Biol. 105:965–975), activation of the latent complex appears to be a critical regulatory step. A clearer understanding of the nature of this latency should aid in determining physiological mechanisms of activation.

The high level of expression and secretion of recombinant TGF-β1 may lead to an unnatural cross-linking, making the disulfide linkage between CYS-33 and cysteine residues located in the mature polypeptide an artifact of the expression system. Alternatively, CYS-33 may play a regulatory role through interactions with other proteins. This seems especially plausible in view of the disulfide-linked complex isolated from platelets.

Thus, the three cysteines located in the pro portion of the precursor may influence the maturation and activation of TGF-β1 in two ways. CYS-223 and CYS-225 may allow the precursor to form a dimer and may subsequently interact with mature TGF-β1 in a non-covalent manner to form a latent complex, while CYS-33 may act by disulfide bonding to mature TGF-β1 and/or other proteins, thereby modulating the action of TGF-β1.

6. EXAMPLE: CDNA CLONING OF TGF-β1 PRECURSOR

The examples that follow describe the cDNA cloning of the TGF-β1 precursor coding sequence from an African Green monkey cell line (BSC-40, a subline of BSC-1 cells) previously shown to produce high levels of a growth inhibitor functionally related to TGF-β1. Exceedingly strong sequence homology between the simian precursor and the gene product predicted for both human and mouse TGF-β1 were found.

6.1. MATERIALS AND METHODS

The following procedures were used to clone the cDNA encoding the TGF-β1 precursor.

6.1.1. GROWTH OF CELLS AND RNA EXTRACTION

BSC-40 cells were grown in Dulbecco's modified Eagle medium containing 10% fetal calf serum. MCF-7 cells were grown in the same medium containing 6 units/ml insulin. Polyadenylated RNA was isolated from these cells by oligo [dT]-cellulose chromatography as described (Purchio et al., 1979, J. Virol. 29:763–769).

6.1.2. cDNA LIBRARY CONSTRUCTION AND SCREENING

Double stranded cDNA was synthesized from BSC-40 polyadenylated RNA as described (Maniatis et al., 1982, Molecular Cloning: A Laboratory Manual, Cold Spring Harbor Laboratory, Cold Spring Harbor, N.Y., 371–372) and after treatment with EcoRI methylase was ligated to oligonucleotide linkers containing an EcoRI restriction enzyme recognition site (EcoRI linkers). The cDNA was digested with EcoRI and fractionated by chromatography on Sephacryl S-1000. cDNA fractions greater than 750 base pairs (bp) were pooled and ligated into lambda gt10 which had been cut with EcoRI (Davis et al., 1980, A Manual for Genetic Engineering: Advanced Bacterial Genetics; Cold Spring Harbor Laboratory, Cold Spring Harbor, N.Y.), packaged (Grosveld et al., 1981, Gene 13:227–237) and plated on $E.$ $coli$ $C_{600}rK^-mK^+hfl$. The library was screened by plaque hybridization (Bentonet al., 1977, Science 196:180–182) to a [$^{32}$P]-labeled oligonucleotide probe [5'-CACGCAGCA-GTTCTTCTCCGTGGAGCTGAAGCAATA-3'] complementary to codons 6 through 17 of the mature TGF-β1 molecule (Derynck et al., 1985, Nature 316:701–705). Several cDNA clones were isolated after tertiary screening and subcloned into pBR322. One clone (pTGF-β1-2) containing a 1600 bp insert was subcloned into the M13mp18 and M13mp19 cloning vectors (Yanisch-Perron et al., 1985, Gene 33:103–119) and both strands were sequenced using the dideoxy chain-termination method (Sanger et al., 1977, Proc. Natl. Acad. Sci. USA 74:5463–5467).

6.1.3. NORTHERN BLOT ANALYSIS

Polyadenylated RNA was isolated from MCF-7 cells and BSC-40 cells as described (Purchio et al., 1979, J. Virol. 29:763–769), fractionated on a 1% agarose-formaldehyde gel (Lehrach et al., 1977, Biochemistry 16:4743–4751), transferred to a nylon membrane (Hybond, Amersham) and hybridized to [$^{32}$P]-labeled pTGF-β1-2 probe. Hybridization was carried out at 42° C. in 50% formamide containing 0.9M NaCl, 50 mM sodium phosphate, 5 mM EDTA, 0.1% SDS, 4XDenharts solution (Maniatis et al., 1982, Molecular Cloning: A Laboratory Manual, Cold Spring Harbor Laboratory, Cold Spring Harbor, N.Y., 371–372), 0.4 mg/ml yeast tRNA and 0.25 mg/ml denatured calf thymus DNA. Filters were washed at 65° C. in 0.25×SSC (Maniatis et al., 1982), 0.1% SDS, dried and exposed to Cronex-4 X-ray film (DuPont) with the aid of lightening plus intensifier screens (DuPont).

6.2. RESULTS

The CDNA library constructed in lambda gt10 using polyadenylated RNA from BSC-40 cells as described above was screened with a 36-mer deoxyoligonucleotide complementary to codons 6 through 17 of the mature TGF-β1 molecule (Derynck et al., 1985, Nature 316:701–705). Due to the close similarity between bovine TGF-β1 (Roberts et al., 1983, Biochemistry 22:5692–5698) and human TGF-β1 (Derynck et al., 1985, Nature 316:701–705) we selected a probe derived from human sequences to screen the simian TGF-β1 cDNA clones.

A total of 13 positive clones were identified after three rounds of plaque purification. A 1600 bp clone, pTGF-β1-2, which appeared by restriction enzyme analysis to contain the entire TGF-β1 precursor coding region, was chosen for sequencing. The DNA sequence, along with the deduced amino acid sequence, is shown in FIG. 1. A single open reading frame was found coding for a 390 amino acid polypeptide. The mature TGF-β1 polypeptide consists of the carboxy terminal 112 residues. This arrangement is the same as that described for human TGF-β1 (Derynck et al., 1985, Nature 316:701–705) and mouse TGF-β1 (Derynck et al., 1986, J. Biol. Chem. 261:4377–4379). The simian cDNA clone is 98% homologous to the human cDNA clone throughout the coding region with only 27 mismatches (FIG. 1) and one gap of three bases.

Within the 5'-noncoding region, the DNA sequences of the human and simian TGF-β1 are 91% homologous with 3 gaps while the 3'-noncoding regions are 94% homologous with no gaps. Just upstream of the 5' initiating codon is a potential stem structure which is also present in the human cDNA clone but not in the mouse clone. An apparent insertion within this region in the mouse clone would inhibit formation of this structure. Like the human and mouse clones, the simian CDNA clone was not full length as no 3'-polyadenylated track was identified. The G-C rich nature of the 3'-end of the TGF-β1 precursor mRNA may have resulted in a secondary structure which prevented DNA synthesis through this region. The 3'-noncoding region exhibits a remarkable repetition of the purine sequence, CCCC, following the termination codon. This sequence occurs nine times in the human sequence with an additional repeat containing one base difference. Both the simian and murine clones contain 8 repetitions with an additional 2 containing a single base difference.

Northern blot analysis using the TGF-β1-2 probe showed hybridization to a major 2.5 Kb polyadenylated RNA species from BSC-40 cells and from the human mammary carcinoma cell line MCF-7 (FIG. 2). This is the same size as the major transcript found in human cell lines (Derynck et al., 1985, Nature 316:701–705) and mouse cell lines (Derynck et al., 1986, J. Biol. Chem. 261:4377–4379). Minor bands at 4 kb and 1.45 kb can also be seen in lane 2 of FIG. 2.

The amino acid homology between the human and simian TGF-β1 precursor proteins is also shown in FIG. 1. Only five amino acid changes occur, all of which are found within the amino terminal precursor region: there is complete homology between the simian and human mature TGF-β1 proteins at the amino acid level. By contrast, only 84% homology (at the amino acid level) was found to exist between the simian and mouse precursor TGF-β1 molecules; the differences include the following: one amino acid change, a serine (mouse) to an alanine (simian) was found in the mature TGF-β1 coding region. The human gene codes for an extra amino acid (arginine, position 158) in the precursor which is neither present in the simian nor murine clone. Presumably this change is due to an insertion within the human gene which was sequenced (Derynck et al., 1985, Nature 316:701–705). The close identity between the precursor region of the monkey, mouse and human TGF-β1 protein suggests that this part of the molecule may also have an important biological function.

The carboxy terminus of the precursor contains the 112 amino acid mature form of simian TGF-β1 and is identified by its homology to the corresponding human gene product. This cysteine rich (9 residues) region of the precursor represents the secreted form of TGF-β1 and does not contain any putative glycosylation sites, whereas three potential N-glycosylation sites (Asn at positions 82, 136 and 177) can be identified in other regions of the precursor. It is known that the TGF-β1 homodimer, both of human and rodent origin, requires intact disulfide bonds to maintain activity (Messague, 1984 J. Biol. Chem. 259:9756–9761). The amino-terminus of mature human TGF-β1 as established by primary sequence analysis (Derynck et al., 1985, Nature 316:701–705) is preceded by an Arg-Arg dipeptide. This similar cleavage site is also present in an identical position in the simian homolog. Cleavage either during or after the translational process, concomitant with either or both intrachain and interchain disulfide bond formation, would result in the genesis of the active homodimer (dimerization). In this regard, the TGF-β1 precursor contains a leucine rich region of 14 hydrophobic amino acids (positions 8–21, FIG. 1) which could function as a signal peptide and play a role in the secretion/processing cascade.

7. EXAMPLE: EXPRESSION OF TGF-β1

The examples that follow describe the expression of active TGF-β1 in Chinese Hamster Ovary (CHO) cells transfected with a recombinant plasmid containing the coding sequence for TGF-β1 under the control of simian virus 40 (SV40) expression elements. The experiments described herein demonstrate that a number of CHO transfectants produced and secreted high levels of TGF-β1. The TGF-β1 released by the transfected cells demonstrated biological activity comparable to that of authentic natural TGF-β1 as determined by growth inhibition assays using target cells that are sensitive to TGF-β1.

7.1. MATERIALS AND METHODS
7.1.1. CELL CULTURE

Dihydrofolate reductase (dhfr)-deficient Chinese hamster ovary (CHO) cells (Urlaub and Chasin, 1980 Proc. Natl. Acad. Sci. U.S.A. 77:4216) were propagated in Ham's F-12 medium (Gibco Laboratories, NY) supplemented with 10% fetal bovine serum (FBS) and 150 ug/ml of L-proline. Penicillin and streptomycin were included at 100 U/ml and 100 ug/ml, respectively. CHO transfectants were grown in Dulbecco's modified Eagle's medium containing the same supplements as those listed above. CHO cells and their derivatives were routinely passaged by trypsinization at a 1:5 splitting ratio.

Methotrexate (Sigma, MO) was prepared at a stock concentration of 10 mg/ml in water. Dilute NaOH (0.2M) was added in order to solubilize the drug (final pH of 6). The stock was filter-sterilized and stored at −20° C. Stock solutions of methotrexate in media (100 uM) were kept at 4° C for no longer than 1 month.

7.1.2. DNA MANIPULATIONS AND PLASMID CONSTRUCTIONS

Restriction enzymes, T4 DNA ligase, calf intestinal phosphatase, the Klenow fragment of DNA polymerase I and other DNA reagents were purchased from Bethesda Research Laboratories, Md. Standard DNA manipulations were performed as outlined in Maniatis, T., et al., 1982, Molecular Cloning: A Laboratory Manual, Cold Spring Harbor Laboratory, New York.

Plasmid pSV2 (β1-TGF-dhfr), which contains the simian TGF-β1 CDNA and the mouse dhfr gene in tandem as well as intervening SV40 sequences, was constructed as outlined in FIG. 3. The pSV2-β1-TGF plasmid was prepared initially. The 1378 bp PstI-EcoRI fragment of the TGF-β1 cDNA containing the entire coding region for TGF-β1 protein was inserted into the polylinker region of pSP65 in order to place a HindIII restriction site 5' to the PstI recognition sequence. The resulting plasmid was then digested with EcoRI, repaired to blunt ends with the Klenow fragment of DNA polymerase I, and the HindIII-EcoRI (blunt) fragment containing the TGF-β1 coding sequence was isolated. Plasmid pSV2-p1-TGF was then constructed by inserting the HindIII-EcoRI (blunt) fragment into pSV2-neo in place of the neomycin resistance gene (neo), by ligation into the HindIII-HpaI fragment of the vector.

Construction of pSV2-(β1-TGF-dhfr), at this point, required two steps. The first step required the isolation of the NdeI-EcoRI (blunt) fragment of pSV2-β1-TGF. This was accomplished by digesting the pSV2-β1-TGF plasmid with EcoRI, blunting the ends with the Klenow fragment of DNA polymerase I, cutting the blunted vector with NdeI and PvuI, and isolating the 2.6 kb NdeI- EcoRI (blunt) fragment. PvuI digestion was necessary so that a contaminating plasmid fragment would not copurify upon agarose gel electrophoresis. The final step in the construction was the insertion of the NdeI-EcoRI (blunt) fragment containing the β1-TGF cDNA and SV40 sequences into one NdeI-PvuII fragment of pSV2-dhfr. The resulting pSV2-(β1-TGF-dhfr) plasmid contains a unique NdeI site which can be utilized to linearize the DNA.

7.1.3. DNA TRANSFECTIONS

Approximately 24 hours after seeding $10^6$ dhfr-deficient CHO cells onto 100 mm dishes, the cultures were transfected with 20 ug of NdeI linearized pSV2-(β1-TGF-dhfr) plasmid as a calcium phosphate precipitate (Wigler, M., et al., 1979, Proc. Natl. Acad. Sci. U.S.A. 76:1373–1376). Briefly, 20 ug of linearized DNA was added to 1 ml of 250 mM sterile $CaCl_2$. A 1 ml portion of 2× HEPES solution (280 mM NaCl, 50 mM HEPES, 1.5 mM sodium phosphate, pH 7.1) was then added dropwise, and the mixture was allowed to sit on ice for 30 minutes. The precipitate was then dispersed dropwise over the cells containing 10 ml of the F12 media. After incubation at 37° C. for 4 hours, the media was removed and replaced with 10 ml of F12 media containing 25% glycerol for 90 seconds at room temperature. Cells were rinsed once with 20 ml of F12 media and incubated in the nonselective F12 media (20 ml) for an additional 48 hours. Selection for dhfr expressing transfectants was accomplished by replacing the media with DMEM supplemented with 10% dialyzed FBS (Gibco, N.Y.) and 150 ug/ml L-proline. Colonies were observed after culturing the cells 10–14 days in the selection media. Ten colonies were aspirated by a pasteur pipet and expanded.

7.1.4. SELECTION OF METHOTREXATE RESISTANT CELLS

Dihydrofolate reductase (dhfr) amplified cells were derived from the primary transfectants essentially as described (Gasser, C. S. and Schimke, R. T., 1986, J. Biol. Chem. 261:6938–6946). After expansion, $10^5$ cells were seeded onto 100 mm dishes and adapted to increasing concentrations of methotrexate. The initial concentrations of methotrexate were 50, 100, and 200 nM. The plate containing visible colonies at the highest methotrexate concentration was trypsinized and adapted to that concentration of methotrexate for at least two additional 1:5 cell passages. Cells ($10^5$) were then seeded onto 100 mm dishes in 2,5, and 10-times the concentration of methotrexate. The dish containing visible colonies was again trypsinized and adapted in the methotrexate containing medium. Cells were frozen back at various stages of amplification in media containing 40% FBS, 10% dimethyl sulfoxide and 50% DMEM. Methotrexate was not included in the freezing media.

7.1.5. QUANTITATION OF BETA-TGF MESSAGE LEVELS

TGF-β1 mRNA levels were assessed using solution hybridization (Uhler, M. D., et al., 1986, Proc. Natl. Acad. Sci. U.S.A. 83:1300–1304). The 600 bp SmaI-SmaI fragment of the β1-TGF cDNA was cloned into pSP65 and used to make [$^{32}$P]-labeled complementary RNA by SP6 RNA polymerase as detailed by the manufacturer (Promega Biotech, Madison Wis.). Single stranded M13 DNA containing the entire β1-TGF cDNA, in the same sense as MRNA, was utilized as standards. Total nucleic acid was isolated from transfected cells by proteinase K digestion and phenol/chloroform extraction (McKnight, G. S., et al., 1980, J. Biol. Chem. 255:144–147). DNA content of total nucleic acid samples was measured by the dye binding assay (Labarca, C., and Paigen, K., 1980, Anal. Biochem. 102:344–352). The number of molecules of mRNA per cell was estimated by comparison with the M13 β1-TGF standards assuming 7 picograms of DNA per cell.

7.1.6. GROWTH INHIBITION ASSAY

Mink lung epithelial cells, Mv 1 Lu (Accession Number CCL-64, American Type Culture Collection), which are extremely sensitive to TGF-β1 were utilized for the growth inhibition assay. The assay was performed using the thymidine analog 5'-[$^{125}$I]-iodo-2' deoxyuridine ($^{125}$IdU) to assess DNA synthesis. One unit of activity was defined as the amount required to inhibit 50% incorporation of $^{125}$IdU compared to untreated CCL-64 cells. Using isolated TGF-β1 as a standard, one unit of activity generally corresponded to 80–100 pg/ml of TGF-β1.

To assay transfected cells for secretion of active TGF-β1, serum free supernatants were collected from one 24 hour collection on confluent cultures of cells and dialyzed extensively against 0.2M acetic acid. The acetic acid was removed by lyophilization and the sample was re-dissolved in sterile complete culture medium for assays.

7.1.7. STIMULATION OF ANCHORAGE INDEPENDENT GROWTH

Supernatants were tested for their ability to stimulate normal rat kidney fibroblasts (NRK; clone 49) to grow as colonies in soft agar. The soft agar assay was performed as described (Twardzik and Sherwin, 1985, J. Cell. Biochem. 28:289–297; Delarco and Todaro, 1978 Proc. Natl. Acad. Sci. U.S.A. 75:4001–4005) using acid-dialyzed supernatants.

7.1.8. PEPTIDE SYNTHESIS AND PRODUCTION OF ANTIBODIES

Peptides were synthesized by solid phase techniques on a Beckman 990 instrument, and cleaved from the resin as previously described (Gentry, L. E., et al., 1983, J. Biol. Chem. 258:11219–11228; Gentry, L. E. and Lawton, A., 1986, Virology 152:421–431). Purification was accomplished by preparative high performance liquid chromatography. The composition of the peptides was confirmed by amino acid analysis.

Synthetic peptides were conjugated to bovine gamma-globulin through the cysteine residue. Coupling reactions were essentially as described (Gentry and Lawton, 1986, supra). The efficiencies of peptide conjugations ranged from 8 to 26 molecules of peptide covalently attached per molecule of gamma-globulin.

New Zealand white rabbits were primed at three to six sites by combined subcutaneous and intradermal inoculations with the peptide conjugates (100 ug equivalents of peptide) emulsified in Freunds complete adjuvant. Booster inoculations were administered at 2–3 week intervals. Bleedings were taken 7–14 days following the boosts.

7.1.9. IMMUNOBLOTTING

Proteins were fractionated on 7.5%–17.5% gradient SDS-polyacrylamide gels and transferred to unmodified nitrocellulose (0.45 um; Schleicher and Schuell) for 14–18 hours at 200 mA at 4° C. (Burnette, W. N., 1981, Anal. Biochem. 112:195–203). Excess binding capacity of the nitrocellulose was blocked by incubation with 2.5% BLOTTO (Johnson, D. A., et al., 1984, Gene Anal. Techn. 1:3–8) in phosphate-buffered saline (PBS) containing 0.2% NP-40. Rabbit antiserum diluted 1:75 in 2.5% BLOTTO was incubated with the blocked nitrocellulose sheets for 2 hours at room temperature. After washing away excess antibody by five 5-minute washes in 2.5% BLOTTO, the nitrocellulose sheets were incubated with alkaline phosphatase-conjugated Protein A diluted 1:500 in 2.5% BLOTTO. Following a one hour incubation, the nitrocellulose sheets were washed 5 times in PBS (5 minute washes) containing 0.2% NP-40 and developed (Leary et al., 1983, Proc. Natl. Acad. Sci. U.S.A. 80:4045–4049).

7.1.10. NORTHERN BLOT ANALYSIS

Cytoplasmic polyadenylated RNA was prepared from tissue culture cells as described (Purchio and Fareed, 1979, J. Virol. 29:763) and fractionated on a 1% agarose-formaldehyde gel (Lehrach et al., 1977, Biochemistry 16:4743). The RNA was transferred to a Hybond nylon membrane (Amersham) and hybridized to radiolabeled pTGF-β1-2 probe. Hybridization was performed in 0.9M NaCl, 50 mM sodium phosphate (pH 7.0), 5 mM EDTA, 0.1% SDS, 4× Denhardts, 0.4 mg/ml yeast tRNA, 0.25 mg/ml calf thymus DNA and 50% formamide, for 20 hours at 42° C. Filters were washed four times in 0.25×SSC at 65° C. (30 minutes/wash), dried and exposed for autoradiography.

7.1.11. SOUTHERN BLOT ANALYSIS

High molecular weight DNA was isolated from the pelleted nuclei obtained after RNA extraction (Purchio and Fareed, supra). The nuclear pellet was dispersed in TE buffer and then adjusted to 1% sodium dodecyl sulfate/10 mM Tris-HCl, pH 7.4/10 mM EDTA. Proteinase K was added to 100 ug/ml and incubated at 37° C. for 16–18 hours. After the DNA was phenol/chloroform extracted and ethanol precipitated, residual RNA was removed by digestion with DNAse "free" RNAse A for 2 hours in TE buffer, followed by extensive dialysis versus TE.

For the Southern blot analysis, DNA was digested with the appropriate restriction enzyme and blotted to Hybond nylon membranes (Southern, E. M., 1975, J. Mol. Biol. 98:503–517). Hybond nylon membrane filters were hybridized at 65° C. for 20 hours in hybridization buffer containing $5 \times 10^6$ cpm/ml of denatured nick-translated EcoRI-EcoRI fragment of β1-TGF cDNA obtained from pTGF-β1-2 and washed as detailed by the manufacture (Amersham).

7.2. EXPRESSION OF TGF-β1 IN CHO CELLS

In order to express high levels of recombinant bioactive TGF-β1, we utilized the pSV2 vectors originally described (Mulligan, R. C. and Berg, P., 1981, Mol. Cell. Biol. 1:449–459; Subramani, S., et al., 1981, Mol. Cell. Biol. 1:854–864) to prepare an expression plasmid (pSV2-β1-TGF-dhfr) that places the simian TGF-β1 and mouse dihydrofolate reductase cDNAs in tandem within the same plasmid (FIG. 3). The expression plasmid carries a large portion of the TGF-β1 CDNA which encodes the complete TGF-β1 precursor molecule. The physical linkage of these two genes within the same plasmid allows for coamplification of TGF-β1 sequences during dhfr amplification. The signals required for transcription initiation, termination, polyadenylation, and splicing for each cDNA are identical and are supplied by simian virus 40 (SV40) DNA sequences.

pSV2-β1-TGF-dhfr was transfected into dhfr-deficient CHO cells as a calcium phosphate precipitate. Ten CHO transfectants expressing the dhfr phenotype were isolated by propagation in selective medium. All ten transfectants displayed TGF-β1 mRNA as assayed by solution hybridization. To increase the level of expression of TGF-β1, cells derived from the ten initial transfectants were selected stepwise in increasing concentrations of methotrexate (MTX). At various stages of amplification, cells were assayed for the level of TGF-β1 mRNA by solution hybridization. Four of the ten initial transfectants showed increased levels of TGF-β1 mRNA. Here, we describe one of these clones (TGF-β1-3), which through MTX amplification, displayed very high levels of TGF-β1 MRNA.

Table I shows the number of TGF-β1 mRNA copies per TGF-β1-3 cell at various stages of amplification. The CHO cells at various stages of amplification will be referred to as TGFβ1-3-0, TGFβ1-3-200, TGFβ1-3-2000 and correspond to CHO cells selected in 0,2 μM and 20 μM MTX, respectively.

TABLE I

EXPRESSION OF TGF-β1 mRNA IN CHO TRANSFECTANTS

| Cultured Cells | Number of TGF-β1 mRNA Copies Per Cell[1] MTX Concentration (μM) | | |
|---|---|---|---|
| | (0) | (2) | (20) |
| TGF-β1–3 | 350 | 34,000 | 76,000 |
| CHO #7 | 700 | — | — |
| Non transfected CHO | 20 | | |

[1]Number of mRNA copies per cell was determined by solution hybridization. Calculations were based on the approximation that the DNA content of one cell is 7 picograms.

As controls, we included non-transfected CHO cells and a CHO transfectant (CHO #7) initially shown to express recombinant TGF-β1 at low levels. CHO #7 was obtained by cotransfection with pSV2-β1-TGF (FIG. 3) and pSV2-neo, followed by selection in Gentecidin (Gibco, N.Y.). The initial TGF-β1-3 transfectant displayed mRNA levels of β1-TGF similar to those of CHO #7 and approximately 20 times greater than non-transfected CHO cells. However, after MTX selection, the number of β1-TGF mRNA copies observed in TGF-β1-3 cells dramatically increased approaching nearly 80,000 copies per cell at 20 μM MTX. This represented a greater than 200-fold amplification with respect to the initial TGF-β1-3 transfectant and an almost 4000-fold amplification with respect to the non-transfected CHO cells.

A northern blot of poly (A)+ selected mRNA from TGF-β1-3 cells at various stages of amplification is shown in FIG. 4A. Non-transfected CHO cell mRNA was also included to reveal the low levels of endogenous 2.5 Kb TGF-β1 mRNA present in these cells (asterisk, FIG. 4A). This low level expression of TGF-β1 mRNA has also been observed in several other cell lines. The TGF-β1-3 transfectants revealed large amounts of hybridizable RNA migrating at the predicted size of 2 Kb.

The most likely mechanism for the dramatic increase of TGF-β1 mRNA in the TGF-β1-3 cells after MTX selection is a result of amplification. In order to examine for gene amplification, DNA was isolated from the TGF-β1-3 cells at various stages of MTX selection, digested with restriction enzymes, transferred to Hybond nylon membranes, and hybridized to [$^{32}$P]-labeled TGF-β1 DNA. Both restriction enzymes EcoRI and BamHI cut within the introduced plasmid twice generating linear copies of plasmid DNA lacking flanking sequences. Since one of the BamHI sites resided within the simian TGF-β1 cDNA, digestion with this enzyme should release two fragments which hybridize to the nick-translated probe.

The results of the Southern blot are shown in FIG. 4B. In the MTX selected cells, strong hybridization to the TGF-β1 probe was observed. The size of these fragments corresponded precisely to the predicted size of the TGF-β1 containing fragments of pSV2-TGF-β1-dhfr (a 4.7 Kb fragment derived by EcoRI digestion and 4.4 and 0.51 Kb fragments derived by BamHI digestion). Similar digestion products were also observed at lower levels in the initial non-selected transfectant (TGF-β1 −3/0). Densitometric scans comparing the different TGF-β1-3 cells revealed at least a 15-and 35-fold amplification of TGF-β1 sequences in TGF-β1-3/200 and TGF-β1-3/2000 cells, respectively.

7.3. DETECTION OF SECRETED BIOACTIVE RECOMBINANT TGF-β1

To determine whether the TGF-β1 protein was made and secreted in the transfected TGF-β1-3 cells, conditioned medium was collected from these cells and tested for bioactive material. A sensitive and specific bioassay based on the ability of β1-TGF to inhibit growth of mink lung epithelial cells (CCL-64) was the initial assay used. A typical standard dose response curve using highly purified authentic human TGF-β1 is shown in FIG. 5A. In this assay, 50% inhibition of growth of mink lung cells is typically observed at 8–12 picograms (80–120 pg/ml) of TGF-β1 . Conditioned medium collected from TGF-β1-3 cells at all stages of amplification exhibited the ability to inhibit the growth of CCL-64 cells. The dose response curves of these supernatants are shown in FIG. 5B. These show similar slopes to the inhibition curves observed for authentic natural β1-TGF.

Table II shows the levels of bioactive material present in culture supernatants of TGF-β1-3 cells calculated from the curves shown in FIG. 5B.

TABLE II

CONCENTRATION OF BIOLOGICALLY ACTIVE
TGF-β1 HARVESTED FROM THE CHO-TRANSFECTANTS[1]

| Cultured Cells | Concentration of TGF-β1 in Conditioned Media of CHO Transfectants based upon Bioactivity MTX Concentration ($\mu$M) | | |
|---|---|---|---|
|  | (0) | (2) | (20) |
| TGF-β1–3 | 5.8 ng/ml | 1000 ng/ml | 5600 ng/ml[2] |
| CHO #7 | 25 ng/ml | — | — |
| Non-Transfected CHO | 1 ng/ml | — | — |

[1]Concentration of bioactive material in cell-free spernatants is expressed in ng/ml as determined from the data presented in FIG. 2B. Calculations were based on 10 picograms of native β-TGF to elicit a 50% inhibition of CCL-64 cells.
[2]Absolute amounts of TGF-β produced by the TGF-β1–3/200 cell line varied from between 1.5 mg/l to 6.5 mg/l. This may be due to several factors including tissue culture conditions of both the indicator cells (CCL-64) as well as the TGF-β1–3/200 cells.

Low levels of secreted bioactive TGF-β1 were observed in supernatants of nonamplified TGF-β1-3 cells. These levels were similar to the levels observed in the CHO #7 transfectants. MTX selected TGF-β1-3 cells expressed much higher levels of recombinant bioactive TGF-β1. At 20 $\mu$M MTX selection, TGF-β1-3 cells (TGF-β1-3/2000) secreted almost 6 ug/ml of active TGF-β1 into the serum free culture supernatants.

Table III shows the levels of bioactive material secreted in culture supernatants of the TGF-β1-3 transfectant at various stages of MTX selection. Bioactivity was assessed using the mink lung cell inhibition assay and the resulting values were normalized per cell per 24 hours. By contrast to the TGF-β1-3 transfectant, low levels of secreted bioactive TGF-β1 were observed in the supernatants of the non-amplified TGF-β1 transfectants. The highest producer of recombinant TGF-β1 material was the TGF-β1-3/2000 cells. The amount of bioactive recombinant material secreted by $10^7$ of these cells into 5 ml of tissue culture medium over a period of 24 hours approached nearly 30 ug of TGF-β1. The amount of bioactivity detected in the conditioned supernatants for each of the transfectants correlated with the relative level of TGF-β1 mRNA observed in these cell lines.

TABLE III

AMOUNT OF BIOACTIVE TGF-β1 SECRETED BY THE CHO
TRANSFECTANTS AT VARIOUS STAGES OF MTX SELECTION

| | fg of bioactive TGF-β1 secreted/cell/24 h[a] | | |
|---|---|---|---|
| Transfectant Number | 0 nM MTX | 2 $\mu$M MTX | 20 $\mu$M MTX |
| TGF-β1–3 | 2.9 | 500 | 2800[b] |

[a]The amount of bioactive TGF-β1 secreted by a confluent 100 mm round tissue culture dish into 5 ml of serum-free DMEM was determined using the mink lung cell inhibition assay as described in Materials and Methods. Cell number was determined by counting in a hemocytometer.
[b]One confluent 100 mm round tissue culture dish (c.a. 1 × $10^{-7}$ cells) of these cells will secrete nearly 30 ug of bioactive TGF-β1 into 5 ml of serum free supernatant.

A second bioassay was also employed to further characterize the secreted recombinant TGF-β1. This assay is based on the ability of TGF-β1, in cooperation with EGF-like molecules, to stimulate the growth of NRK cells in soft agar. The results of this bioassay are shown in Table IV. The activity of the recombinant TGF-β1 is indistinguishable from that of the human natural platelet TGF-β1 used as the control.

TABLE IV

SOFT AGAR COLONY ASSAY COMPARING RECOMBINANT
TGF-β1 AND NATURAL TGF-[1]β1

| | Number of Colonies formed in Soft Agar | |
|---|---|---|
| TGF-β1 (ng/ml) | Recombinant TGF-β1 Collected from Conditioned Media | Human Platelet TGF-β1 |
| 10.0 | 260 | 251 |
| 5.0 | 263 | 247 |
| 1.0 | 225 | 211 |
| 0.5 | 193 | 182 |
| 0.1 | 50 | 85 |

[1]Normal rat kidney cells were plated in 0.3% Difco noble agar with 1 ng/ml epidermal growth factor (EGF). Eight low power fields were counted per well. No colonies formed when TGF-β1 or EGF were absent from the wells. The amount of recombinant TGF-β1 added was estimated based on the values derived in mink lung epithelial cell inhibition assay. Colony forming activity was assessed using supernatants collected from 20 $\mu$M MTX selected TGF-β1–3 cells.

7.4. ACID ACTIVATION OPTIMIZE BIOACTIVITY OF SECRETED RECOMBINANT TGF-β1

Many cell types have been found to secrete natural TGF-β1 in a latent form requiring acidification for optimal bioactivity. The bioassays presented in previous figures and tables were performed using acid dialyzed material. In order to determine if the transfected CHO cells secrete a latent biologically inactive form of TGF-β1, serum free supernatants collected from TGF-β1-3/2000 cells were dialyzed against 0.2M acetic acid or 50 mM $NH_4HCO_3$ (pH 7) and assayed for mink lung cell inhibitory activity. The results are shown in FIG. 6. Supernatants which received acid dialysis were potent in their ability to inhibit CCL-64 mink lung cells. In contrast the $NH_4HCO_3$ dialyzed samples possessed much lower levels (less than 1%) of inhibitory activity. Supernatants which were first dialyzed against $NH_4HCO_3$ and then treated by a second dialysis against 0.2M acetic acid regained their potent inhibitory activity. The dose response curve of this material was superimposable with the curve generated by samples receiving only the acid dialysis step.

7.5. IDENTIFICATION OF MATURE AND PRECURSOR FORMS OF TGF-β1 IN THE CULTURE MEDIUM OF TRANSFECTANT TGF-β1-3 CHO CELLS

Anti-peptide antibodies directed toward peptide sequences within the predicted TGF-β1 molecule were gene-rated in rabbits using synthetic peptides as immunogens. The peptide sequences which were utilized are shown in FIG. 7 which also indicates their relative locations within the TGF-β1 precursor polypeptide: TGF-$β1_{81-94}$, TGF-$β1_{225-236}$, and TGF-$β1_{369-381}$. One of the antibodies (anti-TGF-$β1_{369-381}$) was directed toward epitopes present within the mature form of the TGF-β growth factor. The other two antibodies (anti-TGF-$β1_{81-94}$ and anti-TGF-$β1_{225-236}$) are precursor-specific and are directed toward peptide sequences present only within the precursor molecule of TGF-β1.

5 7.5.1. IDENTIFICATION OF MATURE TGF-β1

Supernatants from the TGF-β-3 transfectants were collected and tested by immunoblotting with anti-TGF-$β1_{369-381}$ which readily identified authentic mature TGF-β1 (FIG. 8). Specificity was demonstrated by pre-absorbing the antibody with synthetic peptide immunogen prior to the immunoblot.

Under reducing conditions (FIG. 8A), authentic TGF-β1 migrates as a polypeptide of 12–13 kd in size. In the supernatants of MTX selected TGF-β1-3 cells, a protein comigrating with authentic TGF-β1 was readily identified (FIG. 8A). Supernatants collected from nonamplified TGF-β1-3 cells displayed nondetectable levels of recombinant β1-TGF using immunoblotting. The 20 βM MTX selected TGF-β1-3 cells appeared to produce the highest levels of mature TGF-β1, approaching 2–4 times higher than the 2 μM MTX selected cells. These increases are consistent with the results obtained for expression of MRNA levels (Table I) and bioactivity (Table IIA and IIB). Under nonreducing conditions (FIG. 8B), the recombinant TGF-β1 protein behaves as authentic TGF-β1, migrating as a dimer at 24 kd.

In addition to mature TGF-β1, larger forms of immunoreactive material were also observed. On reducing gels, these forms ranged in size from 44 kd to 56 kd (FIG. 8A). The broad nature of these immunoreactive forms may suggest extensive glycosylation. Interestingly, in the absence of reducing agent, these larger forms also appeared to migrate as a dimer 95 kd to 110 kd in size (FIG. 8B). The identification of these larger forms as precursor molecules was confirmed using the precursor-specific antibodies as described in the next subsection.

7.5.2. IDENTIFICATION OF PRECURSOR TGF-β1

Supernatants from the TGF-β1-3 transfectants were collected and tested by immunoblotting with the precursor-specific antibodies (FIG. 9). After reduction, antibodies directed toward two regions of the precursor sequences (anti-TGF-$β1_{81-94}$ and anti-TGF-$β1_{225-236}$) identified the 44 kd to 56 kd higher molecular weight forms and did not react with the mature TGF-β1 present in the supernatants (FIG. 9A). These precursor-specific antibodies in addition to identifying the larger 44 kd to 56 kd forms, also detected precursor polypeptides ranging in molecular weight from 30 kd to 42 kd (FIG. 9A). These smaller precursor molecules did not react with anti-TGF-$β1_{369-381}$ and may represent only precursor sequences. Thus, supernatants conditioned by TGF-β1-3 cells selected in MTX, contain, in addition to mature β1-TGF, larger precursor forms. These precursor sequences, since they are so highly conserved between species, may display other important biological properties. To illustrate all three TGF-β1 forms within the transfectant supernatants after reduction, an immunoblot probed with a mixture of precursor-specific antibody (anti-TGF-$β1_{225-236}$) and mature TGF-β1 specific antibody (anti-TGF-$β1_{369-381}$) is shown (FIG. 9A).

Supernatants fractionated on non-reducing SDS-polyacrylamide gels and probed with the precursor-specific peptide antibodies or with the mixture of precursor specific antibody and mature TGF-β1 specific antibody are shown in FIG. 9B. A larger molecular weight form ranging in size from 95 Kd to 110 Kd was readily identified by each of the antibodies. A mixture of precursor-specific (anti-TGF-$β1_{225-236}$) and mature TGF-β1 (anti-TGF-$β1_{369-381}$ antibodies detected the dimeric form of TGF-β1 (24 Kd) in addition to the 95–110 Kd band.

7.6. RECOMBINANT TGF-β1 CONSTITUTES THE MAJORITY OF THE SECRETED PROTEINS FROM TGF-β1-3-2000 CELLS

TGF-β1-3/0 and TGF-β1-3/2000 cells were grown to confluency, labeled in serum-free medium with [$^{35}$S]-cysteine and [$^{35}$S]-methionine for 18 hours, and the radiolabeled secreted proteins were fractionated on reducing SDS-polyacrylamide gels. The results are shown in FIG. 10. Supernatants collected from radiolabeled TGF-β1-3/0 cells showed no detectable levels of recombinant TGF-β1 proteins. In contrast, supernatants from the TGF-β1-3/2000 cells revealed four major secreted proteins not found in the initial TGF-β1-3/0 transfectant. Three of these proteins migrated identically to the mature and precursor forms of TGF-β1 identified by immunoblotting. The other protein which was heavily labeled with [$^{35}$S]-amino acids and released by the TGF-β1-3/2000 cells migrates at a molecular weight of 22 Kd. Amino-terminal sequence analysis of this protein revealed its identity as dihydrofolate reductase.

8. EXAMPLE: CHARACTERIZATION OF THE TGF-β1 GENE PRODUCT

The following examples present data on the purification and extensive characterization of the rTGF-β1 products synthesized by CHO-TGF-p-3-2000 cells. The results indicate that rTGF-β1 is synthesized in CHO cells as pre-pro-TGF-β1 which is processed at the carboxy-terminal side of Gly-29 and Arg 278, that rTGF-β1 precursor is glycosylated and phosphorylated but that the mature protein is not, that rTGF-β1 possesses a specific activity equivalent to that of natural TGF-β1, and that mature rTGF-β1 is a potent inhibitor of tumor cell growth in vitro and in vivo.

8.1. GLYCOSYLATION AND PHOSPHORYLATION OF THE rTGF-β1 PRECURSOR

The structural features of the rTGF-β1 precursor relevant to this section are illustrated in the line diagram shown in FIG. 11A. A hydrophobic leader cleaved from the protein at amino acid residue 29 produces a 361 amino acid polypeptide indicated as 'a' in FIG. 11A. Subsequent modification and cleavage would result in mature rTGF-β1 monomer (labeled 'c' in FIG. 11A) and a 249 amino acid protein consisting entirely of amino terminal precursor residues ('b' in FIG. 11A).

The cell line used in this example is TGFβ3-2000 and the TGF-β1 related proteins secreted by these cells, analyzed by immunoblotting, are shown in FIG. 11B. As described in Section 7.5., supra, supernatants derived from TGFβ3-2000 cells contain a large 95 Kd-110 Kd form of rTGF-β1 as well as the mature 24 Kd protein dimer when analyzed by SDS-polyacrylamide gels under non-reducing conditions; when analyzed under reducing conditions, these supernatants are found to contain a 44 Kd–56 Kd band ('a' in FIG. 11B, lane 2), a 30 Kd–42 Kd band ('b' in FIG. 11B, lane 2) and a 12 Kd band ('c' in FIG. 11B, lane 2) which is the mature TGF-β1 monomer. Evidence that bands a, b, and c shown in FIG. 11B contain the regions of the rTGF-β1 precursor shown in FIG. 11A is presented in Section 7.5., supra. These bands can be easily visualized when [$^{35}$S]-methionine and [$^{35}$S]-cysteine labeled supernatants from TGF-β3-2000 cells are analyzed directly by SDS-polyacrylamide gel electrophoresis followed by fluorography (FIG. 11C, lane 1 and FIG. 11D, lane 1); these bands are not detected in supernatants from non-transfected CHO cells.

The diffuse nature of bands 'a' and 'b' shown in FIG. 11 suggested that they may be glycosylated. To investigate this possibility, TGFβ3-2000 cells were labeled with [$^{3}$H]-glucosamine and cell-free supernatants were analyzed by SDS-polyacrylamide gel electrophoresis followed by fluorography. FIG. 11C (lane 2) shows that the 95–110 Kd form was labeled; no label was detected in the mature 24 Kd protein dimer. When analyzed under reducing conditions (FIG. 11D, lane 2), bands 'a' and 'b' were labeled. No label was found in band 'c'. Thus, the rTGF-β1 precursor is glycosylated while the mature of 12 Kd monomer is not.

The nature of this glycosylation was further investigated by treating supernatants from TGFP3-2000 cells with various glycolytic enzymes followed by fractionation of the digestion products on SDS-polyacrylamide gels. FIG. 12A shows an immunoblot analysis of these digests. Neuraminidase treatment caused bands 'a' and 'b' to migrate as faster but still diffuse bands (FIG. 12A, lane 3) indicating the presence of sialic acid residues. Endoglycosidase H, which predominantly cleaves high-mannose oligosaccharide chains, had no noticeable effect (FIG. 12A, lane 4). Digestion with N-glycanase, which removes N-linked carbohydrate, caused bands 'a' and 'b' to migrate as two sharp bands, the largest of which had a molecular weight of approximately 39 Kd (FIG. 12A, lane 2). As expected, no change in the migration of the mature 12 Kd monomer was noted. The same results were obtained using [$^{35}$S]-cysteine labeled supernatants from TGFβ3-2000 cells (FIG. 12B). In order to determine the size of the unmodified TGF-β1 precursor, a 1350 base pair Pst I-Eco RI fragment containing the entire coding region of TGF-β1 (Sharples et al., 1987, DNA 6:239–244) was subcloned into pSP64 and transcribed with SP6 polymerase (Kreig et al., 1984, Nucleic Acids Res. 18:7057–70). Analysis of these transcripts on agarose-urea gels indicated that a single RNA species was produced (FIG. 13A) which programmed the synthesis of a 42 Kd polypeptide in a message-dependent reticulocyte cell-free translation system (FIG. 13B). Longer exposure of this gel revealed the presence of a minor 40 Kd product. The size (42 Kd) of the major cell-free translation production is in good agreement with that expected for a 390 amino acid protein and most likely corresponds to the unmodified TGF-β1 polypeptide backbone. The 39 Kd band shown in FIG. 12A (lane 2) and FIG. 12B (lane 4) would then represent the de-glycosylated protein core of rTGF-β1 minus the hydrophobic leader sequence ('a' in FIG. 11A). The band below this corresponds to the deglycosylated band 'b' in FIG. 11A.

Incubation of TGFβ3-2000 cells in the presence of [$^{32}$P]-orthophosphate and subsequent fractionation of cell-free supernatants on SDS-polyacrylamide gels indicated that the rTGF-β1 precursor, but not the mature 12 Kd monomer, was phosphorylated (FIG. 11E). Thin layer electrophoresis of acid hydrolysates showed that most of the phosphate was not attached to serine, threonine or tyrosine (spots X, Y, Z, FIG. 11F). Data obtained by example Section 9, infra, demonstrates that phosphate is incorporated into asparagine-linked complex carbohydrate moieties as mannose-6-phosphate. The implications of this finding are also discussed.

8.2. PURIFICATION OF BIOLOGICALLY ACTIVE TGF-β1

CHO cell transfectants expressing rTGF-β1 (TGF-β3-2000 cells) were propagated and passaged as described in Section 7, supra. Roller bottles (850 cm$^{2}$) containing 50 ml of Dulbecco's modified Eagles' medium (DMEM) supplemented with fetal bovine serum (10% v/v), penicillin (100 U/ml), streptomycin (100 μg/ml), L-proline (150 μg/ml) and methotrexate (20 μM) were seeded with one confluent 150 cm$^{2}$ round tissue culture dish of TGF-β3-2000 cells and grown at 37° C. After cells attached and reached confluency, they were rinsed twice with 50 ml of serum-free medium supplemented as above and then incubated for 24 h in 50 ml of serum-free medium supplemented additionally with ascorbate and reduced glutathione at 100 μg/ml and 20 μg/ml, respectively.

Serum-free supernatants were collected from roller bottles, centrifuged at 200×g to remove cellular debris, and immediately adjusted to 10 mg/liter phenylmethylsulfonyl fluoride, 50 trypsin inhibitory units/liter of aprotinin (Sigma), and 0.2M acetic acid. Supernatants were concentrated 40-fold by ultrafiltration (YM10 membrane, 10,000 molecular weight cut-off; Amicon) and the resulting concentrate dialyzed extensively against 0.2M acetic acid.

The dialyzed material was lyophilized and stored at −20° C. prior to purification.

Conditioned medium was first fractionated by gel permeation chromatography. A representative elution profile is shown in FIG. 14. Greater than 95% of the biological activity eluted, based on marker proteins, at a molecular weight of approximately 15,000. The same elution pattern was observed with nTGF-β1 using the same column conditions. The low apparent molecular weight of TGF-β1, as determined by gel permeation chromatography, may be due to the tightly folded structure of the dimeric growth factor molecule or to nonspecific adsorption. High molecular weight activity was observed in void volume of the column and accounted for less than 5% of the total applied activity. SDS-PAGE under non-reducing conditions of pool A and B revealed that the majority of the biological activity eluted as a 24 KDal polypeptide species, whereas the minor activity eluted as a large 95–110 KDal molecular weight component (data not shown).

To confirm that the 24 KDal component represented the properly processed rTGF-β1, we purified this species to homogeneity using reversed-phase HPLC for subsequent characterization. Pool B was fractionated on a C18 μBondapak support (FIG. 15). The biologically active component eluted on a shallow acetonitrile gradient as a homogeneous peak with the same retention time as nTGF-β1. Analysis on SDS-polyacrylamide gels under non-reducing and reducing conditions demonstrated that this active component was homogeneous, comigrating with nTGF-β1 isolated from bovine spleen (FIG. 16). rTGF-P1 was further characterized by protein sequence analysis (Table V).

TABLE V

AMINO-TERMINAL SEQUENCE ANALYSIS OF rTGF-†1 POLYPEPTIDES

| | Polypeptide[a] a | Polypeptide[a] b | | | | HPLC Purified Mature rTGF-†1[b] | |
|---|---|---|---|---|---|---|---|
| Cycle | Yield (pmol) | Yield (pmol) | Position (Residue) | Yield (pmol) | Position (Residue) | Yield (pmol) | Position (Residue) |
| 1 | 42.9 | 93.8 | 30 (Leu) | 40.1 | 279 (Ala) | 27.4 | 383 (Ile) |
| 2 | 17.0 | 29.1 | 31 (S = er) | 36.1 | 380 (Leu) | 27.3 | 384 (Val) |
| 3 | 13.2 | 27.0 | 32 (Thr) | 26.8 | 281 (Asp) | 13.5 | 385 (Arg) |
| 4 | N.D. | N.D. | 33 (Cys)[c] | 10.9 | 282 (Thr) | 7.3 | 386 (Ser) |
| 5 | 34.9 | 49.4 | 34 (Lys) | 15.2 | 283 (Asn) | N.D. | 387 (Cys)[c] |
| 6 | 12.5 | 20.0 | 35 (Thr) | 14.8 | 284 (Tyr) | 8.1 | 388 (Lys) |
| 7 | 21.1 | 32.5 | 36 (Ile) | N.D. | 285 (Cys)[c] | N.D. | 389 (Cys)[c] |
| 8 | 17.9 | 38.8 | 37 (Asp) | 14.6 | 286 (Phe) | 4.7 | 390 (Ser) |

[a]Polypeptides a and b were electroeluted from coomassie blue stained gel similar to that shown in FIG. 1b prior to amino-terminal sequence analysis.
[b]Sequence of purified mature rTGF-†1. The rTGF-†1 was cleaved with CNBr and results indicate simultaneous sequences of amino- and carboxy-ends of the growth factor.
[c]N.D.: Not determined.

The purified polypeptide was chemically cleaved with cyanogen bromide prior to sequencing. Since mature TGF-β1 contains only one methionine at residue 382, two sequences were obtained simultaneously; one corresponding to the amino-terminal sequence of the growth factor (beginning at Ala-279) and one representing the carboxy-terminal 8 amino acids (beginning at ILe-383). Our results (Table V) demonstrate that biologically active rTGF-β1 is properly processed.

A summary of the purification steps of rTGF-β1 is shown in Table VI. The growth factor was purified greater than 30-fold in two purification steps. In this particular experiment, the overall yield was 54% and resulted in 0.65 mg of rTGF-β1 per liter of conditioned culture medium.

Processing of other preparations resulted in greater than 85% recovery of biologically active recombinant protein, a yield of more than 1 mg per liter.

TABLE VI

PURIFICATION OF MATURE rTGF-β1 FROM CONDITIONED MEDIUM

| Fraction | Protein[b] (mg) | Units[a] | Specific Activity Units/mg | Percent Yield |
|---|---|---|---|---|
| Conditioned Medium[c] | 39.0 | 14 × 10[7] | 3.6 × 10[6] | 100 |
| TSK (Fraction B) | 1.37 | 8.3 × 10[7] | 61 × 10[6] | 59 |
| HPLC-C18 | 0.65[d] | 7.5 × 10[7] | 119 × 10[6] | 54 |

[a] One unit of activity is defined in Experimental Procedures.
[b]Protein determined assuming 1 absorbance unit at 280 nm = 1 mg/ml protein.
[c]Started with one liter of conditioned medium.
[d]Calculated from amino acid analysis.

8.3. PURIFICATION AND NATURE OF rTGF-β1 PRECURSOR

The rTGF-β1 precursor was purified by taking advantage of its glycosylated nature. Precursor eluting in the void volume of a TSK-250 colum (Pool A) was dialyzed against neutral buffer (50 mM $NH_4HCO_3$, pH 7.8), and centrifuged at 15,000×g prior to fractionation on a conconavalin A lectin column. A column containing one ml of conconavalin A covalently bound to Sepharose 4B (Pharmacia) was extensively washed with phosphate buffered saline (PBS) and equilibrated with 50 mM $NH_4HCO_3$, pH 7.0. Samples to be absorbed were loaded and recirculated four times through the column before washing with ten volumes of PBS. Specifically bound material was eluted with 100 mM methyl-α-D-mannopyranoside in PBS.

Conconavalin A-bound pecursor was eluted specifically with α-methyl mannoside. An SDS-polyacrylamide gel profile of the purified precursor stained with Coomassie blue is shown in FIG. 16. The eluted protein migrated at a molecular weight of between 95–120 KDal. This large form was reactive with antibodies directed toward the precursor sequences and mature growth factor. No contaminating mature rTGF-β1 was detected in this preparation, even on overloaded SDS-polyacrylamide gels.

Although the mature, dimeric growth factor was absent from the preparation, the purified precursor when analyzed by reducing SDS-PAGE revealed a 14 KDal species which comigrated with monomeric rTGF-β1 (FIG. 16). Also apparent on the gels were the two precursor species, pro-TGF-β1 (30-390) and the 30–42 KDal pro region of the precursor (30-278; see also FIG. 17). Further attempts to fractionate this larger complex into separate components were unsuccessful. Amino terminal sequence analysis of the conconavalin A purified material revealed two amino terminal sequences, one beginning at Leu-30 and the other at Ala-279. These results strongly suggest that the 95–120 KDal rTGF-β1 precursor purified from the conditioned medium of the CHO cells represents a mixture of pro-TGF-β1 (30-390), the pro region of the precursor (30-278), and the mature chain of rTGF-β1 (279-390) all interlinked by disulfide-bonds. To confirm this observation, we digested the precursor with CNBr and purified the CNBr peptides to establish the chemical nature of this complex. TGF-β1-precursor (800 pmol) was dissolved in 30 µl of 70% formic acid and 16 µl of a solution containing 15 mg CNBr in 100 11 70% formic acid was added (Gross and Witkop, 1962, J. Biol. Chem. 237:1856–1860). The reaction proceeded under nitrogen for 4 hours at 30° C. in the dark. The digest was chromatographed on a Bio-Sil TSK-250 gel permeation chromatography column equilibrated in 0.1% trifluoracetic acid (TFA) containing 40% acetonitrile as described (Ikeda et al., 1987, Biochemistry 26:2406–2410). Reversed-phase HPLC was performed on a μ Bondpak C-18 column (3.9×300 mm, 10 μm particle size; Waters) with a linear gradient composed of 0.05% TFA in water as starting buffer and 0.045% TFA acetonitrile as limiting buffer. Fractions were collected in polypropylene tubes to minimize losses from non-specific adsorption. A TSK-250 elution profile of CNBr-cleaved rTGF-β1 precursor is shown in FIG. 18. The various peaks were identified by amino acid sequencing. A major CNBr peptide fragment containing a disulfide bridge between a precursor cysteine residue and the cysteine residue of the mature growth factor is M(30-38/279-382/383-390) and its amino-terminal sequence analysis is shown in Table VII. This particular peptide fragment involves Cys-33 of the precursor and one of the cysteine residues of the mature growth factor. The amino-terminal CNBr peptide M(30-38/262-382/383-390) represents a disulfide-linked peptide involving pro-TGF-β1.

TABLE VII

AMINO-TERMINAL SEQUENCE OF DISULFIDE CROSS-LINKED FRAGMENT CB PEPTIDE I DERIVED FROM rTGF-†1 PRECURSOR

| Cycle | Yield (pmol) | Position (Residue) | Yield (pmol) | Position (Residue) | Yield (pmol) | Position (Residue) |
|---|---|---|---|---|---|---|
| 1 | 22.6 | 30 (Leu) | 25.5 | 279 (Ala) | 16.0 | 383 (Ile) |
| 2 | 10.6 | 31 (Ser) | 28.3 | 280 (Leu) | 18.5 | 384 (Val) |
| 3 | 11.3 | 32 (Thr) | 21.2 | 281 (Asp) | 8.5 | 385 (Arg) |
| 4 | N.D. | 33 (Cys)[a] | 14.9 | 282 (Thr) | 9.3 | 386 (Ser) |
| 5 | 14.8 | 34 (Lys) | 18.9 | 282 (Asn) | N.D. | 387 (Cys)[a] |
| 6 | 10.9 | 35 (Thr) | 21.3 | 284 (Tyr) | 14.7 | 388 (Lys) |
| 7 | 13.3 | 36 (Ile) | N.D. | 285 (Cys)[a] | N.D. | 389 (Cys)[a] |
| 8 | 12.3 | 37 (Asp) | 22.1 | 286 (Phe) | 5.6 | 390 (Ser) |

[a]N.D.: Not determined.

8.4. AMINO TERMINAL SEQUENCE OF rTGF-β1 POLYPEPTIDES

Automated sequence analysis was performed on a model 475A amino acid sequencer (Applied Biosystems).

Phyenylthiohydantoin-amino acid derivatives were separated by reversed phase HPLC, on-line, on a model 120A PTH analyzer (Applied Biosystems) as described (Marquardt et al., 1987, J. Biol. Chem. 262:12127–12136).

Serum-free conditioned media from CHO-TGF-β1-3/2000 cells expressing high levels of simian rTGF-β1 was electrophoresed on SDS-PAGE under reducing conditions. Coomassie blue staining reveals the three molecular forms of rTGF-β1 secreted by these cells (FIG. 17). The largest form, a broadly migrating species ranging in size from 44–56 KDal ("a" in FIG. 17) and possessing immunological epitopes derived from TGF-β1 precursor and mature TGF-β1 (Section 7.5, supra), most likely represents unprocessed TGF-β1 precursor. The 30–42 KDal polypeptide ("b" in FIG. 17) only contains precursor-derived epitopes (Section 7.5, supra) indicating that this species has undergone proteolytic cleavage separating it and the mature TGF-β1 form. The 14 KDal species ("c" in FIG. 17) represents the mature, fully processed TGF-β1 monomer. Recombinant precursor proteins ("a" and "b" in FIG. 17) were electroeluted from acrylamide slices and characterized by amino-terminal sequence analysis. The results are shown in Table V supra. Sequence analysis revealed that the two larger precursor forms have identical amino-terminal sequences. Comparison of this sequence with that predicted from the simian TGF-β1 cDNA (Sharples, et al., 1987, DNA 6:239–244) indicates that both larger proteins have undergone specific proteolytic cleavage at Gly-29/Leu-30 removing the first 29-amino acids of the intact pre-pro-TGF-β1 molecule. Cleavage of this hydrophobic 29-amino acid leader sequence is most likely the result of a signal peptidase. The Gly-29/Leu-30 peptide bond is the predicted signal peptide cleavage site (Von Heijne, 1986, Nucleic Acids Res. 14:4683–4690). Based on these results, the 44–56 KDal TGF-β1 polypeptide ("a" in FIG. 17) represents pro-TGF-β1 (30-390) whereas the 30–42 KDal species ("b" in FIG. 17) corresponds to the pro region of the precursor (30–278) lacking the signal peptide and mature TGF-β1 sequences. Sequence analysis of the 14 KDal polypeptide (data not shown) revealed an intact amino-terminus beginning at Ala-279 of the mature growth factor indicating that CHO-TGF-β1-3/2000 cells properly process the simian rTGF-β1 at the dibasic cleavage site. A summary of a proposed processing scheme for TGF-β1 is presented in FIG. 20.

8.5. BIOLOGICAL ACTIVITY IN VITRO

Purified mature and precursor forms of rTGF-β1 were tested for biological activity on mink lung epithelial cells as described in Section 7.1.6., supra. The biological activity profiles of mature and precursor rTGF-β1 and natural TGF-β1 from bovine spleen are presented in FIG. 19. Molarity calculations were based on predicted amino acid compositions (for precursor rTGF-β1, the amino acid composition of pro-TGF-β1 was used). The results indicate that mature rTGF-β1 is a potent inhibitor of mink lung cell proliferation (1–2 pM for half-maximal inhibition) and has an activity curve which is superimposable with that obtained for natural TGF-β1. In other words, the recombinant TGF-β1 of the invention and natural TGF-β1 possess identical specific activities. In contrast, the precursor preparation was 50-fold less active than the mature growth factor (50–60 pM for half-maximal inhibition) and a comparison of the inhibition profiles in FIG. 19 revealed a slight difference in the dose-response curves, suggesting receptor affinity differences between the mature and precursor forms.

8.6. BIOLOGICAL ACTIVITY IN VIVO

The effects of TGF-β1 in vivo are largely unknown although its role in inhibiting mammary gland growth (Silberstein and Daniel, 1987, Science 237:291), in wound healing (Sporn et al., 1983, Science 219:1329), and in embryonic development (Weeks et al., 1987, Cell 51:861) have been suggested. Both naturally derived TGF-β1 and TGF-β2 from bone (Seyedin et al, 1986, J. Biol. Chem. 261:5693; Seyedin et al., 1987, J. Biol. Chem. 262:1946) and recombinant Simian TGF-β1 cloned (Sharples et al., 1987, DNA 6:239–244) and expressed (Gentry et al., 1987, Mol. Cell. Biol. 7:3418) in CHO-TGF-β1-3-2000 cells are potent inhibitors of DNA synthesis in a variety of established tumor cell lines of human epithelial origin (Ranchalis et al., 1987, Biochem. Biophys. Res. Comm. 148:783). In this study, we present in vivo evidence that TGF-βis also tumorstatic for a human lung tumor grown in athymic nude mice. Particularly striking is the induction by TGF-β of a differentiated-like cellular phenotype in the inhibited tumor cells. The human lung carcinoma cell line designated A549, established from a male Caucasian with an adenocarcinoma of the lung, is a responsive target (in vitro) for inhibition by picomolar concentrations of natural TGF-β1 or TGF-β2 and the recombinant TGF-β1 of the invention. Nude mice were subcutaneously inoculated with A549 cells; palpable tumors developed in approximately 80% of the animals in three weeks. FIG. 21 shows the effect of TGF-β1 and TGF-β2 treatment on the further growth of A549 tumors in these mice. Each experimental group contained five animals and values on the ordinate represents the average tumor measurements in three dimensions (volume). Day 1 corresponds to the first day the groups received treatment; test compounds were subcutaneously injected in the vicinity of the tumor but not into the tumor itself. Animals in control groups received injections of bovine serum albumin in a carrier solution identical to TGF-β treated tumor-bearing animal groups. Tumor volume in control groups doubled approximately every 7–8 days. Similar doubling times were also observed in separate experiments in tumor-bearing animals which received a biologically inactive synthetic peptide. In contrast, successive injections, corresponding to those days as indicated on the abscissa, of 200 ng of TGF-β1 and TGF-β2 (1.4 μg total per treatment regimen for each) were tumorstatic and retarded the further growth of tumors. As shown in FIG. 21, TGF-β1 appeared slightly more effective than TGF-β2. In a separate experiment, the dose response of TGF-β1 on A549 tumor inhibition was examined (FIG. 21). Values represent average tumor volumes in TGF-β treated animals relative to tumor volumes from mock-treated animals. About 25% inhibition was observed at the lowest dose tested (12.5 ng per injection) of TGF-β1. At higher doses, 50 and 200 ng per injection, a correspondingly greater inhibition in tumor growth was observed (37% and 60% respectively). In some experiments, the larger the tumor volume at day 1, the lower the percent reduction in inhibited tumor volume relative to tumors derived from control groups. Animals receiving even the highest doses of TGF-β (1.4 μg total after 20 days) exhibited no gross manifestations of TGF-β toxicity. As shown in FIG. 23, TGF-β1 treated animals displayed normal characteristics; no apparent abnormalities were found on gross examination of major organs during biopsy. The inset is representative of the size of tumors removed from each group at the end of the experiment (day 20) prior to submission for pathology. Tumors removed from experimental animals (day 21, FIG. 21) had a greater than 90% reduction in average net weights.

Recombinant Simian TGF-β1 purified to homogeneity from serum-free culture supernatants exhibits an in vitro dose response inhibition curve similar to the natural (bovine bone) molecule when tested on a variety of tumor cells including the A549 tumor cells used in these studies. A comparison of the effect of recombinant and natural TGF-β1 on the growth of A549 human lung carcinoma in athymic mice is shown in Table VIII. The recombinant product was more effective in inhibiting tumor growth than bone-derived TGF-β1, 60% inhibition compared to 46% inhibition.

TABLE VIII

COMPARISON OF THE EFFECTS OF RECOMBINANT
AND NATURAL TGF-β1 ON TUMOR GROWTH

| TGF-β1 | Tumor size* | | |
|---|---|---|---|
| | Control | Treated | % Inhibition |
| Recombinant | 105.4 | 42.6 | 60.0 |
| Bone-derived | 83.4 | 45.4 | 46.0 |

*Protocol for these experiments is as described in legend to FIG. 21 except that tumors were measured only in two dimensions. Values represent average tumor area in animals from each group. Purified rTGF-β1, and natural TGF-β1 from bovine bone (Seyedin et al., 1986, J. Biol. Chem. 261:5693) were injected peritumorally (200 ng/injection, 1 μg total). Measurements represent average tumor size at day 17 post treatment.

Tumors were excised from control and treated animal groups, fixed and submitted for histological pathological examination. As shown in FIG. 24, panel A, under low power, trichrome stained control tumor sections demonstrate predominantly large areas of necrosis dispersed through a rather heterogeneous field of different cell types, mostly columnar epithelial. A large number of blood vessels are also observed. In contrast, similarly prepared sections of TGF-β1 inhibited tumor specimens "b" in FIG. 24 demonstrated little necrosis, more apparent organization, and a different distribution of cell types. Particularly apparent was the increase in connective tissue banding (blue staining) relative to control tumor specimens. In addition, general vascularity appeared diminished relative to control tumors. When examined under higher magnification, non necrotic areas of control tumors ("c" in FIG. 24) exhibited a combination of epithelial-like and poorly differentiated cell types, also apparent is the high density of stained nuclei indicating a high rate of tumor cell proliferation. In contrast, TGF-β-treated tumor specimens ("d" in FIG. 25) presented a significantly different picture. The predominant cell type seen is large and round; nuclei are more dispersed in the field and display the crescent morphology characteristic of goblet cells (a normal lung cell type that secretes mucins). Although some mucous secreting cells were observed in control tumor specimens they represented only a minor subpopulation of cells. Also more prevalent in sections of TGF-β inhibited tumors ("d", inset, in FIG. 25) were scattered foci of columnar epithelial cells organized around blood vessels.

The mucous secreting nature of the goblet-like cell type from treated tumors was confirmed by periodic acid Schiff base stain (PAS). Control tumor sections ("a" in FIG. 25) revealed a few scattered areas of high glycoprotein density. Dramatically amplified PAS staining intensity was seen throughout TGF-β-treated tumor sections ("b" in FIG. 25). A more differentiated and organized phenotype is also evident. Both control and TGF-β-treated tumor sections were also examined for glycosaminoglycans (GAGs) as measured by staining with Alcian blue at pH 2.5. Control specimens ("c" in FIG. 25) exhibited very light staining whereas TGF-β-treated specimens ("d" in FIG. 25) showed significantly more, suggesting a higher level of hyaluronic acid synthesis and deposition.

9. EXAMPLE: IDENTIFICATION OF MANNOSE-6-PHOSPHATE IN TWO ASPARAGINE-LINKED SUGAR CHAINS OF rTGF-β1 PRECURSOR

The following example demonstrates that all three potential glycosylation sites (Asn-82, -136 and -176) in simian rTGF-β1 are used for carbohydrate addition and that phosphorylation occurs within the oligosaccharide side chains. The results suggest an independent functional role of the rTGF-β1 precursor.

9.1. MATERIALS AND METHODS
9.1.1. MATERIALS

Sequencer reagents were obtained from Applied Biosystems. Solvents for HPLC were from Burdick and Jackson. CNBr was from Kodak; 4-vinylpyridine was from Aldrich Chemical Co.; all other chemicals were reagent grade. *Staphylococcus aureus* V8 protease was from Miles Laboratories; L-(tosylamido-2-phenyl) ethyl chloromethyl ketone-treated trypsin was obtained from Worthington.
9.1.2. CELL CULTURE The TGF-⊖-3-2000 cell line was propagated as described in Section 7.1.1., supra. Individual clones were isolated by limiting dilution in 96 well plates. One clone, TGF-β-3-

2000-17 (hereafter referred to as clone 17) was found to produce approximately 2 μg/ml of active TGF-β1 and was used for further analysis. These cells were routinely passaged in Dulbecco's modified Eagle's medium containing 10% fetal bovine serum, 150 μg/ml L-proline, 100 U/ml penicillin, 100 μg/ml streptomycin, and 20 μM methotrexate.

9.1.3. RADIOLABELING

Clone 17 cells were grown to confluence, washed three times in phosphate-free medium minus serum and incubated in the same medium for 30 minutes at 37° C. The medium was then replaced with fresh methionine, cysteine and serum-free medium containing 200 μCi/ml [$^{35}$S]-methionine and [$^{35}$S]-cysteine (NEN, Boston, Mass.) and cells were incubated for 4 hours at 37° C. For labeling with [$^{3}$H]-sugars, cells were grown to confluence, washed with serum-free medium and labeled for 20 hours in serum-free medium containing 100 μCI/ml of [$^{3}$H]-glucosamine or [$^{3}$H]-mannose (NEN, Boston, Mass.). Radiolabeled serum-free supernatants were collected, centrifuged at 4000×g for 10 minutes, dialyzed extensively against 0.2M acetic acid and lyophylized.

9.1.4. POLYACRYLAMIDE GEL ELECTROPHORESIS

Dried pellets were analyzed under reducing conditions on a 15% SDS-polyacrylamide or on 7.5–15% gradient SDS-polyacrylamide gels as described (Laemmli, 1970, Nature 227:680–685). Gels were stained with Coomassie blue, fluorographed (for [$^{35}$S]- and [$^{3}$H]-labeled proteins (Chamberlain, 1979, Anal. Biochem. 98:132–136) and exposed to Cronex-4 X-ray film. Alternatively, lyophylized samples were digested with N-glycanase (Genzyme, Boston, Mass.) for 16 hours at 37° C., using conditions recommended by the manufacturer, prior to polyacrylamide gel electrophoresis.

9.1.5. ACID HYDROLYSIS

[$^{32}$P]-labeled rTGF-β1 precursor, and [$^{32}$P]-labeled glycopeptides were hydrolyzed in 6N HCl for 2 hours at 95° C. The products were separated by electrophoresis at pH 1.9 and 3.5 and detected by autoradiography as described (Cooper et al., 1983, Meth. Enzymol. 99:387–402). Alternatively, electrophoresis at pH 8.9 (1% ammonium carbonate) was followed by chromatography (65% isobutyric acid, 5% pyridine, 3% acetic acid, 2% butanol, 25% water). Internal standards (phosphoserine, phosphothreonine, phosphotyrosine) were detected by ninhydrin staining. Mannose-6-phosphate was detected by spraying with 70% perchloric acid: 1M HCl: 4% ammonium molybdate: acetone (5:10:25:60), drying, and exposing to ultraviolet light.

9.1.6. S-PYRIDYLETHYLATION

For reduction, 50 μg of TGF-β1 precursor and 225,000 cpm of [32 P]-labeled rTGF-β1 precursor, derived from serum-free supernatant of clone 17 cells was treated with dithiothreitol (20 mM) in 100 μl of 0.4M Tris-HCl buffer, pH 8.5, containing 6M guanidine HCl, 0.1% Na$_2$EDTA, for 2 hours at 50° C. and subsequently S-pyridylethylated with 4-vinylpyridine (100 mM) for 4 hours at 22° C. The reaction mixture was acidified to pH 2.0 with 20% TFA and desalted on an RP-300 column (2.1×30 mm; Applied Biosystems) using a TFA/acetonitrile gradient for elution. The concentration of acetonitrile was increased linearly from 0.1% TFA in water to 60% acetonitrile containing 0.08% TFA over 1.5 hours, at a flow rate of 100 μl/min at 35° C.

9.1.7. CHEMICAL AND ENZYMATIC CLEAVAGE

For CNBr cleavage at methionyl residues, 650 pmol of S-pyridylethylated TGF-β1 precursor and 160,000 cpm of [$^{32}$P]-labeled S-pyrindylethylated TGF-β1 precursor were dissolved in 30 μl of 70% formic acid and 4 l of a solution containing 60 mg CNBr in 100 μl of 70% formic acid was added (Gross and Witkop, 1962, J. Biol. Chem. 237:1856–1860). The reaction preceeded under a nitrogen cushion for 4 hours at 30° C. and continued for an additional 18 hours at 22° C. in the dark.

Cleavage with S. aureus V8 protease was done in 40 μ of 0.1M Tris-acetic acid buffer, pH 8.0, containing 3M urea at 37° C. for 10 hours. The enzyme/substrate ratio was 1 to 10 (wt/wt). Trypsin digestion of pool A and pool B (FIG. 31-A) was done in 40 μl of 0.1M Tris-acetic acid buffer, pH 8.0, containing 30% acetonitrile, at an enzyme substrate ratio of 1 to 20 at 37° C. for 15 hours. The enzymatic digests were acidified with 20% TFA to pH 2.0 and separated by rpHPLC.

10 9.1.8. PEPTIDE PURIFICATION

HPLC was performed on a Waters HPLC system consisting of two M 6000 A pumps, a system controller, a U6K injector, a model 441 fixed wavelength detector (214 nm), or on a model 130A separation system (Applied Biosystems), and a chart recorder. Gel permeation chromatography on a Bio-Sil TSK-250 column (7.5×600 mm; Bio-Rad Laboratories) was carried out in 0.1% TFA containing 40% acetonitrile at a flow rate of 0.25 ml/min. Peptide purification by rpHPLC was carried out at 35° C. on a RP-300 column (2.1×30 mm; Applied Biosystems). Linear acetonitrile gradients composed of 0.1% TFA in water as starting buffer and acetonitrile containing 0.08% TFA as limiting buffer were employed for elution. Peptides were collected manually. V8 protease peptides indicated by E, and trypsin peptides indicated by T could be used for sequence analysis without further purification.

9.1.9. AMINO ACID SEQUENCE ANALYSIS

Automated sequence analysis was performed on a model 475A amino acid sequencer (Applied biosystems) using the RUN470-1 program. A total of 1.5 mg BioBrene Plus (Applied Biosystems) was applied and subjected to two precycles of Edman Degradation prior to sample application. Conversion of the thiazolinone derivatives to phenylthiohydantoin amino acids was carried out with 25% TFA. Phenylthiohydantoin amino acid derivatives were separated by rpHPLC, on-line, on a model 120A PTH analyzer (Applied Biosystems), as described (Marquardt et al., 1987, J. Biol. Chem. 262:12127–12131).

9.1.10. BINDING STUDIES

TGF-β1 precursor was purified by gel permeation chromatography on a Bio-Sil TSK-250 column and rpHPLC on a Vydac C4 column. Approximately 6 μg of purified precursor were iodinated with 1 mCi of [$^{125}$I] as described (Frolik et al., 1984, J. Biol. Chem. 259:10995–11000). A solid phase receptor assay was used to measure binding of [$^{125}$I]-TGF-β1 precursor to the mannose-6-phosphate/IGF-II receptor (Roth et al., 1987, Biochem. Biophys. Res. Commun. 149:600–606). Polyvinylchloride microtiter wells were sequentially coated with 40 μl protein A (20 μl in 20 mM NaHCO$_{31}$ pH 9.6), rabbit antibodies to the IGF-II receptor (50 μg/ml) and 500 ng of purified human fetal brain receptor (id.). The buffer used for all washes contained 50 mM HEPES, pH 7.8, 50 mM NaCl, 0.1% Triton-X-100, 0.1% Tween 20 and 0.1% bovine serum albumin. The wells were then incubated with 5% non-fat dry milk for 20 min at 4° C. and the radiolabeled TGF-β1 precursor was added to each well. After 3 h at 4° C., wells were washed four times, cut out, and counted. Non-specifically bound counts were determined in the absence of receptor and subtracted before calculating the percent inhibition.

9.2. RESULTS

The three structural forms of rTGF-β1 secreted by clone 17 cells are illustrated by the line diagram in FIG. 26A. Also indicated in FIG. 26A are the three potential asparagine-linked glycosylation sites predicted from the DNA sequence of simian TGF-β1 precursor: Asn-82, -136 and -176 (FIG. 1 and Sharples et al., 1987, DNA 6:239–244).

FIG. 26B shows an autoradiogram of [$^{35}$S]-labeled proteins secreted by clone 17 cells analyzed by SDS-polyacrylamide gel electrophoresis. Proteins a, b and c can be easily visualized. Precursor proteins a and b can be labeled with [$^{32}$H]-glucosamine, [3H]-mannose, and [2 P]-phosphate (FIG. 26C, 26D and 26E) indicating that rTGF-β1 precursor proteins a and b, but not mature rTGF-β1 (protein c), are both phosphorylated and glycosylated. Digestion of [$^{35}$S]-labeled precursor proteins with N-glycanase resulted in a shift in migration of bands a and b to sharper and faster migrating bands, the largest of which had a molecular weight of approximately 39,000 (FIG. 27A, lane 2), consistent with the calculated molecular weight of 41,200 for the TGF-β1 precursor protein a. Digestion of [$^{32}$P]-labeled proteins with N-glycanase and subsequent fractionation of the digest by SDS-polyacrylamide gel electrophoresis indicated that the enzyme has removed all the label from the rTGF-β1 precursor proteins (FIG. 27B, lane 2), suggesting that [$^{32}$P]-label was incorporated into asparagine-linked oligosaccharides.

The glycosylated and phosphorylated rTGF-β1 precursor proteins a and b were subjected to cyanogen bromide cleavage and subsequent enzymatic digestion for further characterization of the phosphorylation sites. The labeled glycopeptides were purified by gel permeation chromatography and rpHPLC. Sequence analysis of the three fragments listed in FIG. 28 indicated that Asn-82, Asn-136, and Asn-176 are glycosylated. Over 95% of the label was found in peptides E(77-91) and E(134-139). Peptide T(174-180) contained less than 5% of the total incorporated [$^{32}$P]-label.

S-pyridylethylated rTGF-β1 precursor was cleaved with CNBr at methionine residues. Gel permeation chromatography of the CNBr fragments on a Bio-Sil TSK-250 column resolved [$^{32}$P]-M(134-253), and [$^{32}$ P]-M(39-113). A representative chromatogram is shown in FIG. 29.

M(39-113) was further subfragmented with S. aureus V8 protease. The enzyme digest was acidified and the peptides separated by rpHPLC. A representative chromatogram is shown in FIG. 30. The complete sequences of [$^{32}$P]-E(76-91) and [$^{32}$P]-E(76-94) were determined. Both peptides contain a carboxyl-terminal glutamic acid, consistent with the specificity of the protease. Both peptides contained on unidentified residue at position 82 (Table IX). The DNA sequence predicts an asparagine residue at position 82 of the TGF-β1 precursor translation product, a potential site for N-linked glycosylation. The expected yield of PTH-Asn at cycle 7 would have allowed identification of an unmodified asparagine. The yield of PTH-Asn at position 82 was approximately 0.5% of that expected based on the yields of the adjacent residues. The lower yield of PTH-Asn-82 may be due to the decreased solubility of the modified thiazolinone derivative in the extracting solvent, butyl chloride, relative to other thiazolinone amino acids. Acid hydrolysis and subsequent 2-dimensional electrophoresis of [$^{32}$P]-E (76-91) detected mannose-6-[$^{32}$P)-phosphate FIG. 31.

M(134-253) was further subfragmented with S. aureus V8 protease, yielding two major [$^{32}$P]-labeled peptides, as shown in FIG. 31A. The sequences of the listed peptides were determined, both containing a carboxyl-terminal glutamic acid, consistent with the specificity of the protease. Peptide [32 P]-E(134-139) contained one unidentified residue at position 136 (Table IX). The yield of the predicted PTH-Asn was approximately 2% of that expected, based on the yields of the adjacent residues, and was thus assumed to be glycosylated Asn. Acid hydrolysis and subsequent 2-dimensional electrophoresis of [$^{32}$P]-E(134-139) detected mannose-6-[$^{32}$P]-phosphate (FIG. 32).

Peak A (FIG. 31A), containing E(170-194), was pooled, dried, and subfragmented with trypsin. The digest was acidified and the peptides separated by rpHPLC. A representative chromatogram is shown in FIG. 31B. The sequence of T(174-180) was determined (Table IX). Peptide T(174-180) contained one unidentified residue at position 176. The yield of the predicted PTH-Asn was approximately 1% of the expected, based on the yield of the adjacent residue Asn-177 suggesting glycosylation of Asn-176. The chromatographic heterogeneity of T(174-180) is evident. This peptide contained less than 5% of the total [32P]-incorporated into the precursor protein. Acid hydrolysis and subsequent 2-dimensional electrophoresis detected mannose-6-[$^{32}$P]-phosphate (not shown).

Peak B (FIG. 31A) was dried and redigested with S. aureus V8 protease and subsequently with trypsin and the peptides were separated by rpHPLC. Similar peptide patterns were obtained as shown in FIG. 31A AND FIG. 31B, suggesting incomplete cleavage of M(134-253) with V8 protease.

Thin layer electrophoretic analysis of acid hydrolysates of total precursor proteins (a and b) as well as purified glycopeptides showed that [$^{32}$P]-phosphate was incorporated into mannose-6-phosphate; no [$^{32}$P]-phosphate was incorporated into Ser, Thr, Tyr (FIG. 32A–C). Comigration of peptide-incorporated [$^{32}$P] -label and standards of mannose-6-phosphate was observed upon electrophoresis in buffers at pH 1.9, pH 3.5 and pH 8.9, and in two different chromatography buffers (FIG. 32D and data not shown). Acid hydrolysis may also generate mannose-6-phosphate from proteins modified with glycosylphosphatidylinositol (Lon and Saltiel, 1988, Science 239:268–295), but this has only been found at the carboxyterminus of proteins and is therefore unlikely to account for mannose-6-phosphate in the rTGF-β1 precursor.

TABLE IX

AMINO ACID SEQUENCE DATA FOR GLYCOPEPTIDES FROM S-PYRIDYLETHYLATED rTGF-β1 PRECURSOR

| Position | Residue | Peptide (cycle) yield (pmol) | Position | Residue | Peptide (cycle) yield(pmol) |
|---|---|---|---|---|---|
| E (76–91) | | | E(134–139) | | |
| 76 | Ala | (1) 87.0 | 134 | Phe | (1) 99.4 |
| 77 | Val | (2) 91.3 | 135 | Phe | (2) 98.3 |
| 78 | Leu | (3) 111.2 | 136 | Asn | (3) 2.1 |
| 79 | Ala | (4) 100.5 | 137 | Thr | (4) 55.5 |
| 80 | Leu | (5) 75.7 | 138 | Ser | (5) 28.1 |
| 81 | Tyr | (6) 71.4 | 139 | Glu | (6) 52.8 |
| 82 | Asn | (7) 0.2 | T(174-180) | | |
| 83 | Ser | (8) 28.5 | 174 | Tyr | (1) 10.0 |
| 84 | Thr | (9) 42.5 | 175 | Ser | (2) 3.8 |
| 85 | Arg | (10) 43.6 | 176 | Asn | (3) 0.1 |
| 86 | Asp | (11) 45.8 | 177 | Asn | (4) 8.5 |
| 87 | Arg | (12) 47.6 | 178 | Ser | (5) 3.3 |
| 88 | Val | (13) 39.0 | 179 | Trp | (6) 5.1 |
| 89 | Ala | (14) 37.9 | 180 | Arg | (7) 1.7 |
| 90 | Gly | (15) 23.3 | | | |
| 91 | Glu | (16) 10.7 | | | |

Experiments designed to determine whether the TGF-β1 precursor is capable of binding to the mannose 6-phosphate receptor were also conducted. $^{125}$I-labeled TGF-β1 precursor was incubated with purified mannose 6-phosphate receptor. The results presented in FIG. 34 demonstrate that the precursor can bind to purified receptor since approximately 30 times as much radioligand bound to receptor as in control incubations without receptor. This binding was specific since it was almost completely inhibited (90%) by either 100 nM TGF-β1 precursor 50 μM mannose 6-phosphate.

10. EXAMPLE: EXPRESSION OF TGF-β1 VARIANTS IN COS CELLS

Site directed mutagenesis was used to alter the primary structure of TGF-β1 at three cysteine residues located in the pro region of the TGF-β1 precursor by changing the coding sequences for cysteine residues at amino acid positions 33, 223 and 225 (FIG. 1) to the coding sequences for serine. Mutant constructs were used to transfect COS cells and recombinant TGF-β1 variant proteins produced by the transfectants were analyzed. The results indicate that CYS-33 may be involved in regulating the processing of mature TGF-β1. The CYS-33 modification yields a precursor which ultimately results in the production of higher levels of mature TGF-β1.

10.1. MATERIALS AND METHODS
10.1.1. CHARACTERIZATION OF CNBr PEPTIDE M(134-253)$^2$ rTGF-β1 precursor synthesized by CHO cells was purified by gel permeation chromatography, cleaved with CNBr and the peptides purified as described (Section 8., et seq. herein). Cysteine-containing peptides were detected after reduction with tributylphosphine and coupling with ammonium 7-fluorobenzo-2-oxo-1,3-diazole-4-sulfonate (Sueyoshi et al., 1985, J. Biochem. (Tokyo) 97:1811–1813) and purified to homogeneity by reversed-phase HPLC on a μBondapak C$_{18}$ column (Waters Associates Inc., Milford, Mass.).

Peptides were separated on 15% SDS-polyacrylamide gels and stained with Coomassie brilliant blue R-250. Disulfide-linked peptides were analyzed with an Applied Biosystems 475A sequencer. Phenylthiohydantoin-amino acid derivatives were evaluated on an Applied Biosystems 120A PTH-analyzer as described (Gentry et al., 1988, Mol. Cell. Biol. 8:4162–4168).

10.1.2. CONSTRUCTION OF EXPRESSION VECTORS CODING FOR

TGF-β1 VARIANTS AND DNA TRANSFECTIONS pTGF-β-2 (Sharples et al., 1987, DNA 6:239–244) was digested with PstI and EcoRI and the 1400 bp fragment containing the entire TGF-β1 coding region ligated to plasmid pSP64 which had been previously digested with PstI and EcoRI. The construct was used to transform *E. coli* HB101 and plasmid pSP64/TGF-β1 was isolated. The PstI-EcoRI fragment of TGF-β1 cDNA was excised from pSP64/TGF-β1 and inserted into M13mp18, placing a HindIII restriction site 5' to the PstI site. Single-stranded DNA, containing the Mp18 strand and the non-coding strand of TGF-β1, was isolated and used as a template for site-directed mutagenesis. CYS-33, CYS-223, and CYS-225 were individually changed to SER codons using a commercially available oligonucleotide-directed in vitro mitogenesis system (Amersham).

The following oligonucleotides were used to construct the mutants:

5'-ACTATCCACC<u>AGC</u>AAGACTAT-3' for SER-33;
5'-TAGCGCCCAC<u>AGC</u>TCCTGTGA-3' for SER-223;
5'-CACTGCTCC<u>TCT</u>GACAGCAAA-3' for SER-225; and
5'-TAGCGCCCAC<u>AGC</u>TCC<u>TCT</u>GACAGCAAA-3' for SER-223/225.

In each case, a nucleotide change accomplished the CYS to SER codon change. Five to ten plaques were screened for the desired mutation by single track sequencing using the final mutant characterized by further sequencing using the dideoxy chain-termination method (Sanger et al., 1977, Proc. Natl. Acad. Sci., U.S.A. 84:8573–8577).

Replicative forms containing the mutant cDNAs were isolated, digested with EcoRI, repaired to blunt ends, and digested with HindIII. The resulting cDNA fragments were ligated into pπH3M (Aruffo and Seed, 1987, Proc. Natl. Acad. Sci. U.S.A. 84:8573–8577; Seed and Aruffo, 1986, Proc. Natl. Acad. Sci. U.S.A. 84:3365–3369) at HindIII and XhoI (blunt) sites to construct plasmids pπH3M/β1 SER-33 (encoding pre-pro-TGF-β1$^{S33}$), pπH3M/β1 SER-223 (encoding pre-pro-TGF-β1$^{S223}$), pπH3M/β1 SER-225 (encoding pre-pro-TGF-β1$^{S225}$) and pπH3M/β1 SER-223/225 (encoding pre-pro-TGF-β1$^{S223/225}$). COS cells were transfected with these plasmids as well as plasmid pπH3M/β1 (encoding wild-type TGF-β1) as described (Aruffo and Seed, 1987, Proc. 1. Acad. Sci. U.S.A. 84:8573–8577; Seed and Aruffo, 1986, Proc. Natl. Acad. Sci. U.S.A. 84:3365–3369) with the following modifications. Transfection was performed in 100 mm dishes with 10$^6$ cells using 5 ml transfection material for 2.5 hours at 37° C. At 48 hours post-transfection, cells were placed in serum-free media and 72 hours later conditioned media was collected, dialyzed against three changes of 0.2M acetic acid and analyzed by immunoblotting with mature- and precursor-specific peptide antibodies as described in Section 7.1.7., supra. Bioactivity was determined by the growth inhibition assay described in Section 7.1.6., supra.

10.2. RESULTS
10.2.1. ANALYSIS OF PROTEINS ENCODED BY MUTANT TGF-β1 CODING SEQUENCES

The bioactivity detected in dialyzed serum-free media conditioned by COS transfectants is summarized in Table X, below. Cells transfected with plasmid pπH3M/β1 SER-33, encoding a TGF-β1 variant precursor, secrete between three and five times more biologically active protein than do cells transfected with plasmid pπH3M/β1, encoding wild-type TGF-β1. In contrast, cells transfected with plasmids encoding the SER-223 and SER-225 variants did not secrete higher levels of bioactive protein in comparison to cells transfected with the wild-type construct.

TABLE X

BIOACTIVITY OF MEDIA CONDITIONED BY COS CELLS TRANSFECTED WITH VARIOUS TGF-β1 ENCODING PLASMIDS

| | | BIO-ACTIVITY (ng/ml) | |
|---|---|---|---|
| COS Transfectant | Plasmid | A | B |
| COS-TGF-β1 | pπH3M/β1 | 39 | 50 |
| COS-TGF-β1/SER-33 | pπH3M/β1 SER-33 | 209 | 174 |
| COS-TGF-β1/SER-223 | pπH3M/β1 SER-223 | 39 | 37 |
| COS-TGF-β1/SER-225 | pπH3M/β1 SER 225 | 26 | 28 |

COS cells were transfected with plasmids encoding wild type TGF-β1 (pπH3M/β1); TGF-β1 with CYS-33 replaced by SER (pπH3M/β1 SER-33); TGF-β1 with CYS-223 replaced by SER (pπH3M/β1 SER-223); or TGF-β1 with CYS-225 replaced by SER (pπH3M/β1 SER 225). The data show the results of two independent growth inhibition assays (Section 7.1.6, supra).

Immunoblot analysis was performed using anti-TGF-β1$_{369-381}$+anti-TGF-β1$_{81-94}$ as described in Section 7.1.8., supra, to detect TGF-β1 related proteins. The results are presented in FIGS. 33A–G. Under reducing conditions (FIG. 33D), the mutant proteins appear to be identical to the wild type protein. Antibodies detected the 12 kDa mature monomer ('c' in FIG. 33B) as well as 44 to 56 kDa and 30 to 42 kDa precursor forms ('a' and 'b' in FIG. 33B). In addition, the immunoblot shown in FIG. 33D indicates that the absolute amount of secreted TGF-β1 proteins was not significantly affected by the mutations.

Differences between mutant and wild-type TGF-β1 proteins were apparent when examined under non-reducing conditions (FIG. 33E). Mature TGF-β1 dimer (24 kDa) was present in all transfectant supernatants. However, cells transfected with pπH3M/β1 SER-33 yielded increased levels of the 24 kDa dimer compared to wild-type transfectants (FIG. 33E, lanes 3 and 4), while pπH3M/β1 SER-33, pπH3M/β1 SER-225, and pπH3M/β1 SER-223/225 transfectants produced near wild type levels. This increase in 24 kDa dimer does not appear to result from increased protein synthesis/secretion, or increased cleavage of mature TGF-β1 from pro-TGF-β1, since immunoblotting under reducing conditions indicated that pπH3M/β1 and pπH3M/β1 SER-33 transfectants secreted approximately equal amounts of mature and precursor forms (FIG. 33D).

In addition, the TGF-β1$^{S33}$ proteins did not form the 90 to 110 kDa precursor complex as did wild-type proteins (FIG. 33E). Instead, a 130 to 150 kDa and 75 to 85 kDa species were seen (FIG. 33E, lane 4). As shown in FIG. 33F and FIG. 33G, the TGF-β1$^{S33}$ 130 to 150 kDa proteins were recognized by both pro region- and mature-specific antibodies, most likely representing dimeric pro-TGF-β1$^{S33}$. The 75 to 85 kDa polypeptide was only detected by pro region-specific antibody (FIG. 33G, lane 4), probably representing a dimer of the pro region of the TGF-β1$^{S33}$ precursor.

In contrast, mutant proteins encoded by pπH3M/β1 SER-223 and pπH3M/β1SER-225 formed 90 to 110 kDa precursor complexes (lanes 5 and 6 in FIG. 33E, FIG. 33F and FIG. 33G), though some monomeric precursor forms were also present. Antibodies specific for the pro region of the TGF-β1 precursor detected 44 to 56 kDa and 30 to 42 kDa proteins (FIG. 33G, lanes 5 and 6), while antibodies specific for mature sequences detected only the 44 to 56 kDa species (FIG. 33F, lanes 5 and 6). Cells transfected with pπH3M/β1 SER-223/225 yielded only monomeric precursor forms (lane 7 in FIG. 33E, FIG. 33F and FIG. 33G), yet mature TGF-β1 was still proteolytically cleaved from pro-TGF-β1$^{S223/225}$ and formed the 24 kDa dimer.

Applicants' discovery that eliminating the CYS-33 residue from the TGF-β1 precursor ultimately improves the yield of secreted TGF-β1, perhaps by preventing a significant population of nascent TGF-β1 monomers from being intracellularly confined within high molecular weight precursor complexes, may constitute an improved method for producing recombinant bioactive TGF-β1. Moreover, such a method may have utility in increasing the production of recombinant bioactive TGF-β2, TGF-β3, other forms of TGF-β, TGF-β analogs, or other related proteins.

10.2.2. TGF-β1 PRECURSOR RESIDUES CYS-223 AND CYS-225 FORM INTERCHAIN DISULFIDE BONDS

Purified rTGF-β1 precursor was cleaved at methionine residues with CNBr and the resulting peptides were purified by gel permeation chromatography. CYS-containing peptides were detected as described (Sueyoshi et al., 1985, J. Biochem. (Tokyo) 97:1811–1813) and purified to homogeneity by reversed-phase HPLC. Edman degradation data located the positions of the CNBr peptides in the sequence of the TGF-β1 precursor. Peptide M(134-253)$_2$ contained 2 half-cystine residues (determined by amino acid analysis), but lacked free sulfhydryl groups (determined with a fluorescent thiol specific reagent under non-reducing conditions). Disulfide bridges in M(134-253)$_2$ were assigned by demonstrating the dimeric character of this peptide. As shown in FIG. 33A, the size of M(134-253)$_2$ was estimated at 41 kDa under nonreducing conditions; under reducing conditions, M(134-253) had a molecular weight of 24 kDa. The change in molecular weight of M(134-253)$_2$ following reduction identifies two intersubunit disulfide bonds linking identical chains, consistent with a single amino acid sequence for peptide M(134-253)$_2$ and the determination of 2 half-cystine residues by amino acid analysis. The observed heterogeneity of M(134-253)$_2$ on SDS-polyacrylamide gel electrophoresis (FIG. 33A) may reflect glycosylation at Asn-136 and Asn-176.

10.2.3. VARIANT TGF-β1 PRECURSORS GENERATE BIOLOGICALLY ACTIVE TGF-β1

Biological activity corresponded well with the amount of 24 kDa mature TGF-β1 detected by immunoblotting (FIG. 33E and FIG. 33F). Following acid-activation, supernatants from cells transfected with plasmids pπH3M/β1 SER-223, pπH3M/β1 SER-225 and pπH3M/β1 SER-223/225 yielded near wild-type levels of inhibitory activity (TABLE XI). In contrast, pπH3M/β1 SER-23 transfectants yielded approximately 3- to 5-fold more activity than pπH3M/β1 transfectants. These observations were consistent among separately performed transfections, with pπH3M/β1 SER-33 transfected COS cells always generating 3- to 5-fold more inhibitory activity than cells transfected with wild-type plasmid pπH3M/β1.

TABLE XI

AMOUNT OF BIOACTIVE TGF-β1 SECRETED BY COS CELL TRANSFECTANTS[1]

| PLASMID | ng/ml +ACID | –ACID |
|---|---|---|
| pπH3M/β1 | 90.3 | 4.7 |
| pπH3M/β1 SER-33 | 304.8 | 12.5 |
| pπH3M/β1 SER-223 | 98.4 | 20.3 |
| pπH3M/β1 SER-225 | 77.9 | 11.2 |
| pπH3M/β1 SER-223/225 | 87.9 | 65.3 |

[1]COS cells were transfected with plasmids encoding TGF-β1 and variants; 48 hr. post-transfection, supernatants were replaced with serum-free media; 72 hr. later, conditioned media was collected and assayed directly (–ACID) or following dialysis vs. 0.2M acetic acid (+ACID) for growth inhibition of CCL64 cells.

10.2.4. TGF-β1$^{S223/225}$ VARIANT YIELDS BIOLOGICALLY ACTIVE TGF-β1 WITHOUT PRIOR ACIDIFICATION rTGF-β1 synthesized by COS cells is secreted in a latent form (TABLE XI). Similarly, TGF-β1 is released by platelets as a latent high molecular weight complex (Miyazono et al., 1988, J. Biol. Chem. 263:6407–6415; Wakefield et al., 1988, J. Biol. Chem. 263:7646–7654).

Activation of rTGF-β1 can be achieved by acidification. Both TGF-β1 and TGF-β$^{S33}$ were ≧90% biologically inactive prior to acidification, while TGF-β1 S223 and TGF-β1 S225 were ≧80% inactive. However, TGF-β1$^{223/225}$ was at least 70% active without acid treatment and, in separate experiments, levels of activity before and after acidification were equivalent, suggesting that the pro region of the TGF-β1 precursor is necessary for rTGF-β1 latency. Platelet derived TGF-β1 was recently shown to be non-covalently associated with a complex involving the dimeric precursor pro region and another protein (Miyazono et al., 1988, J. Biol. Chem. 263:6707–6415; Wakefield et al., 1988, J. Biol. Chem. 263:7646–7654). The TGF-β1$^{S223/225}$ precursor exists only as a monomer (lane 7 in FIG. 33E, FIG. 33F and FIG. 33G); thus, conformational changes resulting from the substitution of both CYS-223 and CYS-225 may not allow interactions between mature TGF-β1 and its precursor which result in latency.

11. EXAMPLE: INTERACTION OF TGF-β1 PRECURSOR WITH INSULIN-LIKE GROWTH FACTOR/MANNOSE 6-PHOSPHATE RECEPTOR

The experiments described below demonstrate that the TGF-β1 precursor binds to the insulin-like growth factor (IGF)-II/mannose G-phosphate (man6P) receptor. These studies were supported in part by National Institutes of Health Grant DK34926 and a grant from the Republic Foundation of Science, SR Srbia, Yugoslavia.

11.1. MATERIALS AND METHODS
11.1.1. MATERIALS

Recombinant IGF-II was a gift of Dr. M. Smith (Eli Lilly Co.) and was iodinated (160 Ci/g) as described (Steele-Perkins et al., 1988, J. Biol. Chem. 263:11486–30 11492). Recombinant TGF-β1 precursor was prepared and iodinated (190 Ci/g) as described in Section 8.3 and Section 9.1.3., supra, respectively. Purified latent TGF-β1 was isolated from platelets (Miyazono et al., 1988, J. Biol. Chem. 263:6407–6415) and desalted on a Superose 6 column.

The IGF-II/man6P receptor and polyclonal antibodies to this protein were as previously described (Hari et al., 1987, EMBO J. 6:3367–3371). CHO cells overexpressing the human IGF-II/man6P receptor were produced as described previously for the human IGF-I receptor (Steele-Perkins et al., 1988, J. Biol. Chem. 263:11486–11492). Monoclonal antibodies to the IGF-II/man6P receptor (Braukle et al., 1987, J. Cell. Biol. 104:1735–1742) were a gift of Dr. A. Hasilik (Universität Munster). A polyclonal anti-peptide antibody (to residues 81–94) to the precursor sequence of TGF-β1 was prepared as described in Section 7.1.8., supra.
11.1.2. RECEPTOR BINDING AND INTERNALIZATION STUDIES The epididymal fat pads from male Sprague-Dawley rats (180–220 g) were excised, minced, and collagenase-digested as described (Rodberg, 1964, J. Biol. Chem. 239:375–380). The isolated adipocytes were pre-incubated with or without 1 μM insulin for 10 min at 37° C. in 0.7 ml Krebs-Ringer buffer (107 mM NaCl, 5 mM KCl, 3 mM CaCl$_2$, 1 mM MgSO$_4$, 7 mM NaHCO$_3$, 10 mM glucose, and 20 mM Hepes, pH 7.8) with 3% bovine serum albumin. The indicated labeled ligand was added and the incubations continued for 45 minutes at 37°. The cells were separated from the media by centrifugation through silicon oil and the radioactivity in the cell layer counted.

Binding and internalization studies with transfected and control CHO cells were performed in 24-well culture plates. Confluent cells were washed and incubated for 5 hours at 4° C. with the labeled ligand in 0.3 ml of binding buffer (100 mM Hepes, pH 7.6, 120 mM NaCl, 1.2 mM MgSO$_4$, 15 mM sodium acetate, 5 mM glucose). Cells were then washed twice, lysed with 0.1% sodium docecyl sulfate and counted. For the internalization studies, labeled ligand was added to the cells in serum-free Ham's F-12 medium containing 0.1% bovine serum albumin and 20 mM Hepes, pH 7.6. After the indicated periods of time at 37° C., the cells were put on ice and washed with pre-cooled Hepes buffered saline containing 0.3 mM CaCl$_2$. To determine the acid resistant fraction (i.e. the internalized ligand), cells were incubated for 5 minutes at 4° C. with 0.2M CH$_3$COOH, 0.5M NaCl, pH 3.0 (Haigler et al., 1980, J. Biol. Chem. 255:1239–1240.). The cells were then washed, solubilized, and counted as above.

Binding studies were also performed with isolated IGF-II/man6P receptor (Purchio et al., 1988, J. Biol. Chem. 263:14211–14215). For these studies, the purified receptor was absorbed to microtiter wells coated with 100 nM of a monoclonal antibody (2C2) specific for the human IGF-II/man6P receptor (Braukle et al., 1987, J. Cell. Biol. 104:1735–1742). The labeled recombinant TGF-β1 precursor was then incubated with the receptor in the presence of the indicated concentrations of competing ligand for 3 hours at 4° C. The wells were then washed, cut out, and counted.
11.1.3. WESTERN BLOT ANALYSIS Recombinant and platelet purified TGF-β1 precursor were electrophoresed on reduced, sodium dodecyl sulfate, polyacrylamide (12.5%) gels. The samples were transferred to nitrocellulose filters (Schleicher and Schuell) which were then incubated in a blocking solution (3% bovine serum albumin and 0.1% Triton X-100 in Tris-buffered saline, pH 7.5) for 30 minutes at 24° C. The filters were then incubated overnight at 4° C. with either: 1) a rabbit anti-peptide antibody to the precursor sequence of TGF-β1 (diluted 1:100) (10); or 2) purified IGF-II/man6P receptor, followed by a polyclonal antibody to this receptor (Hari et al., 1987, EMBO J. 6:3367–3371). After washing four times, the filters were incubated with anti-rabbit IgG conjugated to alkaline phosphatase (1:5000, Promega) for 1 h at 4° C., washed, and then developed with the phosphatase substrate (Promega).

11.2. RESULTS
11.2.1. RECOMBINANT TGF-β1 PRECURSOR BINDS TO IGF-II/MAN6P RECEPTORS ON ADIPOCYTES AND IS INTERNALIZED

Binding of I-IGF-II and recombinant TGF-β1 precursor to primary rat adipocytes was measured with and without insulin pretreatment. As previously reported (Oka et al., 1985, J. Biol. Chem. 260:9435–9442; Appell et al., 1988, J. Biol. Chem. 263:10824–10829), insulin caused a 2- to 3-fold increase (average=2.4±0.3, n=4) in specific binding of IGF-II to the adipocytes (FIG. 35A). As shown in FIG. 35B, insulin caused a similar increase in the binding of recombinant TGF-β1 precursor to the adipocytes (average= 2.7±0.3, n=4). Binding of TGF-β1 precursor to the control and insulin-treated adipocytes was inhibited 65% and 81%, respectively, by 3 mM man6P (FIG. 35B). These results indicate that the recombinant TGF-β1 precursor was binding to the IGF-II/man6P receptor on adipocytes.

Additional binding studies were then performed with a line of CHO cells which were transfected with a cDNA encoding the IGF-II/man6P receptor (Morgan et al., 1987, Nature 329:301–307) and selected for overexpression of the receptor protein. These transfected cells specifically bound about 10 times more IGF-II (FIG. 36A) as well as about 15 times more recombinant TGF-β1 precursor than the parental CHO cells; TGF-β1 precursor binding was substantially inhibited by man6P (FIG. 36B). The inhibition by man6P was dose-dependent and half-maximal inhibition was observed at 10 μM (FIG. 37A). Mannose 1-phosphate was at least 1,000 times less effective at inhibiting binding of the TGF-β1 precursor (FIG. 37A). The binding of the precursor to the transfected cells was also inhibited by unlabeled TGF-β1 precursor but not by mature TGF-β1 (FIG. 37B). One hundred nM IGF-II inhibited the binding of precursor TGF-β1 by 34%.

The bound TGF-β1 precursor was also tested for its ability to be internalized in the transfected cells. After various periods of time at 37° C., the cell surface TGF-β1 precursor was removed by an acid wash of the cells and the acid-resistant (i.e. internalized) (Hagler et al., 1980, J. Biol. Chem. 255:1239–1241) TGF-β1 precursor measured. After 15 min, >75% of the specifically bound TGF-β1 precursor was found to be in an acid-resistant compartment (FIG. 38). A further increase in total and internalized counts was observed after 20 minutes, and appears to result from a non-specific binding route since man6P did not block the increase (FIG. 38).

11.2.2. PRESENCE OF MANNOSE 6-PHOSPHATE ON LATENT TGF-β1

To determine whether latent TGF-β1 isolated from platelets also contains man6P, highly purified platelet TGF-β1 precursor was tested for its ability to inhibit the binding of labeled recombinant TGF-β1 precursor to isolated IGF-II/man6P receptor. The latent platelet TGFβ1 complex was found to be a potent inhibitor of this binding, with half-maximal inhibition occurring at approximately 0.2 nM (FIG. 39).

To further examine the platelet TGF-β1 complex for the presence of man6P, this material was electrophoresed on a reduced polyacrylamide SDS gel, transferred to a nitrocellulose membrane, and sequentially incubated with purified IGF-II/man6P receptor, rabbit antibodies to the receptor, alkaline phosphate-conjugated anti-rabbit Ig and a histochemical stain for alkaline phosphatase. Although this technique could detect the man6P on the uncleaved recombinant TGF-β1 precursor (FIGS. 40A and 40B, band a) and precursor remnant (FIGS. 40A and 40B, band b), no band of the appropriate molecular weight was detected with the platelet TGF-β1. In control experiments, an antibody specific for the sequence of the TGF-β1 precursor could detect the platelet TGF-β1 precursor remnant (FIGS. 40A and 40B, band c).

12. EXAMPLE ANALYSIS OF FUNCTIONAL ROLE OF CARBOHYDRATE ON TGF-β1 PRECURSOR

The studies below examine the importance of the carbohydrate epitopes of pre-pro-TGF-β1 in the processing of mature TGF-β1. The results demonstrate that oligosaccharide addition and remodeling play an essential role in the process of TGF-β1 secretion but play no role in the specific proteolysis of pre-pro-TGF-β1 and, furthermore, that proteolytic processing of the TGF-β1 precursor occurs intracellularly in acidic vesicles.

12.1. MATERIALS AND METHODS
12.1.1. MATERIALS

The glycosylation inhibitors swainsonine (SW), tunicamycin (TU), castanospermine (CA), 1-deoxymannojirimycin (dMM), and 1-deoxynojirimycin (dN) as well as the glycosylational trimming enzymes endoglycosidase H (endo H) and neuraminidase were purchased from Boehringer-Mannheim Biochemicals, Indianapolis, Ind. N-glycanase was obtained through Genzyme, Boston, Mass. Chloroquine diphosphate, monensin and diethylaminoethyl-dextran (DEAE-dextran; 500,000 MW) were purchased from Sigma Chemical Company, St. Louis, Mo. Nuserum was acquired from Collaborative Research, Lexington, Mass. All other cell culture reagents were purchased from GIBCO Laboratories, Grand Island, N.Y. [35-S]-L-Cysteine and [35-S]-L-Methionine were procured from NEN Research Products, Boston, Mass. and possessed specific activities >600 and >800 Ci/mM, respectively. [32-P]-orthophosphate (carrier free) was obtained from ICN Biomedicals, Costa Mesa, Calif. Restriction and other DNA modifying enzymes were obtained from Bethesda Research Laboratories, Bethesda, Md.

12.1.2. CELL CULTURE

CHO-TGF-β3-2000 cells (clone 17) were grown and passaged as described in Section 7.1.1., supra. Cos-1 cells (ATCC CRL 1650) were grown in Dulbeco modified eagles medium (DMEM) supplemented with 10% fetal bovine serum, 100 U/ml penicillin and 100 μg/ml streptomycin and passaged by trypsinization.

12.1.3. METABOLIC LABELING AND ANALYSIS OF SECRETED TGF-β1

TGF-β3-2000 cells were grown to confluency on 35 mm dishes containing 2 ml of complete medium. The medium was replaced with medium lacking methionine, cysteine and serum and incubated for 1 h. The cells were then labeled for 0.5 h with [35-S]-methionine and [35-S]-cysteine, each at 100 μCi/ml. After labeling, the cells were washed three times in Hanks balanced salt solution and chased in complete, serum free DMEM. Glycosylational inhibitors, weak bases or ionophores were present in the tissue culture medium throughout the above incubations. Supernatants were directly analyzed by SDS-PAGE after boiling in SDS-PAGE sample preparation buffer. Gradient gels from 7.5–20% acrylamide were utilized.

For [32-P]-phosphate labeling, cells were incubated in 35 mm dishes containing 1 ml of phosphate and serum free DMEM for 1 h. The cells were labeled with 1 mCi per ml of [32-P]-orthophosphate for 6 h. The cell free medium was collected and excess [32-P]-phosphate removed by desalting on a 10-ml column of Sephadex G-25 equilibrated with 50 mM ammonium bicarbonate. The first three 0.75 ml fractions containing radioactivity were pooled and lyophilized, and the lyophilized pellet dissolved in 10 μl of sample preparation buffer and 10 μl analyzed by SDS-PAGE and autoradiography.

12.1.4. QUANTITATION OF TGF-β1 BY SDS-PAGE

The amount of TGF-β1 in culture supernatants was measured from SDS-polyacrylamide gels by densitometry after the gels were fluorographed. In most cases, the ratio of mature TGF-β1 to the amount of precursor forms was invariant. Thus, the amount of mature, 12 kDal TGF-β1 observed was utilized as a measure of the total growth factor secreted.

To measure variations in the amount of processing, the total level of TGF-β1 secreted was determined after densitometry by summing all three forms of recombinant growth factor and normalizing the level of secretion between the various treated cells. The relative amount of mature, 12 kDal TGF-β1 was then calculated to indicate the level of proteolytic processing.

12.1.5. DIGESTION WITH GLYCOSYLATIONAL TRIMMING ENZYMES

Conditioned culture medium labeled with [35-S]-cysteine and -methionine were treated with the glycosylational trimming enzymes. Culture medium (23 μl) was treated with 5 mU of endo H or 25 mU of neuraminidase at 37° C. overnight. Digestion with N-glycanase was performed at 30° C. overnight using 1.25 U of enzyme. In all cases, the total reaction volume was 35 μl . Reaction buffers for endo H and neuraminidase consisted of 25 mM Tris-HCl, 0.2% SDS (w/v) at pH 5.7 and 50 mM sodium acetate, 2 mM calcium chloride, and 0.2 mM EDTA at pH 4.6, respectively. N-glycanase digestions were performed in a final buffer composition of 10 mM EDTA, 0.2% SDS (w/v), 0.1M 2-mercaptoethanol, and 1% nonidet-P40 (v/v) at pH 7.5. After digestion, the samples were mixed with an equal volume of 2X-SDS sample preparation buffer and a 16 μl aliquot analyzed by SDS-PAGE.

12.1.6. PREPARATION OF SacII DELETION MUTANT OF TGF-β1 AND INSERTION INTO CDM8 VECTOR

TGF-β1 cDNA subcloned into pUC19 was utilized for deletion mutagenesis. Plasmid DNA was digested with SacII and re-ligated affording removal of 480 nucleotides of the coding region of TGF-β1 cDNA and providing an in frame deletion. The resulting plasmid was digested with EcoRI repaired to blunt ends with Klenow fragment of DNA polymerase I and subsequently digested with HindIII. This fragment was inserted into the CDM8 expression plasmid.

The CDM8 expression plasmid DNA (Seed, 1987, Nature 329:840–842) was digested with NotI and repaired to blunt end with Klenow enzyme. The DNA was subsequently digested with HindIII and isolated from an agarose gel using Geneclean. The HindIII-EcoRI(blunt) fragment of wild type TGF-β1 cDNA and of the SacII deletion mutant were then ligated into the HindIII-NotI (blunt) CDM8 vector. CsCl-purified DNA was used for expression studies.

12.1.7. TRANSIENT EXPRESSION IN COS CELLS

Transient expression in Cos-1 cells was accomplished by a DEAE-dextran-chloroquine transfection protocol as described (Cullen, 1987, Meth. Enzymol. 152:684–704). Briefly, semi-confluent cultures of Cos-1 cells grown on 35 mm dishes were incubated in DMEM containing 10% Nuserum 1–2 h prior to addition of DNA. The transfection cocktail was prepared by slowly adding CsCl-purified DNA to a sterile solution of 10 mg/ml DEAE-dextran to give a final concentration of 0.2 mg/ml of DNA. The DEAE-dextran/DNA mix (100 μl) was then added to the cells at a final concentration of 10 μg/ml of DNA. Chloroquine at a final concentration of 100 μg/ml was then added and allowed to incubate with the cells at 37° C. for 3 h. The DNA/DEAE-dextran/chloroquine containing medium was then removed and the cells treated with 2 ml of 10% dimethyl sulfoxide (v/v) in phosphate buffered saline. After 2 minutes at room temperature, cells were washed twice in phosphate buffered saline and grown in complete DMEM for 48 h.

For immunoblot analysis of the expressed TGF-β1, serum-free culture medium was then added to the cells, collected for 48 h and dialyzed against 0.4% acetic acid. The dialyzed medium was lyophilized, dissolved in 30 μl of sample preparation buffer, and 5 μl analyzed by immunoblot analysis. The transfected cells were also analyzed by immunoblotting. Following collection of the serum free medium, the cells were harvested by scraping and one volume of SDS-sample preparation buffer added per volume of packed cells. After boiling for 5 minutes, 2 μl of cellular lysate was analyzed by immunoblotting.

12.2. RESULTS

12.2.1. TUNICAMYCIN INHIBITS SECRETION OF RECOMBINANT TGF-β1 FROM TRANSFECTED CHO CELLS

In preliminary experiments designed to address the functional role of glycosylational processing for transport and secretion of pre-pro-TGF-β1, transfected CHO cells were treated with tunicamycin (TU), a nucleoside antibiotic which prevents oligosaccharide addition of the nascent polypeptide chain (Tacz and Lampen, 1975, Biochem. Biophys. Res. Commun. 65:248–257), and analyzed the condition medium and cells for expressed TGF-β1. FIG. 41 shows the results which were obtained using immunoblotting to detect TGF-β1 proteins in the culture medium or cells. Medium from control cells fractionated on SDS gels under reducing conditions showed the existence of three forms of recombinant TGF-β1 (See Section 7, et seq.). The 44–56 Kdal polypeptide represents pro-TGF-β1 ("a" in FIG. 41), the 30–42 Kdal protein corresponds to the pro region of the precursor ("b" in FIG. 41), and the 12 kDal form represents mature, properly processed TGF-β1 ("c" in FIG. 41). CHO cells treated with tunicamycin over a period of 24 h, however, did not appear to release detectable levels of immunoreactive TGF-β1.

The major intracellular form of TGF-β1 in control cells appeared to migrate at a position corresponding to partially glycosylated growth factor. Very low levels of processed TGF-β1 polypeptides were also detectable within the cells only when increased amounts of cell lysate were used for the immunoblots. After TU treatment, the major intracellular form of TGF-β1 polypeptide observed corresponded in size to nonglycosylated precursor. The level of this TGF-β1 precursor was consistently higher in TU treated cells as compared to control cells and, most likely, indicates an accumulation of this form within treated cells. These results strongly suggest that glycosylation is important for secretory exit and, without it, may lead to a build up of recombinant TGF-β1 inside the cells.

12.2.2. TIME COURSE FOR CHO TRANSFECTANT SECRETION OF TGF-β1

The rate and extent of secretion of recombinant TGF-β1 was measured from the transfected CHO cell cultures by pulse-labeling with [35-S]-methionine and -cysteine and chasing over variable time periods. Culture medium was collected and fractionated by SDS-PAGE followed by fluorography. The results are shown in FIG. 42A. The three recombinant forms of TGF-β1 appeared gradually in the conditioned medium and the rate of secretion then leveled off during the course of the experiment. The ratio of the amount of mature TGF-β1 to that of the precursor forms did not appear to vary suggesting that proteolytic processing is complete upon secretion and most likely occurs intracellularly.

FIG. 42B shows a quantitative assessment of the secretion of TGF-β1 corresponding to three independent pulse-chase experiments as determined by scanning fluorographs. After a lag time for secretion of approximately 1.5 h, the TGF-β1 polypeptides were secreted rapidly by the CHO cells and after 6 h greater than 50% of the secreted recombinant protein was detectable. The lag time of 1.5 h is somewhat longer than that reported for the lag time of secretion of other polypeptides, a difference which may reflect variations in the processing rates for glycoproteins or a cell-type dependency (Bauer et al., 1985, Biochem. Biophys. Res. Commun. 128:368–375; Leford and Davis, 1982, J. Biol. Chem. 258:3304–3308; Lodish et al., 1984, J. Cell. Biol. 98:1720–1729). After a 20 h chase, the level of secretion of the recombinant material as detected in the CHO conditioned medium began to plateau. A 6 h time point was chosen for further studies because greater than 50% of the recombinant material had been secreted at that time (FIG. 42).

12.2.3. INHIBITORS OF GLYCOSYLATION OR GLYCOSYLATIONAL PROCESSING AFFECT LEVEL OF SECRETED rTGF-β1

To further elucidate the role of glycosylation on the processing and secretion of TGF-β1 by CHO cells, transfected cells were treated with several glycosylation inhibitors and their effects on the secretion of recombinant growth factor tested. In addition to tunicamycin, four inhibitors affecting terminal processing of the growing oligosaccharide side chains were utilized. Castanospermine (CA) and deoxynojirimycin (dN) interfere with the initial trimming of glucose residues within the endoplasmic reticulum after addition of the core oligosaccharide (Heltkamp et al., 1982, Biosci. Rep. 2:899–906; Saunier et al., J. Biol. Chem. 257:14155–14161; Schwartz and Datema, 1984, Trends Biochem. Sci. 9:32–34). Swainsonine (SW) and deoxymannojirimycin (dMM), on the other hand, inhibit the mannosidases I and II of the golgi, respectively (Elbein et al., 1984, Arch. Biochem. Biophys. 235:579–588; Tulsiani et al., 1982, J. Biol. Chem. 257:7936–7939).

A fluorograph of the conditioned medium from TGF-β1 expressing CHO cells treated with the inhibitors is shown in FIG. 43A. The CHO cells were pretreated with the inhibitors for 1 h and then pulse labeled and chased. Supernatants were subsequently collected after a 6 h chase. consistent with the results shown in FIG. 41, TU drastically reduced the secretion of TGF-β1. Inhibition of glucosidase activity in the endoplasmic reticulum by CA and dN also markedly reduced secretion. In contrast, cells treated with dMM or SW, inhibitors of mannosidase activity in the golgi, slightly increased secretion.

FIG. 43B shows a summary of these results from three independent experiments. The level of secretion in the presence of TU, CA, and dN were between 5–15% the levels observed in control cells. SW and dMM resulted in increased levels of secreted, recombinant proteins with increases of nearly 30%. Time course experiments suggest a similar rate of secretion compared to control cells indicating a generalized increase or decrease in secretion rather than a change in rate. In addition, specific proteolytic processing of TGF-β1 did not appear to be altered following inhibitor treatment. In all cases, a similar ratio of pro-TGF-β1 ("a" in FIG. 43A) to the processed forms of TGF-β1 ("b" and "c" in FIG. 43A) were evident even in the absence of carbohydrate ("TU" in FIG. 43A). These results indicate that complete remodeling of TGF-β1 oligosaccharide side chains is not necessary for secretory exit as long as the initial trimming of glucose residues is maintained and that oligosaccharide integrity is not important for proteolytic processing of pre-pro-TGF-β1.

12.2.4. STRUCTURE OF TGF-β1 OLIGOSACCHARIDE SIDE CHAINS

The nature of the carbohydrate groups present on TGF-β1 polypeptides secreted by inhibitor treated CHO cells was investigated. Conditioned medium from pulse labeled CHO cells with and without inhibitors were collected and treated with N-glycanase, endo H, and neuraminidase. The results are shown in FIG. 44. N-glycanase, which removes all N-linked sugars, resulted in TGF-β1 precursor polypeptides "a" and "b" comigrating on reducing SDS-gels irrespective of inhibitor treatment. As expected, control treated cells were essentially insensitive to endo H, a glycosidase removing high mannose type oligosaccharide chains, confirming the proposed complex carbohydrate structure. Endo H treatment of supernatants from inhibitor treated CHO cells, however, indicated complete removal of TGF-β1 precursor side chains in the case of dMM and only partial sensitivities to this glycosidase resulting from treatment with CA, dN, and SW. Neuraminidase treatment revealed that dMM, CA, and dN contained no apparent sialylated residues. However, treatment with SW suggested that TGF-β1 precursor polypeptides released under these conditions contained a substantial sialic acid component within their oligosaccharide side chains.

12.2.5. MANNOSE 6-PHOSPHORYLATION OF TGF-β1 PRECURSOR POLYPEPTIDES RELEASED FROM INHIBITOR-TREATED CHO CELLS

The TGF-β1 precursor is readily labeled with 32-P]-orthophosphate and this incorporation is due to phosphorylation of mannose residues yielding mannose-6-phosphate; phosphorylation occurs within the first two carbohydrate side chains of the growth factor precursor (Section 9., supra). Since modification of the glycosylational pathway by inhibitor treatment may affect the mannose-6-phosphorylation of the precursor, cells were labeled with [32-P]-orthophosphate and ability of the TGF-β1 precursor polypeptides to become labeled examined (FIG. 45). Prominent phosphorylation was evident in TGF-β1 precursors from SW and dMM treated cells. The effects of CA and dN were much less apparent due to reduced secretion of TGF-β1 polypeptides. However, longer exposures revealed that [32-P]-labeling had occurred within proteins comigrating with the precursors. Thus, inhibitor treatment of CHO cells did not appear to affect the phosphorylation of the TGF-β1 polypeptides at mannose 6-phosphate.

12.2.6. DELETION MUTAGENESIS STUDIES

To provide further evidence concerning the role of glycosylation on the secretion of recombinant TGF-β1 proteins, a large portion of the precursor was deleted, resulting in an in-frame mutant lacking all three glycosylation sites. FIG. 46A illustrates the approach utilized for making the deletion. Digestion of DNA by SacII and religation afforded the removal of 160 amino acids within the pro region of TGF-β1. Religation occurred between Arg-50 and Gly-211 and is referred to as Δ51-210 TGF-β1. The deletion mutant was then placed into the expression plasmid CDM8 (Seed, 1987, Nature 329:840–842) downstream of the CMV promoter as illustrated (FIG. 46A).

The mutant DNA was transfected into COS-1 cells using a transient expression system, and the level of TGF-β1 secretion examined by immunoblotting (FIG. 46B). The expression vector containing wild type TGF-β1 was expressed in COS-1 cells and led to the secretion of all three forms of recombinant growth factor polypeptides (lane 2 in FIG. 46B). A control revealing these forms is also included on the immunoblot (lane 3 in FIG. 46B). In contrast, no detectable levels of TGF-β1 were observed in the supernatants of COS-1 cells transfected with the deletion mutant. In control cells, a small amount of TGF-β1 precursor was observed intracellularly; these results were similar to those obtained from a previous experiment (FIG. 41). For Δ51-210 TGF-β1 transfectants, an immunoreactive protein of about 20 kDal corresponding in size to that predicted for the deletion mutant was expressed intracellularly in these transfected COS-1 cells. The above results indicate that Δ51-210 TGF-β1 was not efficiently secreted by the cells and accumulated intracellularly. Although a rather large portion of the TGF-β1 precursor was removed by deletion, the lack of TGF-β1 secretion is consistent with the inhibitor results and implicate an important intracellular targeting role for the carbohydrate epitopes of the TGF-β1 precursor.

12.2.7. INTRACELLULAR PROTEOLYTIC PROCESSING WITHIN ACIDIC VESICLES

Proteolytic processing of TGF-β1 precursor at basic residues to yield mature TGF-β1 most likely occurs within the cells. In order to examine the nature of the protease involved TGF-β1 processing, transfected CHO cells were treated with weak bases or a monovalent ionophore. Both reagents increase the intra-vesicular pH from its acidic environment to one closer to neutrality and either affect the transport process or proteolytic processing (Devault, et al., 1984, J. Biol. Chem. 259:5146–5151; Mellman, et al., 1986, Ann. Rev. Biochem. 55:663–700; Poole, et al., 1981, J. Cell Biol. 90:665–690; Tartakoff and Vassalli, 1977, J. Exp. Med. 146:1332–1345; Tartakoff and Vassalli, 1978, J. Cell Biol. 79:284–299). Transfected CHO cells were treated with these reagents for 1 h prior to pulse labeling and chased in complete serum free medium containing these reagents for 6 h. Conditioned medium was then analyzed by SDS-PAGE; the corresponding fluorographs are shown in FIG. 47A. The weak bases ammonium chloride and chloroquine as well as the ionophore monensin greatly reduced the degree of proteolytic processing observed for TGF-β1 precursor. The overall level of secretion of the TGF-β1 molecules, on the other hand, was either uneffected or only slightly effected by these reagents. Interestingly, the carboxylic ionophore monensin has been shown to arrest secretion of immunoglobulins by plasma cells. (Tartakoff and Vassalli, 1977, J. Exp. Med. 146:1332–1345; Tarkokoff and Vassalli, 1978, J. Cell. Biol. 79:284–299.)

A summary of three independent experiments to quantitate these effects is illustrated in FIG. 47B. Since a slight effect on secretion was noted, we normalized the total levels of recombinant TGF-β1 released from the CHO cells by summing total TGF-β1 observed in the pulse chase experiment using densitometer scans of SDS-gel fluorographs. After normalization, the amount of mature TGF-β1 secreted was determined, indicating the level of proteolytic processing. Ammonium chloride produced the weakest effect at the concentration used in these experiments, showing a cleavage efficiency of about 70% of control values. Chloroquine and monensin, on the other hand, drastically reduced processing to levels approaching 20% of controls. These results strongly indicate that proteolytic cleavage of precursor to yield mature TGF-β1 occurs by a protease having an acidic pH optimum.

Other reports have indicated that the above reagents may effect glycosylation (Mellman, et al., 1986, Ann. Rev. Biochem. 55:663–700; Tartakoff and Vassalli, 1977, J. Exp. Med. 146:1332–1345; Tartakoff and Vassalli, J. Cell Biol. 79:284–299; Thorens, et al., 1986, Nature 321:618–620). In fact, FIG. 47A indicates that monensin and chloroquine may change the structure of the oligosaccharide side chains since the proteins migrated on SDS gels differently. To investigate this further, glycosidases were employed to analyze the carbohydrate structure of the secreted TGF-β1 precursors (FIG. 48). In all cases the results were similar; the treated samples showed the same sensitivity to N-glycanase, endo H and neuraminidase as did control treated material. Following neuraminidase digestion, the TGF-β1 precursor proteins migrated identically. Thus, the electrophoretic migration changes induced by monensin and chloroquine on the TGF-β1 precursor were, most likely, due to changes in the degree of sialylation. This result is consistent with other reports which have noted changes in terminal glycosylation following treatment with these agents (Tartakoff and Vassalli, 1977, J. Exp. Med. 146:1332–1345; Tartakoff and Vassalli, 1978, J. Cell Biol. 79:284–299; Thorens, et al., 1986, Nature 321:618–620). In addition, monensin treated cultures still incorporated [32]-P-orthophosphate into the precursor molecule, indicating that intravesicular pH does not affect phosphorylation at mannose residues. It is unlikely that the subtle change in carbohydrate structure observed following monensin and chloroquine treatment could affect proteolytic processing since the glycosidase trimming inhibitors, which drastically alter carbohydrate side chain structure, resulted in no noticeable effect on proteolytically processed TGF-β1 proteins.

13. EXAMPLE: GAMMA INTERFERON-INDUCED ACTIVATION OF LATENT TGF-β BY HUMAN MACROPHAGES

13.1. MATERIALS AND METHODS
13.1.1. PURIFICATION OF LATENT TGF-β1

CHO cell cultures expressing latent rTGF-β1 (LnTGF-β1) 1.4 mg/l) were grown in low serum (0.2%) and supernatants were harvested 24 hrs post-seeding. Supernatants were clarified by low speed centrifugation and protein precipitated with ammonium sulfate (80% saturation at pH 7.2). The precipitate was resuspended in cold phosphate buffered saline (PBS) and extensively dialyzed at 4° C. for 2 days. A sample containing 6.2 mg of protein was loaded on a P-100 column equilibrated in PBS 100–200 MESH (BioRad). Inactive LnTGF-β1 was resolved from residual active TGF-β on this column and was localized by visualization of silver stained SDS-PAGE gels (Blobel and Dobberstein, 1975, J. Cell Biol. 67: 835–851; Morrissey, 1981, Analyt. Biochem. 117:

307–310) and subsequent acid activiation as detected in a CCL-64 mink lung epithelial cell growth inhibition assay (GIA) (Section 7.1.6., supra).

Briefly, cells were cultured on 96-well tissue culture plates (Falcon 3072) at a concentration of $3 \times 10^3$ cells per μl of DMEM containing 10% fetal calf serum. TGF-β standards tested were in 0.2M acetic acid and were lyophilized in sterile 12×75 mm tubes (Falcon 2063). Lyophilized samples were resuspended in DMEM with 10% fetal calf serum, and were added in 50 μl to the test wells in triplicate 5 hr after plating (non-acidified samples wer tested without prior treatment). After incubation at 37° C. in a humidified 5% $CO_2$-95% air atmosphere for 72 hrs, [$^{125}$I]Idudr (Amersham IM 355) was added in 50 μl of medium (1 μCi/ml). The cells were incubated an additional 24 hrs and were then washed 1× with PBS, fixed for 10 min in 200 μl of methanol, and air dried for 15 min. The cells were solubilized in 200 μl of 1M NaOH for 20 min at 65° C. and labeled material collected using the Titertek Supernatant Collection System (Flow Laboratories, 78-210-05). Inhibition-stimulation of growth was expressed as the precent decrease or increase of [$^{125}$I]IdUdr incorporation of the treated cells when compared to the incorporation of untreated cells.

13.1.2. ACTIVATION OF LATENT TGF-β1 ASSAY

Monocytes were prepared from fractionated fresh human blood, activated and seeded ($2 \times 10^6$ cells/ml) in Dulbecco's Modified Eagles Media (DMEM). Cultures were incubated at 37° C. for 24 hrs in the presence or absence of purified 5 μg/ml LnTGF-β1 and/or recombinant gamma interferon (rγINF), 100 U/ml (AMGEN). Supernatants were harvested, clarified by low speed centrifugation and frozen on dry ice prior to testing serial dilutions in triplicate in the growth inhibitory assay (GIA). Values for TGF-β were determined utilizing a standard GIA curve generated with purified platelet TGF-β.

13.2. RESULTS

Table XII shows that the TGF-β precursor purified at neutral pH exhibits minimal bioactivity (even at concentrations of 1 μg/ml). Transient pretreatment with acetic acid, however, was able to activate approximately 7.5% of the precursor on a weight basis, i.e., 250 ng of acidified precursor yielded 18.7 ng of active TGF-β. On a molar basis, this corresponds to a 40% activation. SDS-PAGE analysis demonstrates that the acid activated molecule has a mass identical to native TGF-β (24 kd) and primary sequence studies indicate that the residual non-activated TGF-β precursor complex is a result of spurious disulfide bond formation between cysteine residues in the precursor and the mature TGF-β homodimer (Marquardt et al., in press). Using this purified polyprotein as our source of mature exogenous TGF-β1 precursor, we examined the ability of various cultured cells to activate and release TGF-β into culture supernatants. No activation was observed with several established lymphocytic cell lines including HUT-78, CEM and the monocyte-derived line, U937. Likewise, freshly cultured human B and T cells displayed minimal, if any, activation.

TABLE XII

ACID ACTIVATION OF LATENT TGF-β1

| Recombinant Latent TGF-β | TGF-β Activity (growth inhibition) ng/ml Pretreatment | |
|---|---|---|
| ng/ml | None | Acid |
| 10 | 0 | 0.6 |
| 100 | 0 | 9.2 |
| 250 | <0.5 | 18.7 |
| 1000 | 6.0 | 80.14 |

The results presented in TABLE XIII indicate that human monocytes cultured in the presence of 100 u/ml rγINF and 5 μg LnTGF-β1 are able to activate latent TGF-β1. Human peripheral blood monocytes release minimal amounts of active TGF-β (<0.1 pM/ml of culture supernatants). Incubation of monocytes with 5 μg of LnTGF-β1 for 24 hrs resulted in some basal activation (approximately 0.1 pM/ml per 1×10$^7$ cells However, monocytes cultured in the presence of 100 U/ml of rγ-INF and 5 μg of LnTGF-β1 resulted in a striking increase in the amount of active TGF-β detected in supernatants. The extent of activation was substantial, 2.1–2.5 pM TGF-β1/ml, which is equivalent to about half what was achieved with acid treatment alone (cytokine/acid activation ratio of 0.42 and 0.50, experiments 1 and 2, respectively) Control cultures of monocytes treated with rγ-INF alone did not result in any significant activation (0.2–0.4 pM/ml) of the endogenous latent TGF-β purportedly released by some cultured monocytes (Assoian et al., 1987, Proc. Natl. Sci. U.S.A. 84: 6020–6024). The amount of activation was proportional to the amount of LnTGF-β1 substrate added and saturation was achieved at 10 μg/ml substrate using 10$^7$ monocytes and 100 μ/ml rγ-INF. Kinetics of the activation demonstrated maximal processing and release of TGF-β 7–8 hours post incubation of LnTGF-β with rγ-INF, indicating that processing may require γ-INF-induced gene transcription, perhaps involving the transcription of a processing enzyme gene(s).

TABLE XIII

GAMMA INTERFERON-INDUCED ACTIVATION OF LnTGF-β1 BY HUMAN MONOCYTES

| | p Moles TGF-β Activated/ml Experiment | | Activation Ratio Cytokine/Acid* Experiment | |
|---|---|---|---|---|
| | I | II | I | II |
| Monocytes alone | <0.1 | 0.4 | — | — |
| Monocytes + γ-INF | 0.2 | 0.4 | — | — |
| Monocytes + γ-INF + LnTGF-β1 | 2.1 | 2.5 | .42 | .50 |
| Monoctyes + LnTGF-β1 | 0.1 | <0.1 | — | — |

*2 hr in 1M acetic acid at 22° C.

As shown in FIG. 49, the activation of LnTGF-β1 by monocytes was dependent on the dose of γ-INF used. A measurable response was seen with as little as 10 units/ml of rγ-INF (10 ng/ml TGF-γ detected by the GIA). Previous experiments (TABLE XIII) were conducted at a dose of 100 U/ml γ-INF (20 ng/ml of TGF-β released) with a maximal saturating value reached with 1000 U/ml rγ-IFN. In separate experiments, recombinant IL-2 was able to stimulate fresh human T cells to process LnTGF-β1, but the response was weak relative to that observed with rγ-INF-treated monocytes (0.5 p Moles/TGF-β/2×10$^6$ cells/units of rIL-2).

Several experiments were conducted to determine whether the LnTGF-β1-dependent TGF-β growth inhibiting activity recovered from rγ-INF-treated monocyte cultures was indeed TGF-β activity. TGF-β was originally isolated because it stimulated normal rat kidney cells (NRK) to grow as colonies in soft agar in the presence of low amounts of EGF or TGF-α. As show in in FIG. 50, both acid-purified natural TGF-β1 and EGF are required to stimulate growth of NRK cell colonies (120 colonies per eight random low-power fields). Supernatants (no prior acidification) harvested from rγ-INF-treated monocytes incubated with TGF-β1 also effectively induced NRK cell colony formation; 1 and 100 ng of monocyte-activated rTGF-β1 stimulated the growth of 90 and 190 NRK colonies respectively. When the assays were done in the presence of a neutralizing monoclonal antibody to bovine bone-derived TGF-β1, NRK colony formation was suppressed (90% inhibition at a TGF-β concentration of 100 ng/ml). A proportional mAb inhibition of colony growth was dependent on the original concentration of TGF-β1 added to the assay.

Cultures of CHO cells expressing LnTGF-β1 were incubated overnight with $^3$H-leucine and labeled TGF-β1 precursor complex was purified as described in Materials and Methods. H$^3$-leucine labeled LnTGF-β1 was incubated with rγ-INF-treated and non-treated monocytes using serum-free conditions and supernatants were harvested and analyzed by SDS-PAGE under non-reducing conditions. The results are presented in FIG. 51. In addition to the 110 kd TGF-β1 precursor, a band was seen migrating with the 24 kd TGF-β standard in supernatants harvested from rγINF-treated cultures (lane A). This band was not as pronounced in supernatants harvested from monocyte cultures incubated with $^3$H-leucine LnTGF-β1 alone (lane B).

These results indicate that γINF effectively induces human monocytes to mediate the release of active TGF-β from a latent recombinant TGF-β complex. The TGF-β released into supernatants, derived from exogenously added LnTGF-β1, appears to be both functionally identical with TGF-β1 (mAb neutralization of NRK colony formation) and exhibits a mass (SDS-PAGE) identical to natural TGF-β isolated after purification at acid pH from platelet and bone.

14. DEPOSIT OF MICROORGANISMS

The following transformants have been deposited with the American Type Culture Collection, Rockville, Md., and have been assigned the listed accession numbers:

| Transfectant | Plasmid | Accession No. |
|---|---|---|
| CHO-TGF-β-3/2000 | pSV2-β-TGF | CRL 9434 |

The present invention is not to be limited in scope by the cell lines deposited since the deposited embodiments are intended as single illustrations of one aspect of the invention and any which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair and amino acid residue numbers and sizes given for nucleotides and peptides are approximate and are used for purposes of description.

What is claimed is:

1. A recombinant simian TGF-β1 polypeptide comprising an amino acid sequence as depicted in FIG. 1.

2. A recombinant simian TGF-β1 polypeptide of claim 1 comprising amino acid residue numbers 1 to 390.

3. A recombinant simian TGF-β1 polypeptide of claim 1 comprising amino acid residue numbers 30 to 390.

4. A recombinant simian TGF-β1 polypeptide of claim 1 comprising amino acid residue numbers 30 to 278.

5. A recombinant simian TGF-β1 polypeptide of claim 1, 2, 3 or 4 which is glycosylated.

6. A recombinant simian TGF-β1 polypeptide of claim 1, 2, 3 or 4 which is phosphorylated.

7. A recombinant simian TGF-β1 polypeptide of claim 6 which contains at least one mannose-6-phosphate.

8. A recombinant simian TGF-β1 polypeptide of claim 26 containing at least one mannose-6-phosphate linked to an asparagine linked sugar chain of the rTGF-β1 precursor.

9. A recombinant simian TGF-β1 polypeptide of claim 6 containing an asparagine at amino acid residue number 82.

10. A recombinant simian TGF-β1 polypeptide of claim 6 containing an asparagine at amino acid residue number 136.

11. A recombinant simian TGF-β1 polypeptide of claim 6 containing an asparagine at amino acid residue number 176.

12. A recombinant simian TGF-β1 polypeptide comprising an amino acid sequence as depicted in FIG. 1 in which amino acid residue number 33 is serine.

13. A recombinant simian TGF-β1 polypeptide comprising an amino acid sequence as depicted in FIG. 1 in which amino acid residue number 223 is serine.

14. A recombinant simian TGF-β1 polypeptide comprising an amino acid sequence as depicted in FIG. 1 in which amino acid residue number 225 is serine.

15. A recombinant simian TGF-β1 polypeptide comprising an amino acid sequence as depicted in FIG. 1 in which amino acid residue numbers 223 and 225 are serine.

16. A recombinant simian TGF-β1 polypeptide of claim 12, 13, 14, or 15 comprising amino acid residue numbers 1 to 390.

17. A recombinant simian TGF-β1 polypeptide of claim 12, 13, 14 or 15 comprising amino acid residue numbers 30 to 390.

18. A recombinant simian TGF-β1 polypeptide of claim 12, 13, 14, or 15 comprising amino acid residue numbers 30 to 278.

19. A recombinant simian TGF-β1 polypeptide of claim 12, 13, 14, or 15, which is glycosylated.

20. A recombinant simian TGF-β1 polypeptide of claim 12, 13, 14, or 15, which is phosphorylated.

21. A recombinant simian TGF-β1 polypeptide of claim 20 which contains at least one mannose-6-phosphate.

22. A recombinant simian TGF-β1 polypeptide of claim 21 in which the mannose-6-phosphate linked to an asparagine linked sugar chain of the rTGF-β1 precursor.

23. A recombinant simian TGF-β1 polypeptide of claim 20 containing an asparagine at amino acid residue number 82.

24. A recombinant simian TGF-β1 polypeptide of claim 20 containing an asparagine at amino acid residue number 136.

25. A recombinant simian TGF-β1 polypeptide of claim 20 containing an asparagine at amino acid residue number 176.

26. The recombinant simian TGF-β1 polypeptide of claim 16 which is glycosylated.

27. The recombinant simian TGF-β1 polypeptide of claim 17 which is glycosylated.

28. The recombinant simian TGF-β1 polypeptide of claim 18 which is glycoslyated.

29. The recombinant simian TGF-β1 polypeptide of claim 16 which is phosphorylated.

30. The recombinant simian TGF-β1 polypeptide of claim 17 which is phosphorylated.

31. The recombinant simian TGF-β1 polypeptide of claim 18 which is phosphorylated.

32. An isolated latent simian recombinant TGF-β1 gives rise to biologically active TGF-β1 upon acid activation.

* * * * *